US008349826B2

(12) United States Patent
Hubschwerlen et al.

(10) Patent No.: US 8,349,826 B2
(45) Date of Patent: Jan. 8, 2013

(54) OXAZOLIDINONE DERIVATIVES

(75) Inventors: Christian Hubschwerlen, Durmenach (FR); Georg Rueedi, Allschwil (CH); John-Philippe Surivet, Kembs (FR); Cornelia Zumbrunn-Acklin, Basel (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 98 days.

(21) Appl. No.: 12/918,779

(22) PCT Filed: Feb. 20, 2009

(86) PCT No.: PCT/IB2009/050702
§ 371 (c)(1),
(2), (4) Date: Aug. 20, 2010

(87) PCT Pub. No.: WO2009/104159
PCT Pub. Date: Aug. 27, 2009

(65) Prior Publication Data
US 2010/0331308 A1 Dec. 30, 2010

(30) Foreign Application Priority Data

Feb. 22, 2008 (WO) .................. PCT/IB2008/050651
Oct. 7, 2008 (WO) .................. PCT/IB2008/054095

(51) Int. Cl.
*A61K 31/00* (2006.01)
*C07D 241/36* (2006.01)
(52) U.S. Cl. ..................... 514/210.21; 514/52; 544/354; 544/52; 546/157
(58) Field of Classification Search ............. 514/210.21, 514/52; 544/354, 52; 546/157
See application file for complete search history.

(56) References Cited

U.S. PATENT DOCUMENTS

| 5,245,037 A | 9/1993 | Kuramoto et al. |
| 5,792,765 A | 8/1998 | Riedl et al. |
| 2007/0060558 A1* | 3/2007 | Sanchez et al. ............... 514/192 |

FOREIGN PATENT DOCUMENTS

| EP | 0 185 319 | 6/1986 |
| EP | 0 789 025 | 8/1997 |
| WO | WO 01/30782 | 5/2001 |
| WO | WO 02/50040 | 6/2002 |
| WO | WO 02/056882 | 7/2002 |
| WO | WO 03/087098 | 10/2003 |
| WO | WO 2004/087647 | 10/2004 |
| WO | WO 2006/112464 | 10/2006 |
| WO | WO 2006/134378 | 12/2006 |
| WO | WO 2007/071936 | 6/2007 |
| WO | WO 2007/138974 | 12/2007 |
| WO | WO 2007/144423 | 12/2007 |
| WO | WO 2008/065198 | 6/2008 |
| WO | WO 2008/126024 | 10/2008 |
| WO | WO 2008/126034 | 10/2008 |

OTHER PUBLICATIONS

Albert et al., Journal of Organic Chemistry, vol. 73, pp. 1093-1098 (2008).
Ali et al., Heteroatom Chemistry, vol. 17, No. 4, pp. 280-288 (2006).
Alvrez-Perez et al., Journal of American Chemical Society, vol. 103, pp. 1836-1838 (2008).
Bal et al., Tetrahedron, vol. 37, pp. 2091-2096 (1981).
Benz, Comprehensive Organic Synthesis, vol. 6, pp. 381-417 (1991).
Carboni et al., Gazetta Chimica Italiana, vol. 97, No. 7, pp. 1061-1075 (1967).
Cesur et al., Fused Heterocycles, vol. 8, No. 5, pp. 433-442 (2002).
Chang et al., Journal of Medicinal Chemistry, vol. 36, pp. 2558-2568 (1993).
Chen et al., Organic Letters, vol. 8, No. 24, pp. 5609-5612 (2006).
Clouet et al., Advanced Synthesis & Catalysis, vol. 346, pp. 1195-1204 (2004).
Fatiadi, Synthesis, pp. 85-127 (1987).
Geneste et al., Bioorganic & Medicinal Chemistry Letters, vol. 16, pp. 658-662 (2006).
Gerbino, Index for Remington, The Science and Practice of Pharmacy, 21$^{st}$ Edition (2005).
Gould et al. International Journal of Pharmaceutics, vol. 33, pp. 201-217 (1986).
Greene et al., Protecting Groups in Organic Synthesis, 3$^{rd}$ Edition, pp. 494-653 (1999).
Greene et al., Protecting Groups in Organic Synthesis, 3$^{rd}$ Edition, pp. 369-453 (1999).
Greene et al., Protecting Groups in Organic Synthesis, 3$^{rd}$ Edition, pp. 17-245, particularly pp. 23-147, 133-139 and 142-143 (1999).
Johannes et al., Organic Letters, vol. 7, No. 18, pp. 3997-4000 (2005).
Kolb et al., Chemical Reviews, vol. 94, No. 8, 2483-2547 (1994).
Kowalski et al., Journal of Heterocyclic Chemistry, vol. 42, pp. 883-888 (2005).
Larock, Comprehensive Organic Transformations, A guide to Functional Group Preparations 2nd Edition, Section Nitriles, Carboxylic Acids and Derivatives, pp. 1653-1661 (1999).
Larock, Comprehensive Organic Transformations, A guide to Functional Group Preparations 2nd Edition, Section Amines, pp. 779-784 (1999).
Larock, Comprehensive Organic Transformations. A guide to Functional Group Preparations, 2nd Edition, Section Nitriles, Carboxylic Acids and Derivatives, pp. 1653-1661 (1999).
Larock, R; Index of "Comprehensive Organic Transformations: A Guide to Functional Group Preparations," Second Edition, pp. 1941-1949 (1999).

(Continued)

Primary Examiner — Rei-tsang Shiao
(74) Attorney, Agent, or Firm — Hunton & Williams LLP

(57) ABSTRACT

The invention relates to compounds of Formula (I)

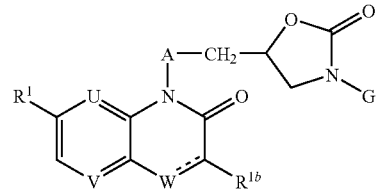

Formula (I)

wherein U, V, W, R$^1$, R$^{1b}$, A and G are as defined in the description, to pharmaceutically acceptable salts of such compounds and to the use of these compounds in the manufacture of a medicament for the prevention or treatment of a bacterial infection.

23 Claims, No Drawings

OTHER PUBLICATIONS

Neunhoeffer et al., Chemische Berichte, vol. 123, vol. 12, pp. 2453-2454 (1990).
Roma et al., Heterocycles, vol. 25, No. 1, pp. 329-332 (1987).
Solladie-Cavallo et al., Journal of Organic Chemistry, vol. 55, pp. 4750-4754 (1990).
Takemoto et al., Biochemistry, Biotechnology, and Biochemistry, vol. 58, No. 4, pp. 788-789 (1994).
Turner, Journal Organic Chemistry, vol. 55, pp. 4744-4750 (1990).
Ullrich et al., Tetrahedron Letters, vol. 44, pp. 4207-4211 (2003).
Wnuk et al., Journal of Organic Chemistry, vol. 55, pp. 4757-4760 (1990).
International Search Report for International Application No. PCT/IB2009/050702 mailed Jun. 4, 2009.

* cited by examiner

OXAZOLIDINONE DERIVATIVES

CROSS-REFERENCE TO RELATED APPLICATIONS

This application is the national phase application of PCT/IB2009/050702, filed Feb. 20, 2009, which claims the benefit of PCT/IB2008/050651, filed Feb. 22, 2008 and PCT/IB2008/054095, filed Oct. 7, 2008, the contents of all of which are hereby incorporated by reference as if fully set forth herein.

FIELD OF THE INVENTION

The present invention concerns novel oxazolidinone antibiotic derivatives, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram positive and Gram negative aerobic and anaerobic bacteria and mycobacteria.

BACKGROUND OF THE INVENTION

The intensive use of antibiotics has exerted a selective evolutionary pressure on micro-organisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus*, *Streptococcus pneumoniae*, *Enterococcus* spp., and *Pseudomonas aeruginosa*, major sources of infections, are becoming multi-drug resistant and therefore difficult if not impossible to treat:

- *S. aureus* is resistant to β-lactams, quinolones and now even to vancomycin;
- *S. pneumoniae* is becoming resistant to penicillin or quinolone antibiotics and even to new macrolides;
- Enteroccocci are quinolone and vancomycin resistant and β-lactam antibiotics are inefficacious against these strains;
- Enterobacteriacea are cephalosporin and quinolone resistant;
- *P. aeruginosa* are β-lactam and quinolone resistant.

Further new emerging organisms like *Acinetobacter* spp. or *Clostridium difficile*, which have been selected during therapy with the currently used antibiotics, are becoming a real problem in hospital settings. In addition, microorganisms that are causing persistent infections are increasingly being recognized as causative agents or cofactors of severe chronic diseases like peptic ulcers or heart diseases.

Certain heterocyclic compounds as antibacterial agents are known from WO 2007/138974. Compounds for the treatment of multi-drug resistant bacterial infections are disclosed in WO 2006/134378. Piperazine derivatives, containing a quinoline analog moiety, useful in methods of treatment of bacterial infections, are disclosed in WO 02/50040.

Various embodiments of the invention are presented hereafter:

BRIEF SUMMARY OF THE INVENTION

1) The present invention relates to novel antibiotic compounds of Formula (I)

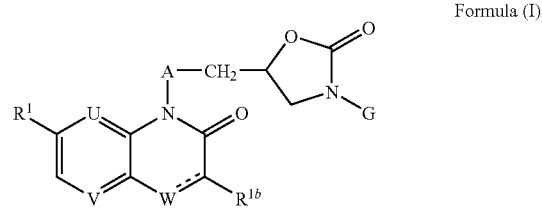

Formula (I)

wherein

"-----" is a bond or is absent;

$R^1$ represents $(C_1-C_4)$alkoxy or halogen;

$R^{1b}$ represents H or $(C_1-C_3)$alkyl;

U and V each independently represent CH or N;

W represents CH or N, or, in case "----" is absent, W represents $CH_2$ or NH;

with the proviso that at least one of U, V and W represents CH or $CH_2$;

A represents $-CH_2-CH(R^2)-B-NH-$* or $-CH(R^3)-CH_2-N(R^4)-[CH_2]_m-$*; wherein the asterisks indicate the bond which is linked via the $CH_2$-group to the oxazolidinone moiety;

B represents $CH_2$ or CO; and $R^2$ represents hydrogen, OH or $NH_2$;

$R^3$ and $R^4$ both represent hydrogen, or $R^3$ and $R^4$ together form a methylene bridge;

m represents the integer 0, 1 or 2; and

G represents phenyl which is mono-substituted in position 3 or 4, or disubstituted in positions 3 and 4, wherein each substituent is independently selected from the group consisting of $(C_1-C_4)$alkyl (notably methyl and ethyl), $(C_1-C_3)$alkoxy and halogen (notably fluorine); or G represents a group selected from the group consisting of the groups $G^1$, $G^2$, $G^3$, $G^4$, $G^5$ and $G^6$ drawn below:

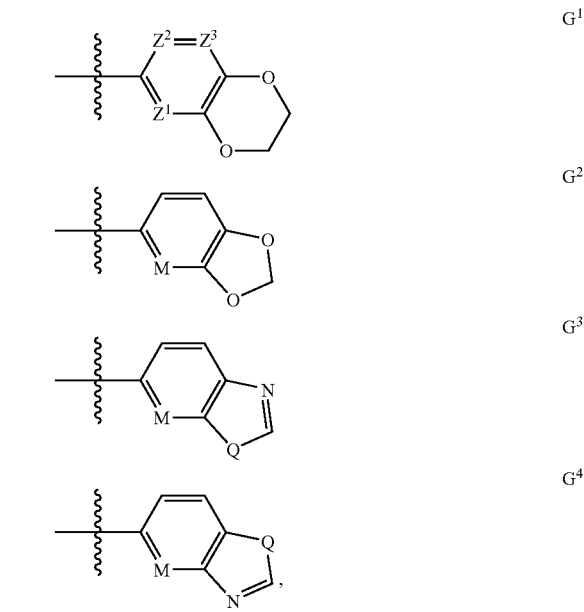

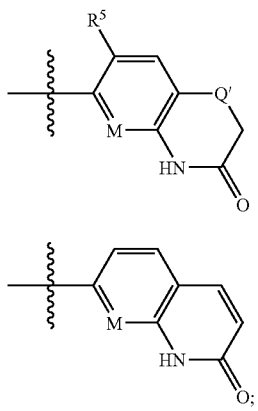

wherein

M represents CH or N;

Q and Q' independently represent S or O;

$Z^1$ represents N, $Z^2$ represents CH, and $Z^3$ represents CH; or $Z^1$ represents CH, $Z^2$ represents N, and $Z^3$ represents CH or N; or $Z^1$ represents CH, $Z^2$ represents $CR^5$, and $Z^3$ represents CH; or $Z^1$ represents CH, $Z^2$ represents CH, and $Z^3$ represents N; and $R^5$ represents hydrogen or fluorine.

The invention also relates to salts, especially pharmaceutically acceptable salts, of the compounds of Formula (I).

DETAILED DESCRIPTION OF PREFERRED EMBODIMENTS

The following paragraphs provide definitions of the various chemical moieties for the compounds according to the invention and are intended to apply uniformly throughout the specification and claims, unless an otherwise expressly set out definition provides a broader or narrower definition.

In this patent application, a bond interrupted by a wavy line shows the point of attachment of the radical drawn.

Further, an asterisk in a group —CH$_2$—CH(R$^2$)-B-NH—* or —CH(R$^3$)—CH$_2$—N(R$^4$)—[CH$_2$]$_m$—* as used for the substituent A indicates the bond which is linked via the CH$_2$-group to the oxazolidinone moiety.

Further, for avoidance of any doubt, a group —CH(R$^3$)—CH$_2$—N(R$^4$)—[CH$_2$]$_m$—* wherein R$^3$ and R$^4$ together form a methylene bridge, as used for the substituent A, means a group

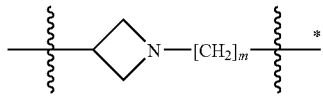

Further, for avoidance of any doubt, a group

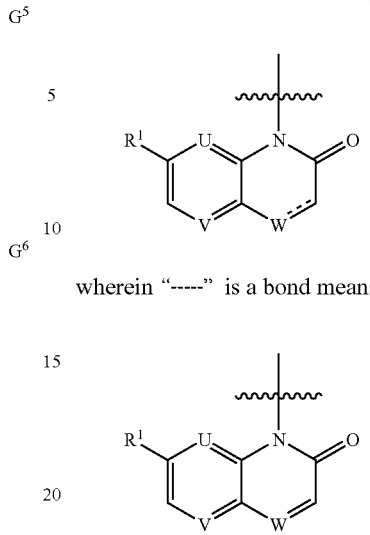

wherein "-----" is a bond means a group wherein W represents CH or N. Likewise, a group

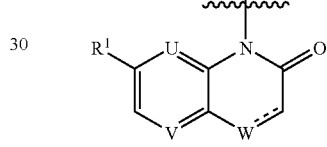

wherein "-----" is absent means a group

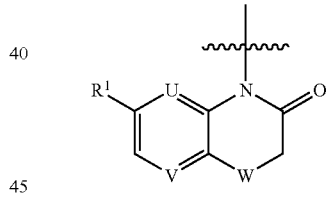

wherein W represents CH$_2$ or NH.

The term "halogen" refers to fluorine, chlorine, bromine or iodine; especially to fluorine, chlorine or bromine; preferably to fluorine or chlorine. In another embodiment, the term halogen as used for the substituent R$^1$ preferably refers to bromine.

The term "alkyl", used alone or in combination, refers to a straight or branched chain alkyl group containing one to four carbon atoms. Representative examples of alkyl groups include methyl, ethyl, n-propyl, iso-propyl, n-butyl, iso-butyl, sec-butyl and tert-butyl. Preferred are methyl, ethyl n-propyl and iso-propyl. Most preferred are ethyl and methyl.

The term "alkoxy", used alone or in combination, refers to an alkyl-O-group wherein the alkyl group is as defined before. The term "(C$_x$-C$_y$)alkoxy" (x and y each being an integer) refers to an alkoxy group as defined before containing x to y carbon atoms. For example a (C$_1$-C$_4$)alkoxy group contains from one to four carbon atoms. Representative examples of alkoxy groups include methoxy, ethoxy, n-propoxy, iso-propoxy, n-butoxy, iso-butoxy, sec-butoxy and tert-butoxy. Preferred are ethoxy and methoxy. Most preferred is methoxy. Preferred (C$_1$-C$_3$)alkoxy groups, as used for the substituent G representing substituted phenyl, are straight chain $(C_1-C_3)$alkoxy groups such as methoxy, ethoxy and n-propoxy, notably methoxy and ethoxy.

Preferred groups G representing

"a group selected from the group consisting of the groups $G^1$, $G^2$, $G^3$, $G^4$, $G^5$ and $G^6$ drawn below:

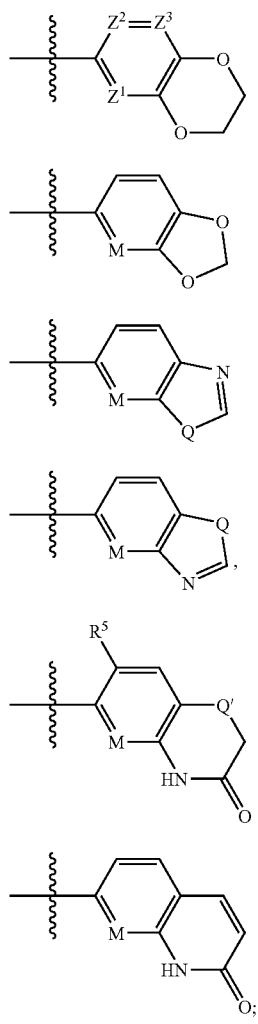

wherein
M represents CH or N;
Q and Q' independently represent S or O;
  $Z^1$ represents N, $Z^2$ represents CH, and $Z^3$ represents CH; or
  $Z^1$ represents CH, $Z^2$ represents N, and $Z^3$ represents CH or N; or
  $Z^1$ represents CH, $Z^2$ represents $CR^5$, and $Z^3$ represents CH; or
  $Z^1$ represents CH, $Z^2$ represents CH, and $Z^3$ represents N; and
$R^5$ represents hydrogen or fluorine"
as used for Formula (I) are those groups G wherein
M represents CH or N;
Q and Q' independently represent S or O;
  $Z^1$ represents CH or N, $Z^2$ represents CH, and $Z^3$ represents CH; or
  $Z^1$ represents CH, $Z^2$ represents N, and $Z^3$ represents N; and
$R^5$ represents hydrogen.

Examples of such groups G are 2,3-dihydro-benzo[1,4]dioxin-6-yl, benzo[1,3]dioxol-5-yl, 3-oxo-3,4-dihydro-2H-benzo[1,4]oxazine-6-yl, 3-oxo-3,4-dihydro-2H-benzo[1,4]thiazine-6-yl, 7-fluoro-3-oxo-3,4-dihydro-2H-benzo[1,4]thiazin-6-yl, 3-oxo-3,4-dihydro-2H-pyrido[3,2-b][1,4]oxazine-6-yl, 2-oxo-1,2-dihydro-quinoline-7-yl, benzothiazole-5-yl, benzothiazole-6-yl, benzooxazole-5-yl and benzooxazole-6-yl and in addition to the above listed groups also 6,7-dihydro-[1,4]dioxino[2,3-c]pyridazin-3-yl. In a sub-embodiment, examples are 2,3-dihydro-benzo[1,4]dioxin-6-yl, benzo[1,3]dioxol-5-yl, 3-oxo-3,4-dihydro-2H-benzo[1,4]oxazine-6-yl, 3-oxo-3,4-dihydro-2H-benzo[1,4]thiazine-6-yl, 3-oxo-3,4-dihydro-2H-pyrido[3,2-b][1,4]oxazine-6-yl, 2-oxo-1,2-dihydro-quinoline-7-yl, benzothiazole-5-yl, benzothiazole-6-yl, benzooxazole-5-yl and benzooxazole-6-yl, and in addition to the above listed groups also 6,7-dihydro-[1,4]dioxino[2,3-c]pyridazin-3-yl. In another sub-embodiment, examples are 2,3-dihydro-benzo[1,4]dioxin-6-yl, 3-oxo-3,4-dihydro-2H-benzo[1,4]oxazin-6-yl, 3-oxo-3,4-dihydro-2H-benzo[1,4]thiazin-6-yl, 7-fluoro-3-oxo-3,4-dihydro-2H-benzo[1,4]thiazin-6-yl, and 3-oxo-3,4-dihydro-2H-pyrido[3,2-b][1,4]oxazin-6-yl. Preferred are 2,3-dihydro-benzo[1,4]dioxin-6-yl, 3-oxo-3,4-dihydro-2H-benzo[1,4]oxazin-6-yl, 3-oxo-3,4-dihydro-2H-benzo[1,4]thiazin-6-yl, and 7-fluoro-3-oxo-3,4-dihydro-2H-benzo[1,4]thiazin-6-yl. In a sub-embodiment preferred are 2,3-dihydro-benzo[1,4]dioxin-6-yl, 3-oxo-3,4-dihydro-2H-benzo[1,4]oxazine-6-yl and 3-oxo-3,4-dihydro-2H-benzo[1,4]thiazine-6-yl.

Further embodiments of the invention are presented hereafter:

2) A further embodiment of the invention relates to compounds according to embodiment 1), wherein the stereocenter at position 5 of the oxazolidin-2-one ring is in (R)-configuration:

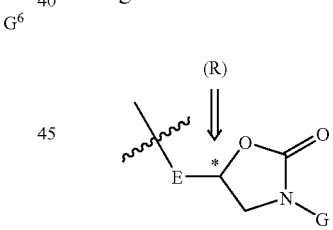

3) A further embodiment of the invention relates to compounds according to embodiment 1), wherein the stereocenter at position 5 of the oxazolidin-2-one ring is in (S)-configuration:

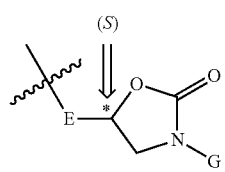

4) A further embodiment of the invention relates to compounds according to any one of embodiments 1) to 3), wherein "-----" is absent and W represents $CH_2$ or NH (especially $CH_2$).

5) A further embodiment of the invention relates to compounds of Formula (I) according to any one of embodiments 1) to 3) wherein "-----" is a bond and U, V and W independently represent CH or N, with the proviso that at least one of U, V and W represents CH.

6) A further embodiment of the invention relates to compounds according to any one of embodiments 1) to 3) or 5), wherein U, V and W each represent CH, or U and V each represent CH and W represents N, or U and W each represent N and V represents CH.

7) A further embodiment of the invention relates to compounds according to any one of embodiments 1) to 6), wherein U represents CH.

8) A further embodiment of the invention relates to compounds according to any one of embodiments 1) to 6), wherein U represents N.

9) A further embodiment of the invention relates to compounds according to any one of embodiments 1) to 8), wherein V represents CH.

10) A further embodiment of the invention relates to compounds according to any one of embodiments 1) to 8), wherein V represents N.

11) A further embodiment of the invention relates to compounds according to any one of embodiments 1) to 3) or 5) to 10), wherein W represents CH.

12) A further embodiment of the invention relates to compounds according to any one of embodiments 1) to 3) or 5) to 10), wherein W represents N.

13) A further embodiment of the invention relates to compounds according to any one of embodiments 1) to 12), wherein $R^1$ represents $(C_1-C_4)$alkoxy (preferably methoxy).

14) A further embodiment of the invention relates to compounds according to any one of embodiments 1) to 12), wherein $R^1$ represents halogen (preferably bromine).

15) A further embodiment of the invention relates to compounds according to any one of embodiments 1) to 14), wherein A represents —$CH_2$—$CH(R^2)$-B-NH—*.

16) A further embodiment of the invention relates to compounds according to any one of embodiments 1) to 15), wherein $R^2$ represents hydrogen or OH.

17) A further embodiment of the invention relates to compounds according to any one of embodiments 1) to 15), wherein $R^2$ represents OH or $NH_2$.

18) A further embodiment of the invention relates to compounds according to any one of embodiments 1) to 15), wherein $R^2$ represents hydrogen.

19) A further embodiment of the invention relates to compounds according to any one of embodiments 1) to 15), wherein $R^2$ represents OH.

20) A further embodiment of the invention relates to compounds according to any one of embodiments 1) to 19), wherein B represents $CH_2$.

21) A further embodiment of the invention relates to compounds according to any one of embodiments 1) to 19), wherein B represents CO.

22) A further embodiment of the invention relates to compounds according to any one of embodiments 1) to 14), wherein A represents —$CH(R^3)$—$CH_2$—$N(R^4)$—$[CH_2]_m$—* wherein $R^3$ and $R^4$ together form a methylene bridge and m represents the integer 0, 1 or 2 (notably 1 or 2, and in particular 1), i.e. wherein A is

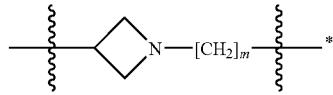

23) A further embodiment of the invention relates to compounds according to any one of embodiments 1) to 14), wherein A represents —$CH(R^3)$—$CH_2$—$N(R^4)$—$[CH_2]_m$—* wherein $R^3$ and $R^4$ both represent hydrogen; and m represents the integer 0, 1 or 2 (notably 1 or 2 and in particular 1).

24) A further embodiment of the invention relates to compounds according to any one of embodiments 1) to 23), wherein G represents a group selected from the group consisting of the groups $G^1$, $G^2$, $G^5$ and $G^6$ wherein:
M represents CH or N;
Q' represents S or O;
$Z^1$ represents N, $Z^2$ represents CH, and $Z^3$ represents CH; or
$Z^1$ represents CH, $Z^2$ represents N, and $Z^3$ represents CH or N; or
$Z^1$ represents CH, $Z^2$ represents $CR^5$, and $Z^3$ represents CH; or
$Z^1$ represents CH, $Z^2$ represents CH, and $Z^3$ represents N; and
$R^5$ represents hydrogen or fluorine.

25) A further embodiment of the invention relates to compounds according to embodiment 24), wherein
M represents CH or N;
Q' represents S or O;
$Z^1$ represents CH or N, $Z^2$ represents CH, and $Z^3$ represents CH; or
$Z^1$ represents CH, $Z^2$ represents N, and $Z^3$ represents N; and
$R^5$ represents hydrogen.

26) A further embodiment of the invention relates to compounds according to any one of embodiments 1) to 24), wherein G represents a group selected from the group consisting of the groups $G^1$, $G^2$, $G^5$ and $G^6$ wherein:
each of M and $Z^1$ represents CH or N;
each of $Z^2$ and $Z^3$ represents CH;
Q' represents S or O; and
$R^5$ represents hydrogen or fluorine.

27) A further embodiment of the invention relates to compounds according to any one of embodiments 1) to 24), wherein G represents a group selected from the group consisting of the groups $G^1$ and $G^5$ wherein:
each of M and $Z^1$ represents CH or N;
each of $Z^2$ and $Z^3$ represents CH;
Q' represents S or O; and
$R^5$ represents hydrogen or fluorine.

28) A further embodiment of the invention relates to compounds according to any one of embodiments 1) to 24), 26) or 27) wherein G represents a group $G^5$ wherein M represents CH or N; Q' represents O or S; and $R^5$ represents hydrogen or fluorine.

29) A further embodiment of the invention relates to compounds according to any one of embodiments 1) to 27) wherein G represents a group $G^5$ wherein $Z^1$ represents CH or N and each of $Z^2$ and $Z^3$ represents CH.

30) A further embodiment of the invention relates to compounds according to any one of embodiments 1) to 28), wherein $R^5$ represents hydrogen.

31) A further embodiment of the invention relates to compounds according to any one of embodiments 1) to 30), wherein, if present, M and $Z^1$ both represent CH.
32) A further embodiment of the invention relates to compounds according to any one of embodiments 1) to 30), wherein, if present, M and $Z^1$ both represent N.
33) A further embodiment of the invention relates to compounds according to any one of embodiments 1) to 28) or 30) to 32), wherein, if present, Q' represents S.
34) A further embodiment of the invention relates to compounds according to any one of embodiments 1) to 28) or 30) to 32), wherein, if present, Q' represents O.
35) A further embodiment of the invention relates to compounds according to any one of embodiments 1) to 23) or 30) to 34), wherein, if present, Q represents S.
36) A further embodiment of the invention relates to compounds according to any one of embodiments 1) to 23) or 30) to 34), wherein, if present, Q represents O.
37) A further embodiment of the invention relates to compounds according to any one of embodiments 1) to 24), wherein G represents a group selected from 2,3-dihydro-benzo[1,4]dioxin-6-yl, 3-oxo-3,4-dihydro-2H-benzo[1,4]oxazin-6-yl, 3-oxo-3,4-dihydro-2H-benzo[1,4]thiazin-6-yl, 7-fluoro-3-oxo-3,4-dihydro-2H-benzo[1,4]thiazin-6-yl, and 3-oxo-3,4-dihydro-2H-pyrido[3,2-b][1,4]oxazin-6-yl.
38) A further embodiment of the invention relates to compounds according to any one of embodiments 1) to 24), wherein G represents a group selected from 2,3-dihydro-benzo[1,4]dioxin-6-yl, 3-oxo-3,4-dihydro-2H-benzo[1,4]oxazin-6-yl, 3-oxo-3,4-dihydro-2H-benzo[1,4]thiazin-6-yl, and 7-fluoro-3-oxo-3,4-dihydro-2H-benzo[1,4]thiazin-6-yl (notably from 2,3-dihydro-benzo[1,4]dioxin-6-yl, 3-oxo-3,4-dihydro-2H-benzo[1,4]oxazine-6-yl, and 3-oxo-3,4-dihydro-2H-benzo[1,4]thiazine-6-yl).
39) A further embodiment of the invention relates to compounds according to any one of embodiments 1) to 23), wherein G represents phenyl which is mono-substituted in position 3 or 4, or disubstituted in positions 3 and 4; wherein each substituent is independently selected from the group consisting of $(C_1-C_4)$alkyl (notably methyl and ethyl), $(C_1-C_3)$alkoxy, and halogen (notably fluorine).
40) A further embodiment of the invention relates to compounds according to any one of embodiments 1) to 23) or 39), wherein, in case G represents phenyl which is mono-substituted in position 3 or 4, or disubstituted in positions 3 and 4; wherein each substituent is independently selected from the group consisting of $(C_1-C_4)$alkyl (notably methyl and ethyl), $(C_1-C_3)$alkoxy, and halogen (notably fluorine), whereby a $(C_1-C_3)$alkoxy substituent, if present, is a straight chain $(C_1-C_3)$alkoxy group which is attached in position 4.
41) A particular embodiment of this invention relates to the compounds according to one of embodiments 1) to 40) wherein $R^{1b}$ represents H.
42) Another particular embodiment of this invention relates to the compounds according to one of embodiments 1) to 40) wherein $R^{1b}$ represents $(C_1-C_3)$alkyl (in particular methyl).
43) Preferred compounds of Formula (I) as defined in embodiment 1) are selected from the group consisting of:
6-((R)-5-{[3-(7-methoxy-2-oxo-2H-quinolin-1-yl)-propylamino]-methyl}-2-oxo-oxazolidin-3-yl)-4H-benzo[1,4]thiazin-3-one;
6-(R)-5-{[3-(7-bromo-2-oxo-2H-quinolin-1-yl)-propylamino]-methyl}-2-oxo-oxazolidin-3-yl)-4H-benzo[1,4]thiazin-3-one;
1-(3-{[(R)-3-(2,3-dihydro-benzo[1,4]dioxin-6-yl)-2-oxo-oxazolidin-5-ylmethyl]-amino}-propyl)-7-methoxy-1H-quinolin-2-one;
7-bromo-1-(3-{[(R)-3-(2,3-dihydro-benzo[1,4]dioxin-6-yl)-2-oxo-oxazolidin-5-ylmethyl]-amino}-propyl)-1H-quinolin-2-one;
6-(5-{2-[3-(7-methoxy-2-oxo-2H-quinolin-1-yl)-azetidin-1-yl]-ethyl}-2-oxo-oxazolidin-3-yl)-4H-benzo[1,4]thiazin-3-one;
3-(7-methoxy-2-oxo-2H-quinoxalin-1-yl)-N-[(R)-2-oxo-3-(3-oxo-3,4-dihydro-2H-benzo[1,4]thiazin-6-yl)-oxazolidin-5-ylmethyl]-propionamide;
N-[(R)-3-(2,3-dihydro-benzo[1,4]dioxin-6-yl)-2-oxo-oxazolidin-5-ylmethyl]-3-(7-methoxy-2-oxo-2H-quinolin-1-yl)-propionamide;
3-(7-bromo-2-oxo-2H-quinolin-1-yl)-N-[(R)-3-(2,3-dihydro-benzo[1,4]dioxin-6-yl)-2-oxo-oxazolidin-5-ylmethyl]-propionamide;
3-(7-bromo-2-oxo-2H-quinolin-1-yl)-N-[(R)-2-oxo-3-(3-oxo-3,4-dihydro-2H-benzo[1,4]thiazin-6-yl)-oxazolidin-5-ylmethyl]-propionamide;
N-[(R)-3-(2,3-dihydro-benzo[1,4]dioxin-6-yl)-2-oxo-oxazolidin-5-ylmethyl]-3-(7-methoxy-2-oxo-2H-quinoxalin-1-yl)-propionamide;
3-(7-methoxy-2-oxo-2H-quinolin-1-yl)-N-[(R)-2-oxo-3-(3-oxo-3,4-dihydro-2H-benzo[1,4]thiazin-6-yl)-oxazolidin-5-ylmethyl]-propionamide;
(S)-2-amino-N-[(R)-3-(2,3-dihydro-benzo[1,4]dioxin-6-yl)-2-oxo-oxazolidin-5-ylmethyl]-3-(7-methoxy-2-oxo-2H-quinoxalin-1-yl)-propionamide;
(R)-2-amino-N-[(R)-3-(2,3-dihydro-benzo[1,4]dioxin-6-yl)-2-oxo-oxazolidin-5-ylmethyl]-3-(7-methoxy-2-oxo-2H-quinoxalin-1-yl)-propionamide;
6-((R)-5-{[(R)-2-hydroxy-3-(7-methoxy-2-oxo-2H-quinolin-1-yl)-propylamino]-methyl}-2-oxo-oxazolidin-3-yl)-4H-benzo[1,4]oxazin-3-one;
6-((R)-5-{[(R)-2-hydroxy-3-(7-methoxy-2-oxo-2H-quinolin-1-yl)-propylamino]-methyl}-2-oxo-oxazolidin-3-yl)-4H-benzo[1,4]thiazin-3-one; and
6-((R)-5-{[(S)-2-hydroxy-3-(7-methoxy-2-oxo-2H-quinolin-1-yl)-propylamino]-methyl}-2-oxo-oxazolidin-3-yl)-4H-benzo[1,4]thiazin-3-one;
wherein the compound 6-(5-{2-[3-(7-methoxy-2-oxo-2H-quinolin-1-yl)-azetidin-1-yl]-ethyl}-2-oxo-oxazolidin-3-yl)-4H-benzo[1,4]thiazin-3-one may be (R) or (S) configurated.
44) In addition to the compounds listed in embodiment 43), further preferred compounds of Formula (I) as defined in embodiment 1) are selected from the group consisting of:
7-fluoro-6-((R)-5-{[(S)-2-hydroxy-3-(7-methoxy-2-oxo-2H-quinolin-1-yl)-propylamino]-methyl}-2-oxo-oxazolidin-3-yl)-4H-benzo[1,4]thiazin-3-one;
6-methoxy-4-(3-{[(R)-2-oxo-3-(3-oxo-3,4-dihydro-2H-benzo[1,4]thiazin-6-yl)-oxazolidin-5-ylmethyl]-amino}-propyl)-4H-pyrido[2,3-b]pyrazin-3-one;
4-(3-{[(R)-3-(2,3-dihydro-benzo[1,4]dioxin-6-yl)-2-oxo-oxazolidin-5-ylmethyl]-amino}-propyl)-6-methoxy-4H-pyrido[2,3-b]pyrazin-3-one;
6-methoxy-4-(3-{[(R)-2-oxo-3-(3-oxo-3,4-dihydro-2H-benzo[1,4]oxazin-6-yl)-oxazolidin-5-ylmethyl]-amino}-propyl)-4H-pyrido[2,3-b]pyrazin-3-one;
6-methoxy-4-(2-{2-[(R)-2-oxo-3-(3-oxo-3,4-dihydro-2H-benzo[1,4]thiazin-6-yl)-oxazolidin-5-yl]-ethylamino}-ethyl)-4H-pyrido[2,3-b]pyrazin-3-one;
6-methoxy-4-(2-{2-[(R)-2-oxo-3-(3-oxo-3,4-dihydro-2H-benzo[1,4]oxazin-6-yl)-oxazolidin-5-yl]-ethylamino}-ethyl)-4H-pyrido[2,3-b]pyrazin-3-one;
6-methoxy-4-(1-{2-[(R)-2-oxo-3-(3-oxo-3,4-dihydro-2H-benzo[1,4]thiazin-6-yl)-oxazolidin-5-yl]-ethyl}-azetidin-3-yl)-4H-pyrido[2,3-b]pyrazin-3-one;

6-methoxy-4-(1-{3-[(R)-2-oxo-3-(3-oxo-3,4-dihydro-2H-benzo[1,4]thiazin-6-yl)-oxazolidin-5-yl]-propyl}-azetidin-3-yl)-4H-pyrido[2,3-b]pyrazin-3-one;

6-methoxy-4-(1-{2-[(S)-2-oxo-3-(3-oxo-3,4-dihydro-2H-benzo[1,4]thiazin-6-yl)-oxazolidin-5-yl]-ethyl}-azetidin-3-yl)-4H-pyrido[2,3-b]pyrazin-3-one;

4-((R)-2-hydroxy-3-{[(R)-2-oxo-3-(3-oxo-3,4-dihydro-2H-benzo[1,4]thiazin-6-yl)-oxazolidin-5-ylmethyl]-amino}-propyl)-6-methoxy-4H-pyrido[2,3-b]pyrazin-3-one;

4-((R)-3-{[(R)-3-(2,3-dihydro-benzo[1,4]dioxin-6-yl)-2-oxo-oxazolidin-5-ylmethyl]-amino}-2-hydroxy-propyl)-6-methoxy-4H-pyrido[2,3-b]pyrazin-3-one;

4-((R)-2-hydroxy-3-{[(R)-2-oxo-3-(3-oxo-3,4-dihydro-2H-benzo[1,4]oxazin-6-yl)-oxazolidin-5-ylmethyl]-amino}-propyl)-6-methoxy-4H-pyrido[2,3-b]pyrazin-3-one; and 1-(3-{[(R)-3-(2,3-dihydro-benzo[1,4]dioxin-6-yl)-2-oxo-oxazolidin-5-ylmethyl]-amino}-propyl)-7-methoxy-3,4-dihydro-1H-quinolin-2-one.

45) In addition to the compounds listed in embodiments 43) and 44), further preferred compounds of Formula (I) as defined in embodiment 1) are selected from the group consisting of:

4-(3-{[(R)-3-(3-fluoro-4-methyl-phenyl)-2-oxo-oxazolidin-5-ylmethyl]-amino}-propyl)-6-methoxy-4H-pyrido[2,3-b]pyrazin-3-one;

6-methoxy-4-{1-[(R)-2-oxo-3-(3-oxo-3,4-dihydro-2H-benzo[1,4]thiazin-6-yl)-oxazolidin-5-ylmethyl]-azetidin-3-yl}-4H-pyrido[2,3-b]pyrazin-3-one;

4-(2-{2-[3-(2,3-dihydro-[1,4]dioxino[2,3-c]pyridin-7-yl)-2-oxo-oxazolidin-5-yl]-ethylamino}-ethyl)-6-methoxy-4H-pyrido[2,3-b]pyrazin-3-one;

4-(2-{2-[3-(2,3-dihydro-[1,4]dioxino[2,3-b]pyridin-6-yl)-2-oxo-oxazolidin-5-yl]-ethylamino}-ethyl)-6-methoxy-4H-pyrido[2,3-b]pyrazin-3-one;

6-(5-{2-[2-(6-methoxy-3-oxo-3H-pyrido[2,3-b]pyrazin-4-yl)-ethylamino]ethyl}-2-oxo-oxazolidin-3-yl)-4H-pyrido[3,2-b][1,4]oxazin-3-one;

4-(1-{2-[(R)-3-(4-ethoxy-phenyl)-2-oxo-oxazolidin-5-yl]-ethyl}-azetidin-3-yl)-6-methoxy-4H-pyrido[2,3-b]pyrazin-3-one; and 6-methoxy-2-methyl-4-(3-{[(R)-2-oxo-3-(3-oxo-3,4-dihydro-2H-benzo[1,4]thiazin-6-yl)-oxazolidin-5-ylmethyl]-amino}-propyl)-4H-pyrido[2,3-b]pyrazin-3-one.

46) The invention further relates to compounds of Formula (I) according to embodiment 1) which are also compounds of formula ($I_{P1}$)

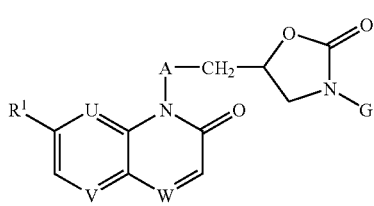

Formula ($I_{P1}$)

wherein $R^1$ represents ($C_1$-$C_4$)alkoxy or halogen;

U represents CH or N;

V represents CH;

W represents CH or N;

A represents —$CH_2$—CH($R^2$)-B-NH—* or —CH($R^3$)—$CH_2$—N($R^4$)—$CH_2$—*; wherein the asterisks indicate the bond which is linked via the $CH_2$-group to the oxazolidinone moiety;

$R^2$ represents hydrogen, OH or $NH_2$;

$R^3$ and $R^4$ together represent $CH_2$;

B represents $CH_2$ or CO; and

G represents 6,7-dihydro-[1,4]dioxino[2,3-c]pyridazin-3-yl; or

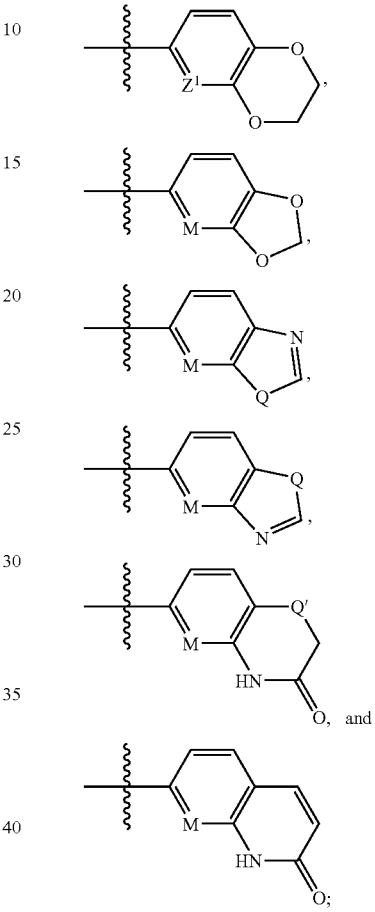

wherein

M and $Z^r$ represent CH or N; and and Q' independently represent S or O;

wherein the preferences or embodiments indicated for the compounds of Formula (I) (whether for the compounds themselves, salts thereof, compositions containing the compounds or salts thereof, uses of the compounds or salts thereof, etc.) apply mutatis mutandis to compounds of formula ($I_P$).

47) A particular embodiment of this invention relates to compounds of Formula (I) as defined in embodiment 1) except that $R^{1b}$ represents H and m, if present, represents 1 or 2; as well as to the salts, especially the pharmaceutically acceptable salts, of the compounds of Formula (I). The preferences and embodiments mentioned for the compounds of Formula (I) in embodiments 2) to 40) apply mutatis mutandis to the present embodiment.

48) The invention further relates to compounds of Formula (I) according to embodiment 47) which are also compounds of formula ($I_{CEP2}$)

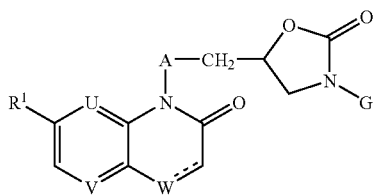

Formula ($I_{CEP2}$)

wherein
$R^1$ represents ($C_1$-$C_4$)alkoxy (especially methoxy) or halogen (especially bromine);
"-----" is absent, U, and V each represent CH, and W represents CH); or
"-----" is a bond; and
U, V and W each represent CH; or U and V each represent CH and W represents N; or U and W each represent N and V represents CH;
A represents —$CH_2$—$CH(R^2)$-B-NH—* or —$CH(R^3)$—$CH_2$—$N(R^4)$—$[CH_2]_m$—*; wherein the asterisks indicate the bond which is linked via the $CH_2$-group to the oxazolidinone moiety;
B represents $CH_2$ or CO; and
$R^2$ represents hydrogen, OH or $NH_2$;
$R^3$ and $R^4$ both represent hydrogen and m represents the integer 1; or $R^3$ and $R^4$ together form a methylene bridge and m represents the integer 1 or 2; and
G represents a group selected from the group consisting of 2,3-dihydro-benzo[1,4]dioxin-6-yl, 3-oxo-3,4-dihydro-2H-benzo[1,4]oxazin-6-yl, 3-oxo-3,4-dihydro-2H-benzo[1,4]thiazin-6-yl, and 7-fluoro-3-oxo-3,4-dihydro-2H-benzo[1,4]thiazin-6-yl;
wherein the preferences or embodiments indicated for the compounds of Formula (I) in embodiments 2) to 40) (whether for the compounds themselves, salts thereof, compositions containing the compounds or salts thereof, uses of the compounds or salts thereof, etc.) apply mutatis mutandis to compounds of formula ($I_{CEP2}$).

49) The invention also relates to compounds of Formula (I) as defined in embodiment 1) which are also compounds of formula ($I_{CE}$)

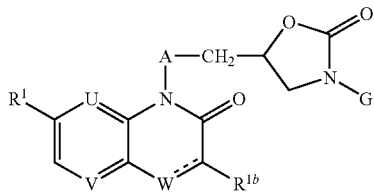

Formula ($I_{CE}$)

wherein
$R^1$ represents ($C_1$-$C_4$)alkoxy (especially methoxy) or halogen (especially bromine);
"-----" is absent, U, and V each represent CH, and W represents $CH_2$; or
"-----" is a bond; and
U, V and W each represent CH; or U and V each represent CH and W represents N; or U and W each represent N and V represents CH;
A represents —$CH_2$—$CH(R^2)$-B-NR—* or —$CH(R^3)$—$CH_2$—$N(R^4)$—$[CH_2]_m$—*; wherein the asterisks indicate the bond which is linked via the $CH_2$-group to the oxazolidinone moiety;
B represents $CH_2$ or CO; and
$R^2$ represents hydrogen, OH or $NH_2$;
$R^3$ and $R^4$ both represent hydrogen and m represents the integer 1; or $R^3$ and $R^4$ together form a methylene bridge and m represents the integer 1 or 2; and
G represents phenyl which is mono-substituted in position 3 by ($C_1$-$C_3$)alkoxy (notably ethoxy), or G represents phenyl which is disubstituted in positions 3 and 4, whereby one of the two substituents is halogen (notably fluorine) and the other is ($C_1$-$C_4$)alkyl (notably methyl); or also
G represents a group selected from the group consisting of the groups $G^1$, and $G^5$ drawn below:

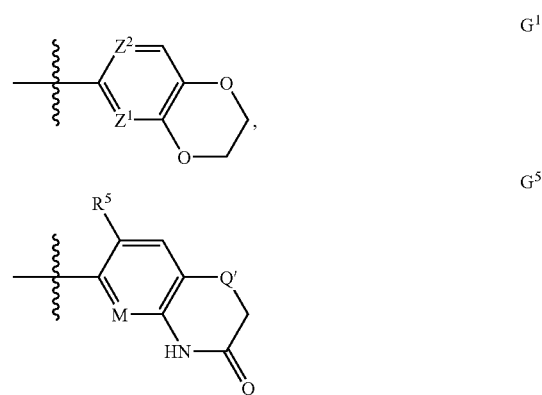

wherein
each of $Z^1$ and $Z^2$ represents CH, or one of $Z^1$ and $Z^2$ represents N and the other represents CH;
M represents CH or N;
Q and Q' independently represent S or O;
$R^5$ represents hydrogen or fluorine;
wherein the preferences or embodiments indicated for the compounds of Formula (I) in embodiments 2) to 42) (whether for the compounds themselves, salts thereof, compositions containing the compounds or salts thereof, uses of the compounds or salts thereof, etc.) apply mutatis mutandis to compounds of formula ($I_{CE}$).

50) The invention further relates to compounds of Formula (I) as defined in embodiment 1), embodiment 2), embodiment 3) or embodiment 49) wherein G represents a group selected from the group consisting of 3-fluoro-4-methyl-phenyl, 4-ethoxy-phenyl, 2,3-dihydro-benzo[1,4]dioxin-6-yl, 2,3-dihydro-[1,4]dioxino[2,3-c]pyridin-7-yl, 2,3-dihydro-[1,4]dioxino[2,3-b]pyridin-6-yl, 3-oxo-3,4-dihydro-2H-benzo[1,4]oxazin-6-yl, 3-oxo-3,4-dihydro-2H-pyrido[3,2-b][1,4]oxazine-6-yl, 3-oxo-3,4-dihydro-2H-benzo[1,4]thiazin-6-yl and 7-fluoro-3-oxo-3,4-dihydro-2H-benzo[1,4]thiazin-6-yl.

The compounds of Formula (I) according to one of embodiments 1) to 50) may contain one or more stereogenic or asymmetric centers, such as one or more asymmetric carbon atoms. The compounds of Formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases or the like, this is intended to mean also a single compound, salt, disease or the like.

The compounds of Formula (I) according to one of embodiments 1) to 50) are suitable for the use as chemotherapeutic active compounds in human and veterinary medicine and as substances for preserving inorganic and organic materials in particular all types of organic materials for example polymers, lubricants, paints, fibres, leather, paper and wood.

These compounds according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C—F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of Formula (I) according to one of embodiments 1) to 50 are further useful for the preparation of a medicament for the treatment of infections that are mediated by bacteria such as *E. coli, Klebsiella pneumoniae* and other Enterobacteriaceae, *Acinetobacter* spp., *Stenothrophomonas maltophilia, Neisseria meningitidis, Bacillus cereus, Bacillus anthracis, Clostridium difficile, Corynebacterium* spp., *Propionibacterium acnes* and *bacteroides* spp.

The compounds of Formula (I) according to one of embodiments 1) to 50 are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

The compounds of Formula (I) according to one of embodiments 1) to 50), or the pharmaceutically acceptable salts thereof, may be used for the preparation of a medicament, and are suitable, for the prevention or treatment of a bacterial infection.

One aspect of this invention therefore relates to the use of a compound of Formula (I) according to one of embodiments 1) to 50), or of a pharmaceutically acceptable salt thereof, for the manufacture of a medicament for the prevention or treatment of a bacterial infection. Another aspect of this invention relates to a compound of Formula (I) according to one of embodiments 1) to 50), or of a pharmaceutically acceptable salt thereof, for the prevention or treatment of a bacterial infection.

Accordingly, the compounds of Formula (I) according to one of embodiments 1) to 50), or the pharmaceutically acceptable salts thereof, may be used for the preparation of a medicament, and are suitable, for the prevention or treatment of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium difficile* infections, urinary tract infections, sexually transmitted infections, foreign body infections, osteomyelitis, lyme disease, topical infections, opthalmological infections, tuberculosis and tropical diseases (e.g. malaria), and notably for the prevention or treatment of a bacterial infection selected from the group consisting of respiratory tract infections, otitis media, meningitis, skin and soft tissue infections (whether complicated or uncomplicated), pneumonia (including hospital acquired pneumonia) and bacteremia.

As well as in humans, bacterial infections can also be treated using compounds of Formula (I) according to one of embodiments 1) to 50) (or pharmaceutically acceptable salts thereof) in other species like pigs, ruminants, horses, dogs, cats and poultry.

The present invention also relates to pharmacologically acceptable salts and to compositions and formulations of compounds of Formula (I) according to one of embodiments 1) to 50).

Any reference to a compound of Formula (I) according to one of embodiments 1) to 50) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

A pharmaceutical composition according to the present invention contains at least one compound of Formula (I) according to one of embodiments 1) to 50) (or a pharmaceutically acceptable salt thereof) as the active agent and optionally carriers and/or diluents and/or adjuvants, and may also contain additional known antibiotics.

As mentioned above, therapeutically useful agents that contain compounds of Formula (I) according to one of embodiments 1) to 50), their salts and formulations thereof are also comprised in the scope of the present invention.

The compounds of Formula (I) according to one of embodiments 1) to 50) and their pharmaceutically acceptable salts can be used as medicaments, e.g. in the form of pharmaceutical compositions for enteral or parental administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient comprising the administration to said patient of a pharmaceutically active amount of a compound according to Formula (I) according to one of embodiments 1) to 50), or a pharmaceutically acceptable salt thereof.

Moreover, the compounds of Formula (I) according to one of embodiments 1) to 50) may also be used for cleaning purposes, e.g. to remove pathogenic microbes and bacteria from surgical instruments or to make a room or an area aseptic. For such purposes, the compounds of Formula (I) could be contained in a solution or in a spray formulation.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

Preparation of Compounds of Formula (I)

Abbreviations

The following abbreviations are used throughout the specification and the examples:
AcOH acetic acid
AD-mix α 1,4-bis(dihydroquinine)phthalazine, $K_3Fe(CN)_6$, $K_2CO_3$ and $K_2OsO_4.2H_2O$
AD-mix β 1,4-bis(dihydroquinidine)phthalazine, $K_3Fe(CN)_6$, $K_2CO_3$ and $K_2OsO_4.2H_2O$
aq. aqueous
Boc tert-butoxycarbonyl-
n-BuLi n-butyl lithium
t-BuOH tent-butanol
Cbz benzyloxycarbonyl-
CDI 1,1'-carbonyldiimidazole
d day(s)
DCM dichloromethane
DCC N,N'-dicyclohexylcarbodiimide
DCE 1,2-dichloroethane
DIBAH diisobutylaluminium hydride
DIPEA N,N-diisopropylethylamine
DMAP 4-dimethylaminopyridine
DMF N,N-dimethylformamide
DMSO dimethylsulfoxide
DPEphos bis(2-diphenylphosphinophenyl)ether
DPPA diphenyl phosphoryl azide
EA ethyl acetate
EDC 1-(3-dimethylaminopropyl)-3-ethylcarbodiimide hydrochloride
eq. equivalent(s)
ESI Electron Spray Ionisation
Et ethyl
ether diethyl ether
EtOH ethanol
$Et_3SiH$ triethylsilane
CC column chromatography over silica gel
h hour(s)
HATU (O-(7-azabenzotriazol-1-yl)-1,1,3,3-tetramethyl-uronium hexafluorphoshate
Hept heptane
hex hexane
HOBT hydroxybenzotriazole
KHMDS potassium bis(trimethylsilyl)amide
LiOtBu lithium tert-butoxide
Me methyl
MeCN acetonitrile
MeOH methanol
min minutes
Ms methanesulfonyl-(mesyl-) (as in MsCl: methanesulfonyl chloride)
MS Mass Spectroscopy
$Ms_2O$ methansulfonic acid anhydride
$NaBH(OAc)_3$ sodium triacetoxyborohydride
NaOMe sodium methylate
NMO N-methylmorpholine N-oxide
OAc acetate
org. organic
Pd/C palladium on carbon
$Pd(OH)_2$/C palladium dihydroxide on carbon
$PPh_3$ triphenylphosphine
Pyr pyridine
quant. quantitative
Rochelles salt potassium sodium tartrate
rt room temperature
sat. saturated
TBAF tetrabutylammonium fluoride
TBDMS tert-butyldimethylsilyl-
TBDPS tert-butyldiphenylsilyl-
TBME tert-butylmethyl ether
TEA triethylamine
TEMPO 2,2,4,4-tetramethylpiperidine 1-oxyl
Tf trifluoromethanesulfonyl-(as in TfCl: trifluoromethanesulfonyl chloride)
$Tf_2O$ trifluoromethanesulfonic acid anhydride
TFA trifluoroacetic acid
THF tetrahydrofuran
Ts p-toluenesulfonyl-(tosyl-) (as in p-TsCl: p-toluenesulfonyl chloride)

General Synthetic Methods:

General Synthetic Method 1: Activation of an Alcohol:

The alcohol derivative is reacted with MsCl, TfCl, TsCl in presence of an organic base such as TEA, DIPEA or pyridine in a solvent such as DCM, THF or pyridine between −10° C. and 25° C. Alternatively the alcohol can also be reacted with $Ms_2O$ or $Tf_2O$. The activated intermediate can be further transformed into its corresponding iodo or bromo derivative by reaction of the activated alcohol with NaI or NaBr in a solvent such as acetone.

General Synthetic Method 2: Alkylation:

The amine derivative is reacted with a compound of formula alkyl-$L^1$, VI, XII or XIV wherein $L^1$, $L^2$ and $L^3$ represent OMs, OTf, OTs, Cl, Br or I in presence of an inorganic base such as K$_2$CO$_3$, CsCO$_3$ or an organic base such as TEA in a solvent such as THF, DMF or DMSO, between 0° C. and +80° C. Further details can be found in *Comprehensive Organic Transformations. A guide to Functional Group Preparations; 2$^{nd}$* Edition, R. C. Larock, Wiley-VC; New York, Chichester, Weinheim, Brisbane, Singapore, Toronto, (1999). Section Amines p. 779.

General Synthetic Method 3: Reductive Amination:

A solution of primary amine (1 mmol) and aldehyde or ketone (1 mmol) in DCE/MeOH 1:1 (10 mL) is stirred at rt overnight. NaBH$_4$ (2-5 eq.) is added and the reaction allowed to proceed for another one hour. The reaction is diluted with DCM and aq. NH$_4$OH. The org. phase is washed with water, dried over MgSO$_4$ and concentrated. Alternatively, a solution of secondary amine (1 mmol) and aldehyde or ketone (1 mmol) in DCE/MeOH 1:1 (10 mL) is treated with NaBH (OAc)$_3$ (2 eq). The mixture is stirred at rt until complete conversion. The reaction is diluted with DCM and aq. NH$_4$OH. The org. phase is washed with water, dried over MgSO$_4$ and concentrated.

General Synthetic Method 4: Amide Coupling:

The carboxylic acid is reacted with the amine in presence of an activating agent such as DCC, EDC, HOBT, n-propylphosphonic cyclic anhydride, HATU or di-(N-succinimidyl)-carbonate, in a dry aprotic solvent such as DCM, MeCN or DMF between −20° C. and +60° C. (see G. Benz in *Comprehensive Organic Synthesis*, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between −20° and +60° C. Further activating agents can be found in *Comprehensive Organic Transformations. A guide to Functional Group Preparations; 2$^{nd}$* Edition, R. C. Larock, Wiley-VC; New York, Chichester, Weinheim, Brisbane, Singapore, Toronto, 1999. Section nitriles, carboxylic acids and derivatives p. 1941-1949.

General Synthetic Method 5: Cis-Dihydroxylation:

The diol is obtained by dihydroxylation of the corresponding ethylenic derivative using a catalytic amount of osmium tetroxide in the presence a co-oxidant such as NMO in aq. solvent such as an acetone-water or DCM-water mixture (see Cha, J. K. *Chem. Rev.* 1995, 95, 1761-1795). The chiral cis-diols are obtained by using AD-mix α or AD-mix β in presence of methanesulfonamide in a water/2-methyl-2-propanol mixture as described in *Chem. Rev.* (1994), 94, 2483. The sense of induction relies on the chiral ligand contained in the AD mixture, either a dihydroquinine-based ligand in AD-mix α or a dihydroquinidine-based ligand in AD-mix β.

General Synthetic Method 6: Alcohols Through Ester Reduction:

The ester is reduced with a boron or aluminum hydride reducing agent such as LiBH$_4$ or LiAlH$_4$ in a solvent such as THF between −20° C. and 40° C. Alternatively, the ester function is hydrolyzed into its corresponding acid using an alkali hydroxide such as NaOH, KOH or LiOH in water or in a mixture of water with polar protic or aprotic organic solvent such as THF or MeOH between −10° C. and 50° C. The resulting carboxylic acid is further reduced into the corresponding alcohol using a borane derivative such as a BH$_3$.THF complex in a solvent such as THF between −10° C. and 40° C.

General Synthetic Method 7: Aldehydes Through Ester Reduction:

The ester is reduced with a bulky hydride reagent DIBAH in a solvent such as THF between −20° C. and 40° C.

General Synthetic Method 8: Hydrolysis of Ester into Carboxylic Acids:

When the ester side chain is a linear alkyl, the hydrolysis is usually performed by treatment with an alkali hydroxide such as LiOH, KOH or NaOH in a water-dioxane or water-THF mixture between 0° C. and +80° C. When the ester side chain is tert-butyl, the hydrolysis can also be performed in neat TFA or diluted TFA or HCl in an organic solvent such as ether or THF. When the ester side chain is the allyl group, the reaction is performed in presence of tetrakis(triphenylphosphine)palladium(0) in presence of an Π-allyl cation scavenger such as morpholine, dimedone or tributyltin hydride between 0° C. and +50° C. in a solvent such as THF. When the ester side chain is benzyl, the reaction is performed under hydrogen in presence of a noble metal catalyst such as Pd/C in a solvent such as MeOH, THF or EA. Further strategies to introduce other acid protecting groups and general methods to remove them have been described in Protecting Groups in Organic Synthesis 3$^{rd}$ Ed; 1999, 369-441; T. W. Greene, P. G. M. Wuts; (Publisher: John Wiley and Sons, Inc., New York, N.Y.).

General Synthetic Method 9: Amino Deprotection:

The benzyl carbamates are deprotected by hydrogenolysis over a noble catalyst (e.g. Pd/C or Pd(OH)$_2$/C). The Boc group is removed under acidic conditions such as HCl in an organic solvent such as MeOH or dioxane, or TFA neat or diluted in a solvent such DCM. Further general methods to remove amine protecting groups have been described in *Protecting Groups in Organic Synthesis,* 3$^{rd}$ Ed (1999), 494-653; T. W. Greene, P. G. M. Wuts; (Publisher: John Wiley and Sons, Inc., New York, N.Y.).

General Synthetic Method 10: Hydroxy Deprotection:

The silyl ether groups are removed either using fluoride anion sources such as TBAF in THF between 0° C. and +40° C. or HF in MeCN between 0° C. and +40° C. or using acidic conditions such as AcOH in THF/MeOH or HCl in MeOH. Further methods to remove the TBDMS and TBDPS groups are given in Protecting Groups in Organic Synthesis 3$^{rd}$ Ed; 1999, 133-139 and 142-143 respectively; T. W. Greene, P. G. M. Wuts; (Publisher: John Wiley and Sons, Inc., New York, N.Y.). Further general methods to remove alcohol protecting groups are described in Protecting Groups in Organic Synthesis 3$^{rd}$ Ed; 1999, 23-147; T. W. Greene, P. G. M. Wuts; (Publisher: John Wiley and Sons, Inc., New York, N.Y.).

General Synthetic Method 11: Reduction of Azides into Amines:

The azides are hydrogenated over a noble metal catalyst such as Pd/C in solvent such as MeOH or EA. In case the molecule is containing an unsaturated double or triple bond, the reduction can be performed using PPh$_3$ in presence of water as described in *J. Med. Chem.* (1993), 36, 2558-68.

General Synthetic Method 12: Ketal Deprotection:

The ketal is converted into its corresponding ketone under acidic conditions such as diluted aq. HCl in MeOH, diluted aq. AcOH or by using an acidic resin such as Amberlite IR120H or DOWEX 50W8 in a water-solvent mixture such as MeOH/water or THF/water.

The compounds of Formula (I) obtained according to the abovementioned general preparation methods may then, if desired, be converted into their salts, and notably into their pharmaceutically acceptable salts. Whenever the compounds of Formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as TEA, diethylamine) and eluent B (hex), at a flow rate of 0.8 to 150 mL/min.

General Synthetic Method 13: Oxidation of Alcohols/Aldehydes into Acids:

Alcohols can be directly oxidized into their corresponding acids by a variety of methods as described in *Comprehensive Organic Transformations. A guide to Functional Group Preparations;* 2$^{nd}$ Edition, R. C. Larock, Wiley-VC; New York, Chichester, Weinheim, Brisbane, Singapore, Toronto, 1999. Section nitriles, carboxylic acids and derivatives p. 1646-1648. Among them, [bis(acetoxy)iodo]benzene in presence of TEMPO, the Jones reagents ($CrO_3/H_2SO_4$), $NaIO_4$ in presence of $RuCl_3$, $KMnO_4$ or $Pyr.H_2Cr_2O_7$ are frequently used.

Aldehydes can be oxidized into their corresponding acids by a variety of methods as described in *Comprehensive Organic Transformations. A guide to Functional Group Preparations;* 2$^{nd}$ Edition, R. C. Larock, Wiley-VC; New York, Chichester, Weinheim, Brisbane, Singapore, Toronto, 1999. Section nitriles, carboxylic acids and derivatives p. 1653-1655. Among them, $KMnO_4$ in an acetone-water mixture (see *Synthesis* (1987), 85) or sodium chlorite in 2-methyl-2-propanol in presence of 2-methyl-2-butene (see *Tetrahedron* (1981), 37, 2091-2096) are frequently used.

General Synthetic Method 14: Protection of Alcohols:

The alcohols are protected as silyl ethers (usually TBDMS or TBDPS ethers). The alcohol is reacted with the required silyl chloride reagent (TBDMSCl or TBDPSCl) in presence of a base such as imidazole or TEA in a solvent such as DCM or DMF between +10° C. and +40° C. Further strategies to introduce other alcohol protecting groups have been described in, T. W. Greene, P. G. M. Wuts, *Protecting Groups in Organic Synthesis,* 3rd Ed (1999), 23-147 (Publisher: John Wiley and Sons, Inc., New York, N.Y.).

General Synthetic Method 15: (Hydrogenation of a Double Bond):

The unsaturated derivatives dissolved in a solvent such as MeOH, EA or THF are hydrogenated over a noble metal catalyst such as Pd/C or Pd(OH)$_2$/C, or over Raney Ni. At the end of the reaction the catalyst is filtered off and the filtrate is evaporated under reduced pressure. Alternatively the reduction can be performed by catalytic transfer hydrogenation using Pd/C and ammonium formate as hydrogen source.

General Preparation Methods:

Preparation of the Compounds of Formula (I)

The compounds of Formula (I) can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) to h) hereafter describe general methods for preparing compounds of Formula (I). The preparation of elaborated intermediates and basic building blocks is described thereafter. General synthetic methods used repeatedly throughout the schemes below are referenced to and described in the end of this section. If not indicated otherwise, the generic groups and integers U, V, W, $R^1$, $R^2$, $R^3$, $R^4$, A, B, G and m are as defined for Formula (I). Other abbreviations used are defined in the experimental section. In some instances the generic groups $R^1$, $R^2$, $R^3$, $R^4$, A, B, W, and G might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999).

The compounds of Formula (I) can be manufactured in accordance with the present invention using the procedures described hereafter by:

a) reacting the compounds of formula (II)

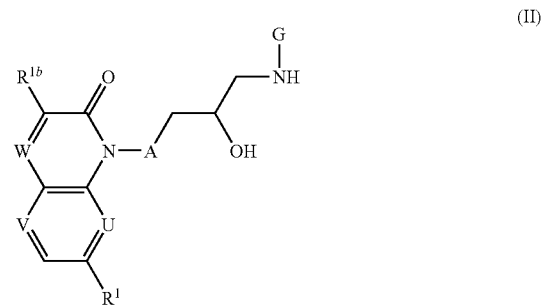

with the carbonic acid derivatives of formula (III),

wherein $L^0$ and $L^{00}$ both represent chloro, $OCCl_3$, imidazolyl or succinimidyloxy, or $L^0$ represents chloro and $L^{00}$ represents $OCCl_3$. This reaction is preferably carried out in a dry aprotic solvent such as DCM or THF in presence of an organic base such as TEA or pyridine and at a temperature range between −30° C. and +80° C.; or b) reacting the compounds of formula (IV)

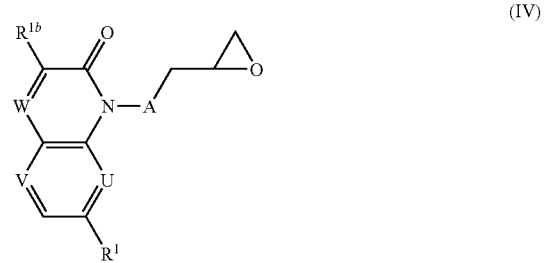

with the anions generated from the compounds of formula (V)

wherein R represents alkyl or benzyl, with a base such as KHMDS or lithium tert-butylate; or c) reacting the compounds of formula (VI)

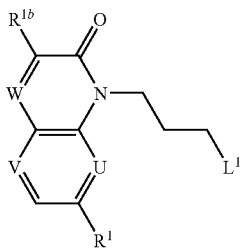
(VI)

wherein $L^1$ represents a halogen such as chlorine or bromine, or a $OSO_2R^a$ group wherein $R^a$ is alkyl, tolyl, or trifluoromethyl with the compounds of formula (VII) following general synthetic method 2

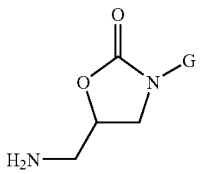
(VII)

or
d) reacting the compounds of formula (VIII)

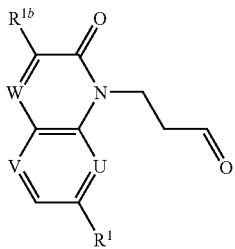
(VIII)

with the compounds of formula (VII) under reductive amination conditions following general synthetic method 3; or e) reacting a compound of formula (IX)

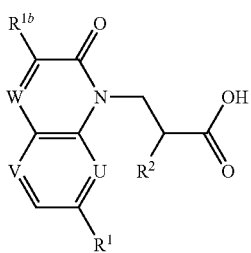
(IX)

wherein $R^2$ is H, OH or NH, with a compound of formula (VII) following general synthetic method 4; or f) reacting the compounds of formula (X) or (XI)

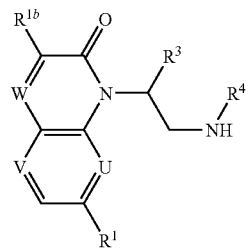
(X)

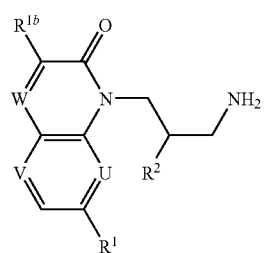
(XI)

with the compounds of formula (XII)

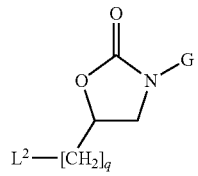
(XII)

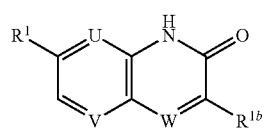

wherein $L^2$ represents a halogen such as iodine or bromine, or a $OSO_2R^a$ group wherein $R^a$ is alkyl, tolyl, or trifluoromethyl and q represents the integer 1, 2 or 3, following general synthetic method 2; or g) reacting the compounds of formula (XIII)

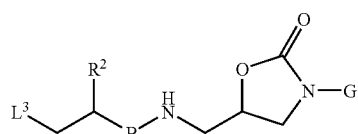
(XIII)

with the compounds of formula (XIV)

(XIV)

wherein $L^3$ represents a halogen such as iodine or bromine, or a $OSO_2R^a$ group wherein $R^a$ is alkyl, tolyl, or trifluoromethyl, following general synthetic method 2; or h) reacting the compounds of formula (XIII) with the compounds of formula (XV)

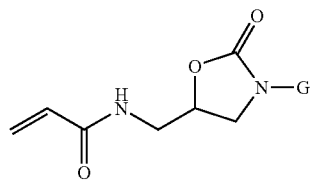
(XV)

in presence of CsF in an organic solvent such as MeCN between 20 and 80° C.; or i) reacting the compounds of formula (XXX)

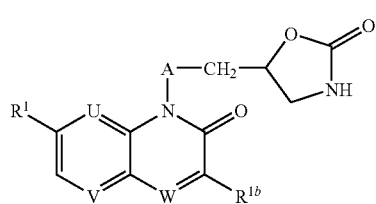
(XXX)

with the compounds of formula (XXXI)

G-X (XXXI)

wherein X represents halogen, whereby, in case of compounds of formula (XXXI) wherein M is N, the reaction can be performed in presence of a NaH and this reaction can also be performed under conditions described for the metal catalyzed N-arylation of 2-oxazolidinones or amides, in particular by using CuI and 1,1,1-tris(hydroxymethyl)ethane in the presence of $Cs_2CO_3$ (*Org. Lett.* 2006, 8, 5609-5612), or $Pd(OAc)_2$ and DPEphos in presence of $K_3PO_4$; or j) deprotecting the compounds of formula (XXXII)

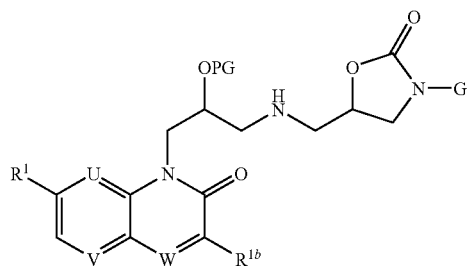
(XXXII)

according to general synthetic method 10; or k) deprotecting the compounds of formula (XXXIII)

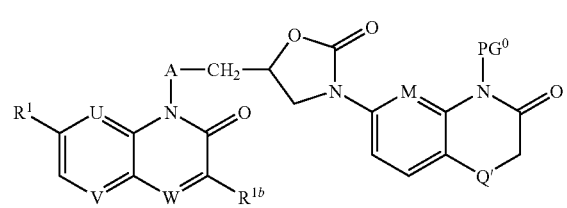
(XXXIII)

wherein M is N or CH, Q' is O or S and $PG^0$ represents a group such as 4-methoxybenzyl, 2,4-dimethoxybenzyl or 3,4-dimethoxybenzyl, whereby said deprotection can be performed by treatment with TFA or cerium ammonium nitrate.

The compounds of Formula (I) wherein "----" is absent can be obtained via hydrogenation of compounds of Formula (I) wherein "----" is a bond over a noble catalyst such as Pd/C (see for example general synthetic method 15) or via reduction of the same using $NaBH_4$ in a solvent such as EtOH. Alternatively, appropriate intermediates described below may be reduced as described above and transformed into the compounds of Formula (I) according to methods a) to k) above.

Preparation of the Compounds of Formula (II)

The compounds of formula (II) can be obtained by reacting the compounds of formula (IV) with the amines of formula (XVI)

$G-NH_2$ (XVI)

Preparation of the Compounds of Formula (IV)

The compounds of formula (IV) can be obtained by cis-dihydroxylation of the compounds of formula (XVII)

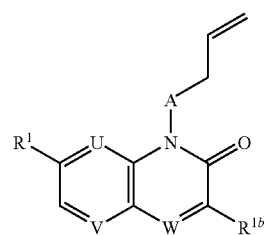
(XVII)

following general synthetic method 5 followed by mesylation or tosylation of the primary alcohol function following general synthetic method 1 and epoxide formation under basic conditions.

The compounds of formula (XVII) can be obtained as described in Scheme 1 hereafter.

Scheme 1

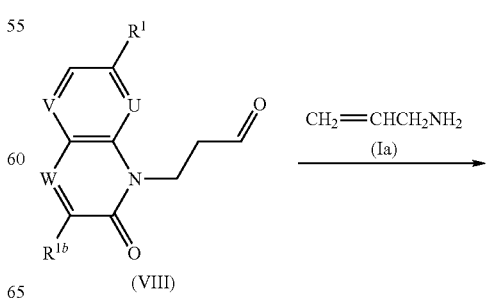
(VIII)

-continued

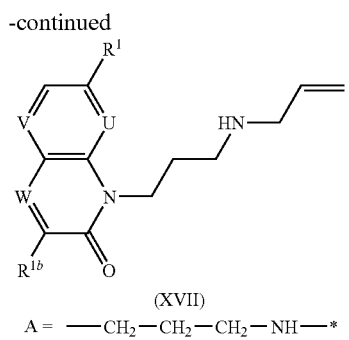

(XVII)
A = —CH$_2$—CH$_2$—CH$_2$—NH—*

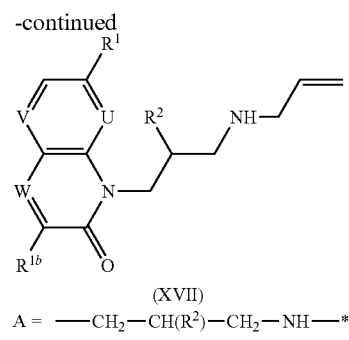

(XVII)
A = —CH$_2$—CH(R$^2$)—CH$_2$—NH—*

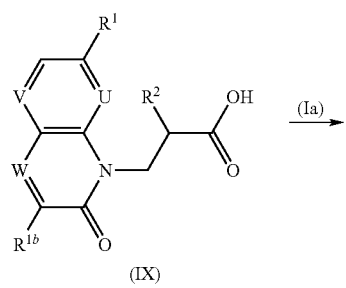

(IX)

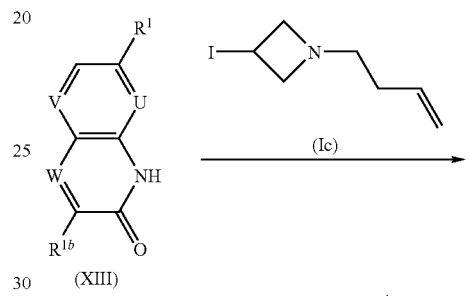

(XIII)

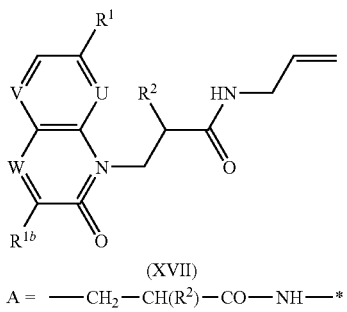

(XVII)
A = —CH$_2$—CH(R$^2$)—CO—NH—*

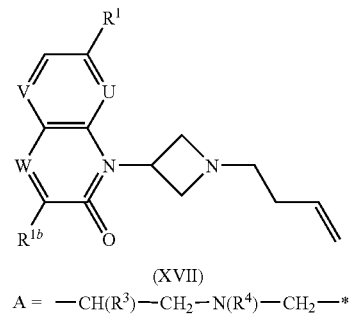

(XVII)
A = —CH(R$^3$)—CH$_2$—N(R$^4$)—CH$_2$—*

The compounds of formula (XVII) wherein A represents —CH$_2$—CH$_2$—CH$_2$—NH—* can be obtained by reductive amination of the aldehydes of formula (VIII) with the allyl amines of formula (Ia) following general synthetic method 3. The compounds of formula (XVII) wherein A represents —CH$_2$—CH(R$^2$)—CO—NH—* can be obtained by amide coupling between the acids of formula (IX) with the allyl amines of formula (Ia) following general synthetic method 4. The compounds of formula (XVII) wherein A represents —CH$_2$—CH(R$^2$)—CH$_2$—NH—* can be obtained by reductive amination of acroleine (Ib) with the amines of formula (XI) following general synthetic method 3. The compounds of formula (XVII) wherein A represents —CH(R$^3$)—CH$_2$—N(R$^4$)—CH$_2$—* and R$^3$ and R$^4$ together form a methylene bridge are obtained by substitution of the compounds of formula (XIII) with the iodo derivative of formula (Ic) following general synthetic method 2. Alternative conditions are NaH, K$_2$CO$_3$ or Ag$_2$CO$_3$ in a solvent such as DMF (see for example *Heteroat. Chem.*, 17, 2006, 280-288, *Bioorg. Med. Chem. Lett.*, 16, 2006, 658-662 or *J. Heterocyel. Chem.*, 42, 2005, 883-888).

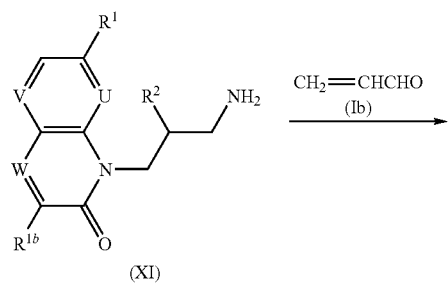

(XI)

Preparation of the Compounds of Formulae (VI), (VIII) and (IX)

The compounds of formulae (VI), (VIII) and (IX) can be obtained according to Scheme 2 hereafter.

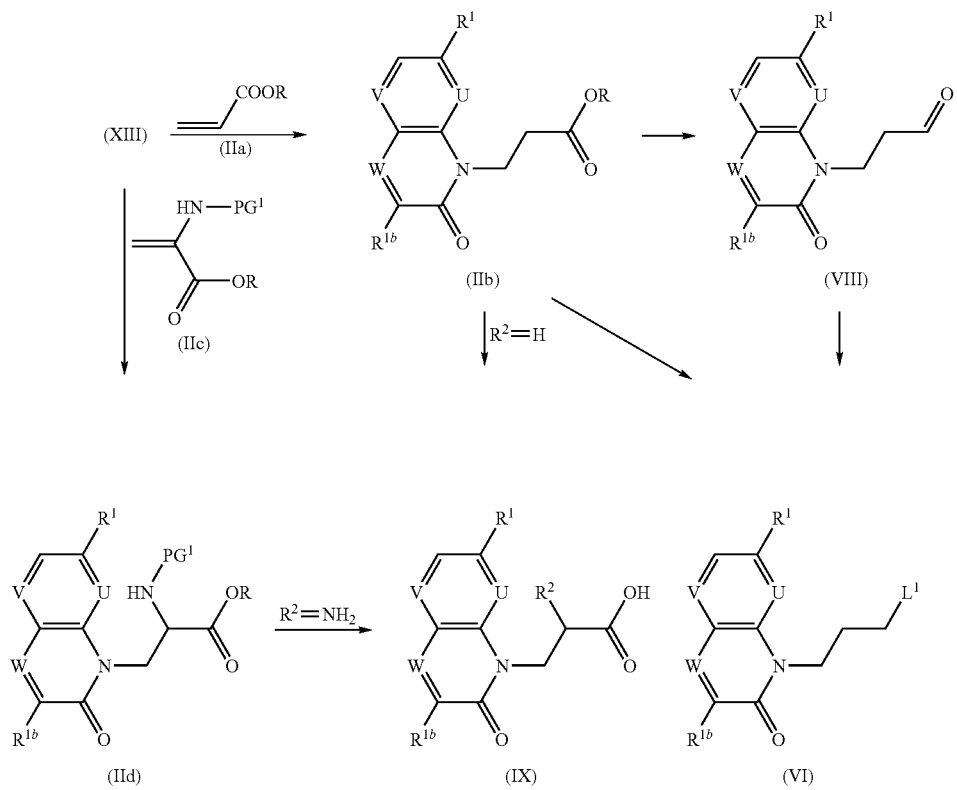

In Scheme 2, R represents alkyl or benzyl, PG represents an amino protecting group such as Cbz or Boc and $L^1$ represents OH, halogen such as bromine or $OSO_2R^a$ wherein $R^a$ is methyl, trifluoromethyl or tolyl.

The compounds of formula (IIb) can be obtained by CsF catalyzed addition of the derivatives of formula (XIII) on the acrylic ester derivatives of formula (IIa). These esters can be reduced into the corresponding alcohols of formula (VI) wherein $L^1$ is OH either directly following general synthetic method 6 or via the aldehydes of formula (VIII). The alcohols of formula (VI) wherein $L^1$ is OH can be transformed into the corresponding mesylates, triflates, tosylates or halogenides ($L^1$=OMs, OTf, OTs, Br, Cl or I) following general synthetic method 1. The compounds of formula (IX) wherein $R^2$ is H can be obtained by hydrolysis of the esters of formula (IIb) following general synthetic method 8. The compounds of formula (IX) wherein $R^2$ is $NH_2$ can be obtained by CsF catalyzed addition of the derivatives of formula (XIII) on the acrylic ester derivatives of formula (IIc), followed by hydrolysis of the corresponding esters into the corresponding carboxylic acids following general synthetic method 8 and removal of the amino protecting group following general synthetic method 9.

In the particular case wherein U and W each represent N, V represents CH and $R^{1b}$ represents methyl, the compounds of formula (VIII) can also be prepared by oxidation of the compounds of formula (VIIIg)

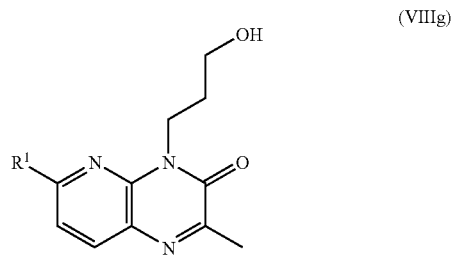

which oxidation can for example be carried out using Swern conditions and the like (e.g. $Pyr.SO_3$ complex in DMSO in the presence of a base such as DIPEA).

Likewise, in the particular case wherein U and W each represent N, V represents CH and $R^{1b}$ represents methyl, the compounds of formula (IX) can also be prepared by ester hydrolysis and, if required, removal of the amino or hydroxy protecting group of the compounds of formula (VIIIf)
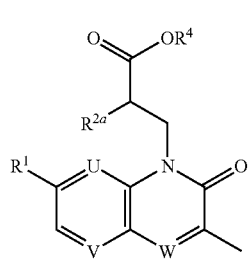
wherein $R^{2a}$ represents H, $NHPG^7$ or $OPG^8$ and $R^4$ represents alkyl or benzyl.
Preparation of the Compounds of Formulae (X) and (XI)
The compounds of formula (X) and (XI) can be prepared as described in Scheme 3 hereafter.
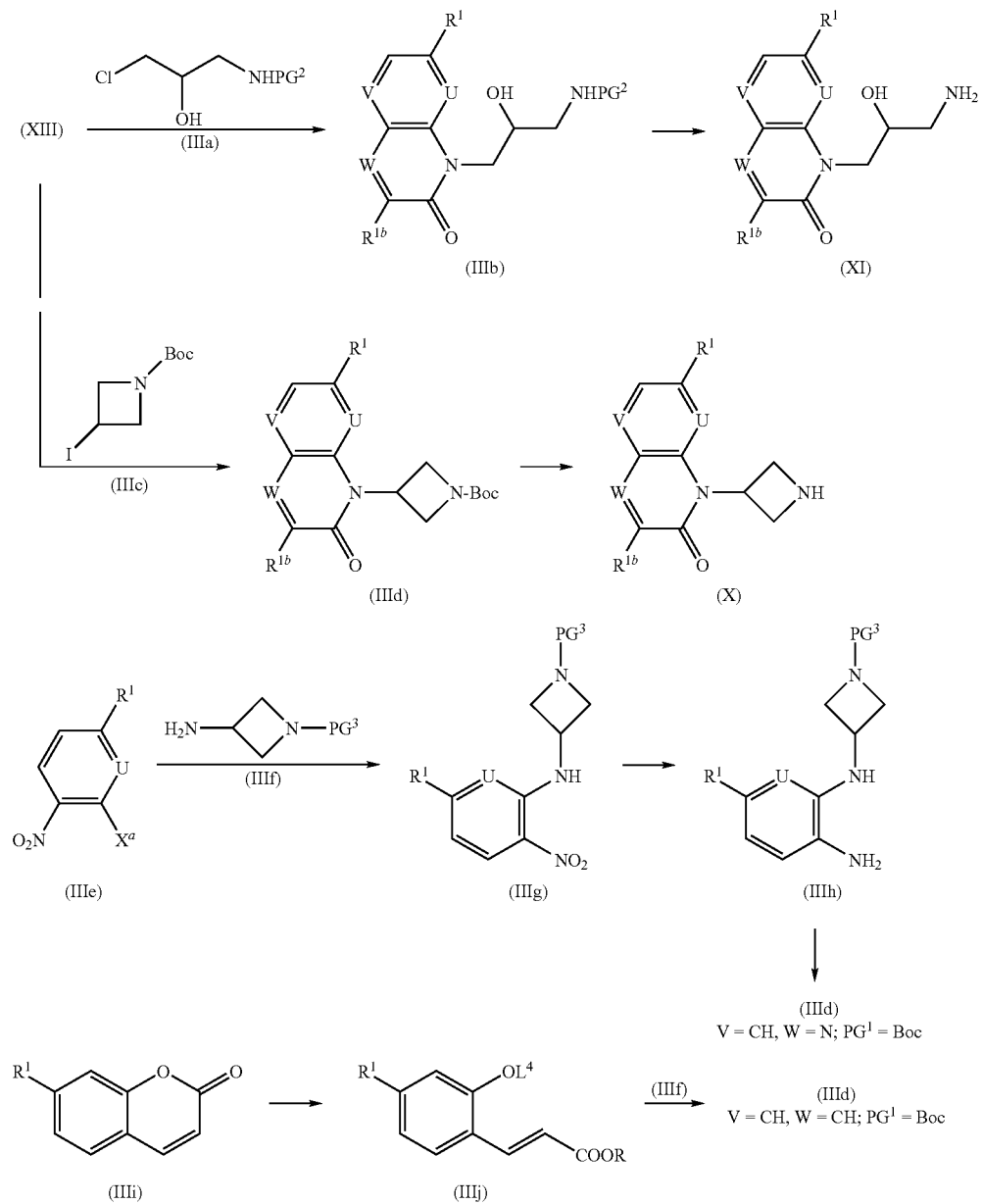

In Scheme 3, $PG^2$ and $PG^3$ represent independently from each other an amino protecting group such as Boc or Cbz, $X^a$ represents a halogen, $L^4$ represents $SO_2CF_3$ and R represents alkyl or benzyl The compounds of formula (XI) can be obtained by reaction of the derivatives of formula (XIII) with the intermediates of formula (IIIa), followed by removal of the amino protecting group of the intermediates of formula (IIIb). The compounds of formula (X) can be obtained by alkylation of the derivatives of formula (XIII) with tert-butyl 3-iodo-1-azetidinecarboxylate (IIIc) following general synthetic method 2, followed by removal of the amino protecting group of the intermediates of formula (IIId) following general synthetic method 9.

Alternatively the compounds of formula (IIId) wherein V is CH and W is N can be obtained from the known nitro derivatives of formula (IIIe) by reaction with known azetidine derivatives of formula (IIIf) in presence of a base such as $K_2CO_3$ between 80 and 150° C. in analogy to U.S. Pat. No. 5,245,037. The nitro derivative is converted into the corresponding amine derivative by reduction (e.g. hydrogenation over Pd/C) followed by reaction with an alkyl glyoxylate. The compounds of formula (IIId) wherein V is CH and W is CH can be obtained from the derivatives of formula (IIIi) after sequential ring opening under basic condition, esterification of the carboxylic acid function and formation of the corresponding triflates of formula (IIIj). These triflates can then be reacted in analogy to *Tetrahedron Letters* (2003), 44(22), 4207-4211 with the azetidine derivatives of formula (IIIf), affording the corresponding derivatives of formula (IIId).

In the particular case wherein U and W each represent N, V represents CH and $R^{1b}$ represents methyl, the compounds of formula (XI) can also be prepared by removal of the protecting group(s) of the compounds of formula (VIIIf')

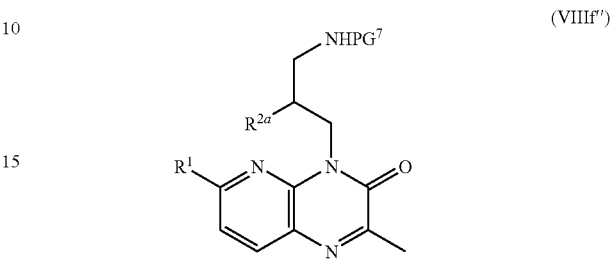

wherein $R^{2a}$ represents H, $NHPG^7$ or $OPG^8$ and $PG^7$ represents an amino protecting group such as Cbz, Fmoc or Boc.

Preparation of the Compounds of Formulae (VII), (XII), (XIV) and (XV)

The compounds of formulae (VII), (XII) (XIV) and (XV) can be prepared according to Scheme 4 hereafter.

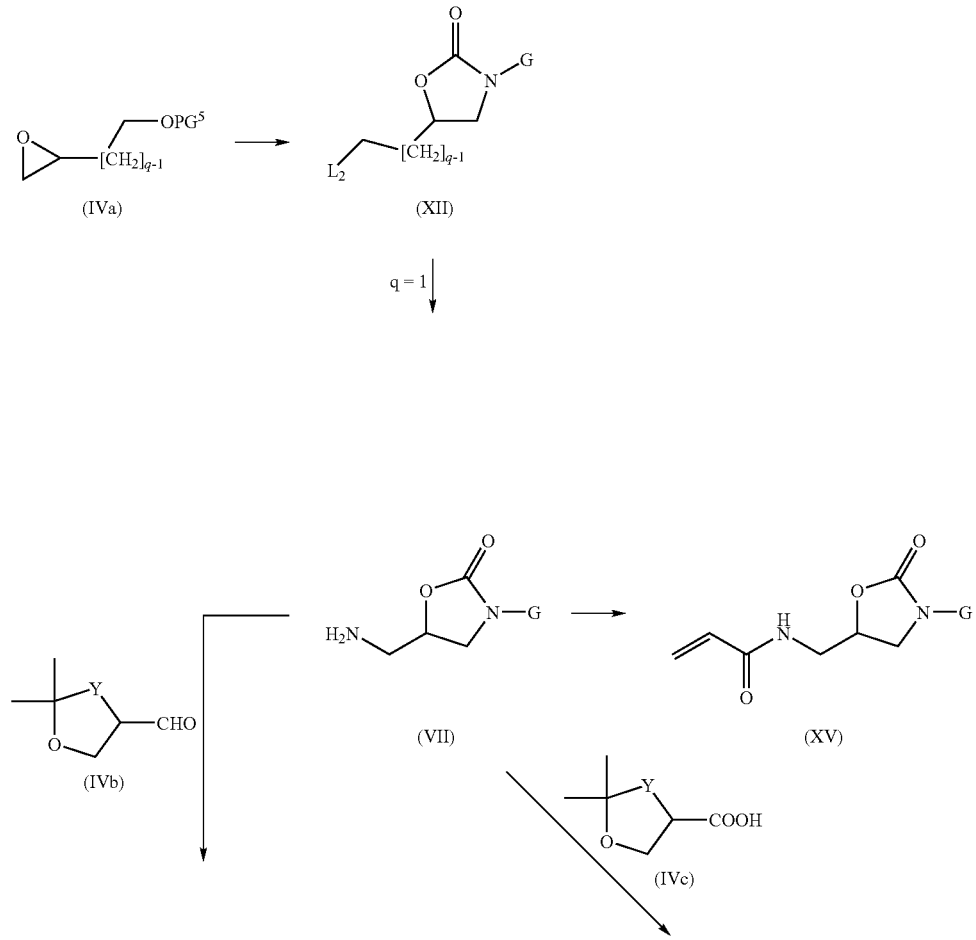

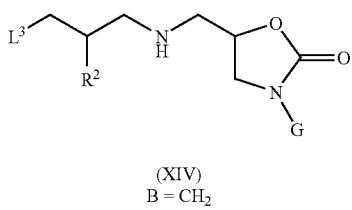

(XIV)
B = CH₂

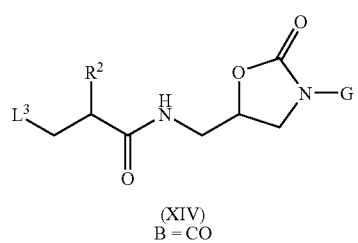

(XIV)
B = CO

In Scheme 4, $PG^5$ represents an alcohol protecting group such as TBDMS, TBDPS; Y represents O or $N-PG^6$; $PG^6$ represents an amino protecting group such as Cbz or Boc; $L^2$ represents OH, $OPG^5$, halogen (such as bromine) or $OSO_2R^a$ wherein $R^a$ is methyl, trifluoromethyl or tolyl; and q represents the integer 1, 2 or 3.

The known epoxides of formula (IVa) can be transformed into the corresponding oxazolidinones of formula (XII) wherein $L^2$ represents $OPG^1$ by reaction with the anions generated from the carbamates of formula (V) (see section b) of part entitled "Preparation of the compounds of formula (I)"). The alcohol protecting group can be removed following general synthetic method 10 and the intermediate alcohols can be transformed following general synthetic method 1 into the corresponding compounds of formula (XII) wherein $L^2$ represents halogen or $OSO_2R^a$, $R^a$ being methyl, trifluoromethyl or tolyl. In the case wherein q is 1, the corresponding activated alcohols can be transformed into the corresponding amines of formula (VII) after reaction with sodium azide and reduction into the corresponding amine following general synthetic method 11. The amines of formula (VII) can be transformed into the amides of formula (XV) by reaction with acrylic acid following general synthetic method 4. The amides of formula (XIV) wherein B=CO can be obtained by reaction of the amines of formula (VII) with the known acids of formula (IVc) wherein Y is O or N-Boc, followed by acidic treatment following general synthetic method 12 and activation of the primary alcohol as a mesylate, tosylate, triflate or halogenide following general synthetic method 1. The compounds of formula (XIV) wherein B is $CH_2$ can be obtained by reductive amination of the known aldehydes of formula (IVd) with the amines of formula (VII) following general synthetic method 3, followed by acidic treatment following general synthetic method 12 and activation of the primary alcohol as a mesylate, tosylate, trifluoromethanesulfonate (triflate) or halogenide following general synthetic method 1.

Preparation of the Compounds of Formula (XIII)

The 2-quinolone and quinoxalin-2-one derivatives of formula (XIII) wherein $R^{1b}$ is H are commercially available or can be prepared according to WO 2006/134378. The 2-quinolone naphthyridin-2-one and quinoxalin-2-one derivatives of formula (XIII) wherein $R^{1b}$ is $(C_1-C_3)$alkyl can be prepared in analogy to *Gazzetta Chimica Italiana* (1967), 97(7), 1061-75, WO 2006/112464 and WO 2006/134378.

Preparation of the Compounds of Formula (XVI)

The derivatives of formula $G-NH_2$ of formula (XVI) are commercially available or may be obtained from the known benzylic alcohols of formula (Va) as described in Scheme 5 hereafter.

Scheme 5

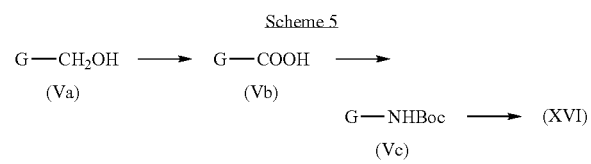

The known benzylic alcohols of formula (Va) can be oxidized into the corresponding carboxylic acids following general synthetic method 13. The resulting carboxylic acids of formula (Vb) can then be reacted with diphenylphosphoryl azide in the presence of t-BuOH between 40° and 100° C., affording the carbamates of formula (Vc). The compounds of formula (XVI; G-N112) are obtained following general synthetic method 9.

Preparation of the Compounds of Formula (XXX)

The intermediates of formula (XXX) can be obtained by reaction of the epoxides of formula (IV) with sodium azide followed by hydrogenation over a noble metal catalyst such as Pd/C and subsequent transformation into their corresponding carbamates with CbzCl or $Boc_2O$. The oxazolidinone ring can then be formed by reaction with NaH.

Preparation of the Compounds of Formula (XXXI)

The derivatives of formula (XXXI) are commercially available (e.g. $G=G^5$, M=N, Q'=O and X=Cl: CAS 337463-99-7; $G=G^5$, M=CH, Q'=S and X=Cl: CAS 6376-70-1; $G=G^5$, M=CH, Q'=O and X=Cl: CAS 7652-29-1) or can be obtained according to known literature procedures (e.g. *J. Org. Chem.* (1990), 4744-59 for 7-chloro-1,8-naphthyridin-2(1H)-one).

The particular compound of formula (XXXI) 6-chloro-4H-pyrido[3,2-b][1,4]thiazin-3-one can be obtained as described in Scheme 6.

Scheme 6

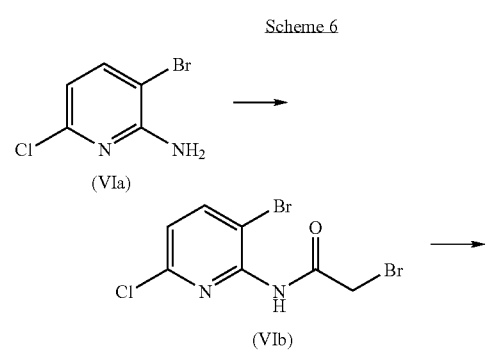

-continued

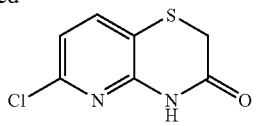

The bromo derivative of formula (VIa), prepared according to WO 2008/065198, can be reacted with bromoacetyl bromide and the resulting derivative of formula (VIb) can be reacted with sodium thioacetate in presence of NaOMe to afford 6-chloro-4H-pyrido[3,2-b][1,4]thiazin-3-one.

Preparation of the Compounds of Formula (XXXII)

The intermediates of formula (XXXII) can be obtained after sequential protection of the hydroxyl group of the compounds of formula (IIIb) (see Scheme 3), removal of the amino protecting group according to general synthetic method 9 and reaction with the intermediates of formula (XII) wherein q is 1 according to general reaction method 2.

Preparation of the Compounds of Formula (XXXIII)

The compounds of formula (XXXIII) can be prepared as summarised in Scheme 7 hereafter.

(XXXIII) can then be obtained in analogy to the method of section i) of part entitled "Preparation of the compounds of formula (I)" by reacting the compounds of formula (XXX) with the compounds of formula (VIIa).

Preparation of Certain Starting Compounds

The intermediate of formula (Ic) can be obtained by reacting 3-hydroxy azetidine with 4-bromo-but-1-ene followed by activation of the alcohol function as a mesylate following [general synthetic method 1] and reaction with NaI in acetone or from the commercially available 2,3-dibromo-1-propanamine and homobenzylic bromide in analogy to *Heterocycles* (2002), 56(1-2), 433-442.

The enamines of formula (IIc) wherein R is Me and PG is Boc or Cbz are commercially available (CAS 55477-80-0 and 21149-17-7).

The chloroalcohol derivatives of formula (IIa) wherein PG is Bee or Cbz are commercially available (CAS 641617-19-8, 641617-18-7 and 415684-05-8).

The compound of formula (IIIc) is commercially available (CAS 254454-54-1).

The compounds of formula (IIIi) are commercially available ($R^1$=MeO: CAS 531-59-9) or prepared according to EP 185319 (e.g. $R^1$=F: CAS 71428-25-6).

The nitro derivatives of formula (IIIe) are commercially available (e.g. $R^1$=OMe, U=CH and $X^a$=Br: CAS 98447-30-4; $R^1$=OMe, U=N and $X^a$==Br: CAS 3442996-05-5; $R^1$=F, U=CH and $X^a$=Br: CAS 700-36-7; $R^1$=Cl, U=N and $X^a$=Cl: CAS 58602-02-1).

The azetidines of formula (IIIf) are commercially available (e.g. $PG^1$=Cbz or Boc: CAS 112257-20-2 and 193269-78-2).

The epoxides of formula (IVa) are commercially available (q=1, $PG^1$=TBDMS: CAS 78906-15-7) or prepared accord- Scheme 7

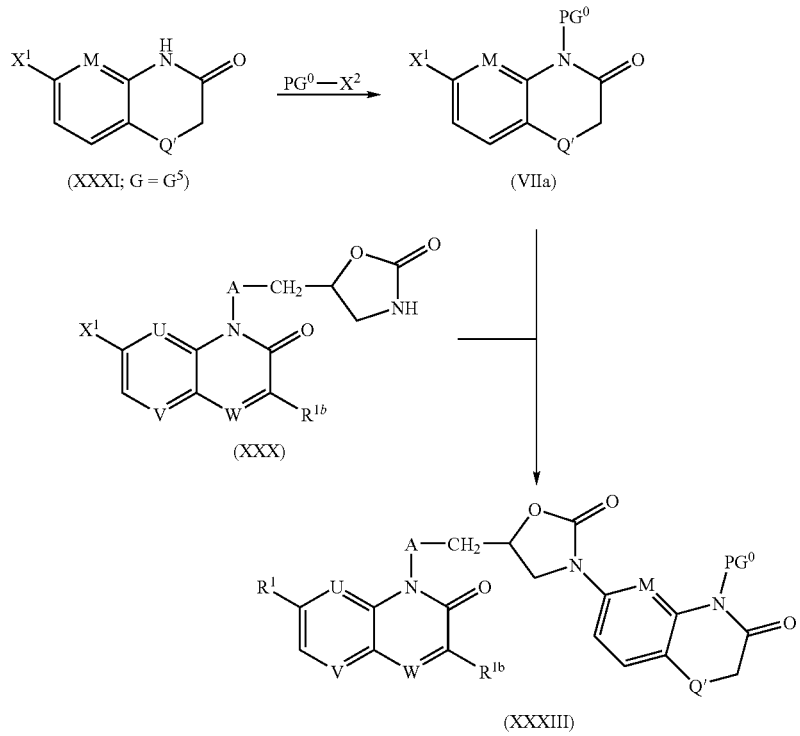

In Scheme 7, $X^1$ and $X^2$ each independently represent halogen such as bromine or chlorine and $PG^0$ represents (4-methoxyphenyl)methyl, (2,4-dimethoxyphenyl)methyl or (3,4-dimethoxyphenyl)methyl.

The compounds of formula (VIIa) are obtained by alkylation of compounds of formula (XXXI) wherein G is $G^5$ and X is $X^1$ with the halogenides of formula $PG^0$-$X^2$ in the presence of a base such a $Cs_2CO_3$. The compounds of formula ing to known procedure (e.g. q=3, PG$^1$=TBDMS: EP 518672; q=2, PG$^1$=TBDMS: WO 2007/144423).

Compounds of formula (IVb) are commercially available (Y=NBoc: CAS 127589-93-9; Y=O: CAS 5736-03-8).

Compounds of formula (IVc) are commercially available (Y=O: CAS 5736-06-1; Y=NH: CAS 159585-65-6).

The alcohols of formula (Va) are commercially available or can be prepared according to WO 03/087098, WO 02/056882 and WO 2007/071936.

The compounds of formulae (VIIIf), (VIIIf') and (VIIIg) can be prepared as summarised in Scheme 8 hereafter.

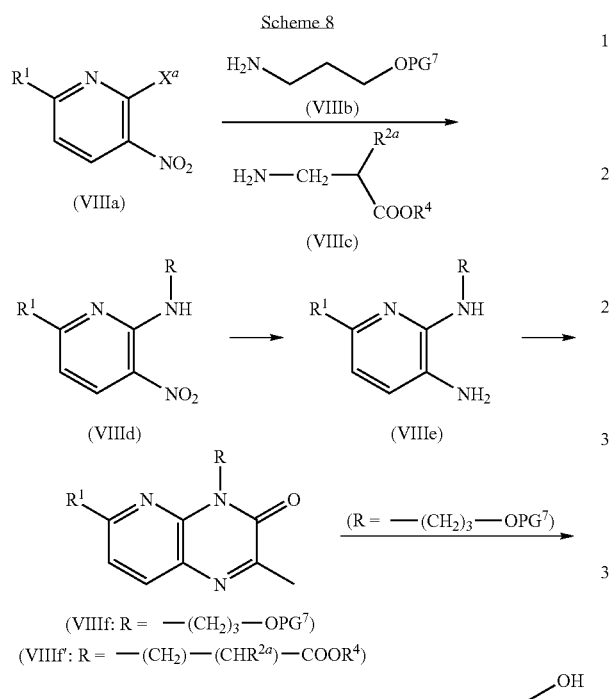

In Scheme 8, X$^a$ represents halogen such as chlorine, R represents —(CH$_2$)$_3$—OPG$^7$ or —CH$_2$—(CHR$^{2a}$)—COOR$^4$, R$^{2a}$ represents H, —OPG$^8$ or —NHPG$^9$, R$^4$ represents alkyl or benzyl, PG$^7$ and PG$^8$ each represent a hydroxy protecting group such as TBDMS and PG$^9$ represents an amino protecting group such as Cbz, Fmoc or Boc.

Accordingly, the compounds of formula (VIIIa) can be reacted with the intermediates of formulae (VIIIb) or (VIIIc), affording the compounds of formula (VIIId) wherein R is either —(CH$_2$)$_3$—OPG$^7$ or —CH$_2$—(CHR$^{2a}$)—COOR$^4$. The compounds of formula (VIIId) can then be reduced into the corresponding diamino derivatives of formula (VIIIe). Said diamino derivatives can then be reacted with alkyl pyruvate, affording the pyrido[2,3-b]pyrazin-3-one derivatives of formula (VIIIf) or (VIIIf'). The compounds of formula (VIIIf) can then be deprotected to yield the compounds of formula (VIIIg).

The compounds of formulae (VIIIf") can be prepared as summarised in Scheme 8a hereafter.

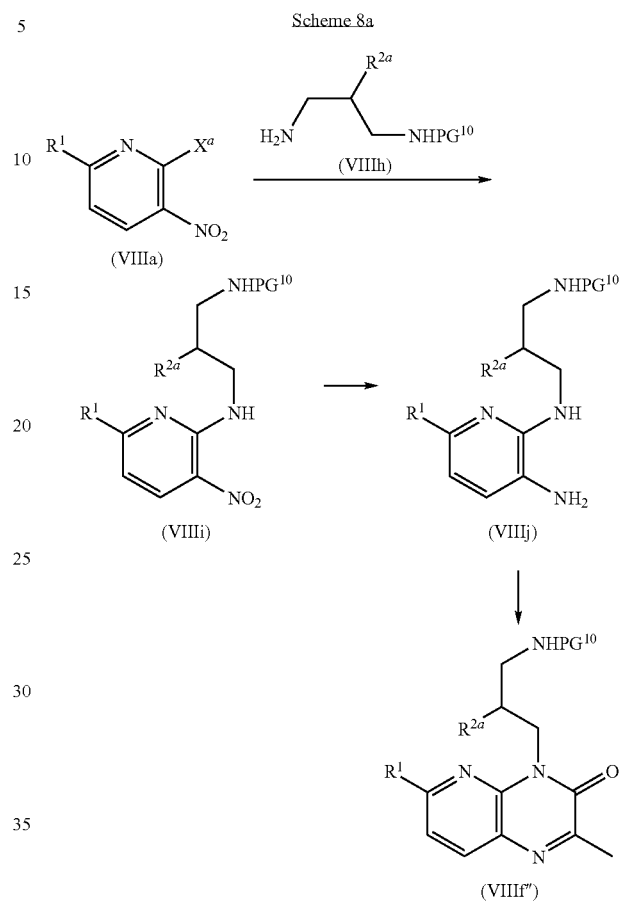

In Scheme 8a, X$^a$ represents halogen such as chlorine, R$^{2a}$ represents H, —OPG$^{11}$ or —NHPG$^{12}$, PG$^{11}$ represents a hydroxy protecting group such as TBDMS and PG$^{10}$ and PG$^{12}$ each represent an amino protecting group such as Cbz, Fmoc or Boc.

Accordingly, the compounds of formula (VIIIa) can be reacted with the intermediates of formulae (VIIIh), affording the compounds of formula (VIIIi). The compounds of formula (VIIIi) can then be reduced into the corresponding diamino derivatives of formula (VIIIj). Said diamino derivatives can then be reacted with alkyl pyruvate, affording the pyrido[2,3-b]pyrazin-3-one derivatives of formula (VIIIf").

The intermediates of formulae (VIIIb), (VIIIc) and (VIIIh) are commercially available (e.g. 3-amino-N-[(phenylmethoxy)carbonyl]-L-alanine tert-butyl ester), or obtained according to literature procedures (e.g. (2S)-3-amino-2-[[(tert-butyl)dimethylsilyl]oxy]-propanoic acid methyl ester: *Bioorg. Med. Chem. Lett.* (2008), 18(3), 1058-1062; N-[(2S)-3-amino-2-[[(tert-butyl)diphenylsilyl]oxy]propyl]-carbamic acid tert-butyl ester: *J. Am. Chem. Soc.* (2008), 130(6), 1836-1838).

Particular embodiments of the invention are described in the following examples, which serve to illustrate the invention in more detail without limiting its scope in any way.

EXPERIMENTAL SECTION

All temperatures are stated in ° C. Compounds are characterized by $^1$H-NMR (300 MHz) (Varian Oxford); or by $^1$H-NMR (400 MHz) (Broker Advance 400). Chemical shifts δ are given in ppm relative to the solvent used; multiplicities: s=singlet, d=doublet, t=triplet, q=quadruplet, p=pentuplet, hex=hexet, hep=heptet, m=multiplet, br=broad, coupling constants are given in Hz. Alternatively compounds are characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC-plates from Merck, Silica gel 60 $F_{254}$); or by melting point. Compounds are purified by chromatography on Silica gel 60A. $NH_4OH$ as used for CC is 25% aq.

The HPLC are done over a stationary phase such as a rapid resolution Zorbax SB C18 (1.8 μm) column, or a rapid resolution Zorbax Eclipse Plus C18 (1.8 μm) column. Typical conditions of HPLC are a gradient of eluent A (water:acetonitrile 95:5 with 0.1% of formic acid, in presence or not of 5 mmol/L ammonium formate) and eluent B (acetonitrile:water 95:5 with 0.1% of formic acid, in presence or not of 5 mmol/L ammonium formate), at a flow rate of 0.8 to 5 mL/min. Racemates can be separated into their enantiomers as described before. Preferred conditions of chiral HPLC are: ChiralPak AD (4.6×250 mm, 5 μm) column, using an isocratic mixture (eg. at a ratio of 10/90) of eluent A (EtOH, in presence of diethylamine in an amount of eg. 0.1%) and eluent B (Hex), at rt, at a flow rate of eg. 0.8 mL/min.

Procedures:

Procedure A: Epoxide Opening:

A solution of epoxide (1 mmol) and amine (1 mmol) in EtOH/$H_2O$ (9:1, 1 to 5 mL) is heated at 80° C. for 12 h. The volatiles are removed under reduced pressure and the residue purified by chromatography by CC. In case the epoxide contains a TBDMS group, the reaction may also be performed in MeCN in presence of 3 eq. $LiClO_4$.

Procedure B: Oxazolidinone Formation with CDI

A solution of the amino alcohol (1 mmol) and CDI (1-2 eq.) in THF (2 mL) is heated at 50° C. until completion of the reaction. The mixture is partitioned between EA (20 mL) and water (20 mL), the org. phase washed with brine (20 mL), dried over $MgSO_4$ and concentrated.

Procedure C: Cbz-Protection of Amines:

A mixture of amine (1 mmol), sat. aq. $NaHCO_3$ (2 mL) and acetone (2 mL) is treated dropwise with Cbz-Cl (1.05 eq.). After $CO_2$ evolvement ceased, the mixture is partitioned between EA and aq. bicarbonate, the org. layer dried over $MgSO_4$ and concentrated.

Procedure D: Formation of a Mesylate:

A solution of the alcohol (4 mmol) in DCM (20 mL) was cooled to 0° C. DIPEA (1.2 eq.) and MSCl (1.1 eq.) were added and the mixture stirred at 0° C. for 1 h. The mixture was diluted with DCM and washed with water. The org. phase was dried over $MgSO_4$ and concentrated to give the desired mesylate as a colourless solid, which was used in the next step without further purification.

Procedure E: Boc Deprotection:

The Boc-protected amine (1 mmol) is dissolved in DCM (5 mL) and treated with TFA (2 mL). The mixture is stirred at rt for 1 h, concentrated in vacuo and taken up in DCM/$NH_4OH$. The org. layer is washed with water, dried over $MgSO_4$ and concentrated. The reaction optionally be performed in presence of $Et_3SiH$.

Procedure F: Silylether Removal:

A solution of the silylether (4 mmol) in THF (10 mL) was treated with TBAF solution (1M in THF, 1 eq.). The solution was stirred at 0° C. for 2 h and at 1-12 h at rt until completion of the reaction, after which water and EA were added. The aq. phase was extracted with EA. The combined org. layers were washed with brine, dried over $MgSO_4$, filtered and concentrated under reduced pressure. The residue was crystallized from ether/EA to afford the desired alcohol.

Procedure G: Oxazolidinones from Glycidyl Butyrates and Cbz-Protected Amines:

A solution of Cbz-protected amine (10 mmol, prepared according to procedure C) in THF (60 mL) was cooled to −78° C. before the dropwise addition of n-BuLi (2.5M solution in hexanes, 1.2 eq.). The mixture was stirred at −78° C. for 1 h and then warmed to −15° C. At this temperature (S or R)-glycidyl butyrate (1.2 eq.) was added dropwise. The mixture was stirred at rt overnight. $Cs_2CO_3$ (tip of a spatula) was added and the mixture heated at 40° C. until complete conversion. The mixture was diluted with EA and washed with sat. $NH_4Cl$ solution and water. The org. layer was dried over $MgSO_4$, concentrated under reduced pressure and purified by CC. Alternatively the reaction can also be performed using 3 eq. of LiOtBu in DMF at rt.

Procedure H: Michael Addition on Acrylate

A solution of the quinolinone derivative (3.5 mmol) in MeCN (7 mL) was refluxed in presence of the required acrylate derivative (1 eq.) and CsF (0.1 eq.). The reaction mixture was diluted with EA (35 mL) and extracted with water (40 mL). The org layer was backwashed with EA and the combined org. layers were dried over $MgSO_4$, evaporated under reduced pressure. The residue was used as such in the following step.

Procedure I: Reductive Amination

A solution of primary amine (1 mmol) and aldehyde or ketone (1 mmol) in DCE/MeOH 1:1 (10 mL) is stirred at rt overnight. $NaBH_4$ (2-5 eq.) is added and the reaction allowed to proceed for another hour. The reaction is diluted with DCM and aq. $NH_4OH$. The org. phase is washed with water, dried over $MgSO_4$ and concentrated.

Procedure J: Formation of Aldehyde from Ester

A solution of the ester (1.46 mmol) in toluene (22 mL) was cooled to −78° C. and treated dropwise with DIBAH (2.6 mL, 4.38 mmol, 3 eq., solution ~1.7M in toluene). The mixture was further stirred at this temperature for 2 h and quenched by the dropwise addition of Rochelles salt (sat. solution, 4 mL). The reaction mixture was allowed to reach rt. The solution was diluted with EA (20 mL) and treated with a sat. solution of Rochelles salt (15 mL). The org. phase was separated and the aq. layer was extracted with EA. The combined org. layers were washed with sat. solution of Rochelles salt (15 mL), dried over $MgSO_4$, filtered and concentrated under reduced. The crude product was purified by CC.

Procedure K: Ester Hydrolysis

A solution of the ester (304 mg) was stirred at 50° C. for 8 h in a mixture of 4N HCl in dioxane (7.5 mL; 2:1). The solution was diluted with EA (20 mL) and water (20 mL). The two phases were separated, the aq. layer was washed with EA (20 mL). The combined org. layers were washed with brine (20 mL) and dried over $MgSO_4$, filtered, concentrated under reduced pressure and used in the next step.

Procedure L: Amide Coupling Using Propylphosphonic Anhydride:

A solution of DIPEA (0.124 mL, 0.75 mmol, 3 eq.), the acid (0.25 mmol, 1 eq.) and the amine (70 mg, 0.25 mmol, 1 eq.) in DMF (2 mL) was treated dropwise with T3P (Propylphosphonic anhydride solution ~50% in EA, 0.162 mL, 0.275 mmol, 1.1 eq.). The reaction mixture was stirred at rt for 6 h, diluted with EA (2 mL) and water (2 mL) and filtered. The crude product was triturated in water, EA/MeOH (1:2) and filtered. The solid was sequentially washed with DCM/ether (1:1) and ether, and dried under HV, affording the desired amide.

Procedure M: Alkylation of an Amine.

A solution of the amine (0.5 mmol), the mesylate or iodide (0.5 mmol) and DIPEA (1.2 eq.) in DMSO (3 mL) was heated at 70° C. for 24 h. The mixture was partitioned between EA and water. The org. layer was washed with water and brine, dried over $MgSO_4$ and concentrated under reduced pressure. The residue was purified by CC.

PREPARATION OF EXAMPLES

Preparation of Intermediates

Intermediate A (R)-5-aminomethyl-3-(2,3-dihydro-benzo[1,4]dioxin-6-yl)-oxazolidin-2-one A.i. (S)-3-(2,3-dihydro-benzo[1,4]dioxin-6-yl)-5-hydroxymethyl-oxazolidin-2-one The title compound was prepared from (2,3-dihydro-benzo[1,4]dioxin-6-yl)-carbamic acid benzyl ester (3.0 g, 10.5 mmol) and (S)-glycidyl butyrate (1.98 g, 1.2 eq.) according to procedure G. The yield was 1.09 g (41%; beige solid).

$^1$H NMR (DMSO d6) δ: 7.13 (d, J=2.5 Hz, 1H), 6.96 (dd, J=2.5, 8.9 Hz, 1H), 6.86 (d, J=8.9 Hz, 1H), 5.16 (t, J=5.8 Hz, 1H), 4.70-4.50 (m, 1H), 4.30-4.10 (m, 4H), 4.10-3.90 (m, 1H), 4.80-4.70 (m, 1H), 4.70-4.60 (m, 1H), 4.60-4.50 (m, 1H).

A.ii. Methanesulfonic acid (S)-3-(2,3-dihydro-benzo[1,4]dioxin-6-yl)-2-oxo-oxazolidin-5-ylmethyl ester The compound was prepared from intermediate A.i (1 g, 4 mmol) according to procedure D. The yield was 1.26 g (97%; colourless solid). The intermediate was used in the next step without further purification.

MS (ESI, m/z): 329.8 [M+H$^+$].

A.iii. (S)-5-azidomethyl-3-(2,3-dihydro-benzo[1,4]dioxin-6-yl)-oxazolidin-2-one

A solution of intermediate A.ii (1.26 g, 3.8 mmol) in DMF (20 mL) was treated with $NaN_3$ (0.3 g, 1.2 eq.) and the mixture heated at 80° C. overnight. The mixture was cooled and partitioned between ether and water. The org. phase was washed with water and brine, dried over $MgSO_4$ and concentrated to give the desired azide as a colourless solid (0.95 g, 90% yield).

MS (ESI, m/z): 277.1 [M+H$^+$].

A.iv. (R)-5-aminomethyl-3-(2,3-dihydro-benzo[1,4]dioxin-6-yl)-oxazolidin-2-one

A solution of intermediate A.iii (0.95 g, 3.4 mmol) in EtOH/THF (1:1, 40 mL) was hydrogenated over Pd(OH)$_2$ (0.18 g, 0.1 eq.) under 1 bar of H$_2$ for 3 h. The catalyst was filtered off and the filtrate concentrated in vacuo to give the desired amine as a colourless solid (0.62 g, 72% yield).

$^1$H NMR (DMSO d6) δ: 7.12 (d, J=2.5 Hz, 1H), 6.98 (dd, J=2.5, 8.9 Hz, 1H), 6.86 (d, J=8.9 Hz, 1H), 4.60-4.50 (m, 1H), 4.30-4.10 (m, 4H), 3.99 (t, J=8.8 Hz, 1H), 3.79 (dd, J=6.5, 8.8 Hz, 1H), 3.90-3.75 (m, 2H).

MS (ESI, m/z): 251.0 [M+H$^+$].

Intermediate B 6-((R)-5-aminomethyl-2-oxo-oxazolidin-3-yl)-4H-benzo[1,4]thiazin-3-one B.i. (R)-3-chloro-2-hydroxy-propyl)-carbamic acid tert-butyl ester This intermediate (25.6 g, 45% yield) was prepared according to the literature (Org. Process Research and Development (2003), 7, 533-546) starting from (R)-epichlorohydrin (25 g, 270 mmol).

$^1$H NMR (CDCl$_3$) δ: 4.95 (br, 1H), 4.00-3.80 (m, 1H), 3.60-3.50 (m, 2H), 3.50-3.35 (m, 2H), 3.30-3.20 (m, 1H), 1.42 (s, 9H).

B.ii. (R)-1-oxiranylmethyl-carbamic acid tert-butyl ester

NaOMe (1.9 g, 34.9 mmol) was added to a solution of intermediate B.i (3.66 g, 17.4 mmol) in MeOH. The mixture was stirred at rt for 6 h, concentrated in vacuo and partitioned between water and ether. The org. layer was washed with sat. NH$_4$Cl solution, dried over MgSO$_4$ and concentrated to give the title epoxide as a colourless oil (1.38 g, 45% yield).

$^1$H NMR (DMSO d6) δ: 4.71 (br, 1H), 3.52 (m, 1H), 3.21 (m, 1H), 3.08 (m, 1H), 2.77 (m, 1H), 1.42 (s, 9H).

B.iii. [(S)-2-hydroxy-3-(3-oxo-3,4-dihydro-2H-benzo[1,4]thiazin-6-ylamino)-propyl]-carbamic acid tert-butyl ester This amino alcohol is synthesized according to procedure A starting from intermediate B.ii (0.78 g, 4.5 mmol) and 6-amino-4H-benzo[1,4]thiazin-3-one (0.68 g, 4.5 mmol). The compound was isolated after CC (hex/EA 2:1, 1:1, 1:2) as a beige foam (1.08 g, 68% yield).

MS (ESI, m/z): 354.2 [M+H$^+$].

B.iv. [(R)-2-oxo-3-(3-oxo-3,4-dihydro-2H-benzo[1,4]thiazin-6-yl)-oxazolidin-5-ylmethyl]-carbamic acid tert-butyl ester The compound was obtained from B.iii (1.5 g, 4.2 mmol) and CDI (0.78 g, 1.1 eq.) according to procedure B (in order to push the reaction to completion NaH (1 eq.) was added an stirring was continued at rt overnight). The compound was purified by CC (hex/EA 1:2) giving the title oxazolidinone (0.61 g, 38% yield) as a pink foam.

$^1$H NMR (DMSO d6) δ: 10.56 (s, 1H), 7.30 (m, 2H), 7.18 (m, 1H), 7.08 (dd, J=8.5, 2.3 Hz, 1H), 4.66 (m, 1H), 4.02 (m, 1H), 3.73 (dd, J=8.8, 6.2 Hz, 1H), 3.40 (s, 2H), 3.30-3.20 (m, 2H), 1.34 (s, 9H).

B.v. 6-((R)-5-aminomethyl-2-oxo-oxazolidin-3-yl)-4H-benzo[1,4]thiazin-3-one

The Boc group of intermediate B.iv (0.6 g, 1.58 mmol) was removed according to procedure E. The title amine was isolated as a beige foam (0.37 g, 85% yield).

MS (ESI, m/z): 280.2 [M+H$^+$].

Intermediate C methanesulfonic acid (S)-2-oxo-3-(3-oxo-3,4-dihydro-2H-benzo[1,4]oxazin-6-yl)-oxazolidin-5-ylmethyl ester C.i 6-[(S)-3-(tert-butyl-dimethyl-silanyloxy)-2-hydroxy-propylamino]-4H-benzo[1,4]oxazin-3-one To a solution of tert-butyl-dimethyl-((S)-1-oxiranyl-methoxy)-silane (commercial; 10.0 g, 53 mmol) in MeCN (160 mL) was added LiClO$_4$ (16.9 g, 159 mmol). 6-amino-4H-benzo[1,4]oxazin-3-one (commercial; 8.72 g, 53.1 mmol) was added and the mixture was stirred at 50° C. for 6 h. The solvent was removed in vacuo and the residue was purified by CC (DCM/MeOH/NH$_4$OH 1000:25:2→1000:100:2) to afford the title compound as a pale brown foam (10.24 g, 55% yield).

MS (ESI, m/z): 353.3 [M+H$^+$].

C.ii. 6-[(S)-5-(tert-butyl-dimethyl-silanyloxymethyl)-2-oxo-oxazolidin-3-yl]4H-benzo[1,4]oxazin-3-one A solution of intermediate C.i (10.24 g, 29 mmol) and CDI (9.71 g, 58.1 mmol) in THF (140 mL) was heated at 50° C. for 2 h; the mixture was concentrated in vacuo and partitioned between EA and water. The org. layer was washed with brine, dried over MgSO$_4$ and concentrated under reduced pressure. The residue was triturated with ether to afford the title intermediate as a yellowish solid (6.30 g, 57% yield).

MS (ESI, m/z): 379.2 [M+H$^+$].

C.iii. 6-((S)-5-hydroxymethyl-2-oxo-oxazolidin-3-yl)-4H-benzo[1,4]oxazin-3-one

A suspension of intermediate C.ii (6.30 g, 16.6 mmol) in THF (20 mL) was treated with TBAF (1M in THF, 16.6 mL) at 0° C. The yellow solution was stirred at 0° C. for 3 h and then partitioned between water and EA. The aq. phase was extracted with EA (3×). The combined org. layers were washed with brine, dried over MgSO$_4$, filtered and concentrated under reduced pressure. The crude product was triturated with EA to give the title intermediate as a colourless solid (3.49 g, 79% yield).

MS (ESI, m/z): 265.5 [M+H$^+$].

C.iv. Methanesulfonic acid (S)-2-oxo-3-(3-oxo-3,4-dihydro-2H-benzo[1,4]oxazin-6-yl)-oxazolidin-5-ylmethyl ester A solution of intermediate C.iii (2.44 g, 9.23 mmol) in DCM (50 mL) was cooled to 0° C. DIPEA (3.58 g, 3 eq.) and Ms-Cl (1.27 g, 1.2 eq.) were added and the mixture stirred at 0° C. for 1 h. The mixture was diluted with DCM and washed with water. The org. phase was dried over MgSO$_4$ and concentrated. The residue was purified by CC (DCM/MeOH 1000:50:4) to afford the title compound as an off-white solid (1.40 g, 44% yield).

$^1$H NMR (DMSO-d6) δ: 10.72 (s, 1H), 7.29 (dd, J=2.1, 0.6 Hz, 1H), 6.94 (m, 2H), 4.95 (m, 1H), 4.52 (s, 2H), 4.49 (m, 2H), 4.11 (t, J=9.1 Hz, 1H), 3.73 (m, 2H), 3.23 (s, 3H).

MS (ESI, m/z): 343.2 [M+H$^+$].

Intermediate D (RS)-methanesulfonic acid 2-[2-oxo-3-(3-oxo-3,4-dihydro-2H-benzo[1,4]thiazin-6-yl)-oxazolidin-5-yl]-ethyl ester D.i. (RS)-6-[4-(tert-butyl-dimethyl-silanyloxy)-2-hydroxy-butylamino]-4H-benzo[1,4]thiazin-3-one The compound was obtained according to procedure A starting from (RS)-tert-butyl-dimethyl-(2-oxiranyl-ethoxy)-silane (4 g, 20 mmol, prepared according to *Heterocycles* (1987), 25(1), 329-32) and 6-amino-4H-benzo[1,4]thiazin-3-one (4 g, 20 mmol) in EtOH/water 9:1 (140 mL). The compound was purified by CC (DCM/MeOH/NH$_4$OH 1000:50:4), affording a brown oil (2.2 g, 29% yield).

MS (ESI, m/z): 383.2 [M+H$^+$].

D.ii. (RS)-6-{5-[2-(tert-butyl-dimethyl-silanyloxy)-ethyl]-2-oxo-oxazolidin-3-yl}-4H-benzo[1,4]thiazin-3-one According to procedure B the title intermediate was obtained from intermediate D.i and isolated as an orange solid (1.53 g, 65% yield) after CC (DCM/MeOH/NH$_4$OH 1000:50:4).

MS (ESI, m/z): 409.4 [M+H$^+$].

D.iii. (RS)-6-[5-(2-hydroxy-ethyl)-2-oxo-oxazolidin-3-yl]-4H-benzo[1,4]thiazin-3-one The compound was prepared according to procedure F starting from intermediate D.ii (1.50 g, 3.67 mmol). The residue was recrystallized from ether/EA to afford the title intermediate as a beige solid (730 mg, 68% yield).

MS (ESI, m/z): 295.1 [M+H$^+$].

D.iv. (RS)-methanesulfonic acid 2-[2-oxo-3-(3-oxo-3,4-dihydro-2H-benzo[1,4]thiazin-6-yl)-oxazolidin-5-yl]-ethyl ester The compound was obtained according to procedure D starting from intermediate D.iii (700 mg, 2.34 mmol). The yellow residue was purified by CC (DCM/MeOH/NH$_4$OH 1000:50:4), affording the title intermediate as a beige solid (795 mg, 90% yield).

MS (ESI, m/z): 373.1 [M+H$^+$].

Intermediate E 6-(S)-5-iodomethyl-2-oxo-oxazolidin-3-yl)-4H-benzo[1,4]thiazin-3-one E.i. 6-[(S)-3-(tert-butyl-dimethyl-silanyloxy)-2-hydroxy-propylamino]-4H-benzo[1,4]thiazin-3-one To a solution of tert-butyl-dimethyl-((S)-1-oxiranyl-methoxy)-silane (commercial; 13.0 g, 69 mmol) in MeCN (220 mL) was added LiClO$_4$ (22 g, 207 mmol). 6-amino-4H-benzo[1,4]thiazin-3-one (commercial; 11.45 g, 64 mmol) was added and the mixture was stirred at 50° C. for 6 h. The solvent was removed in vacuo and the residue was purified by CC (DCM/MeOH/NH$_4$OH 1000:25:2→1000:100:2) to afford the title compound as a pale brown foam (11.16 g, 44% yield).

MS (ESI, m/z): 353.3 [M+H$^+$].

E.ii. 6-[(S)-5-(tert-butyl-dimethyl-silanyloxymethyl)-2-oxo-oxazolidin-3-yl]-4H-benzo[1,4]thiazin-3-one A solution of intermediate E.i (11.16 g, 30 mmol) and CDI (5.57 g, 33 mmol) in THF (130 mL) was heated at 50° C. for 2 h; the mixture was concentrated in vacuo and partitioned between EA and water. Some crystallized product was filtered and washed with H₂O and EA to give 5.21 g of solid. The org. layer was washed with brine, dried over MgSO₄ and concentrated under reduced pressure. The residue was purified by CC (DCM/MeOH 1000:50:4) to give additional 2.28 g as a colourless solid (total 7.49 g, 63% yield).
MS (ESI, m/z): 379.2 [M+H⁺].

E.iii. 6-((S)-5-hydroxymethyl-2-oxo-oxazolidin-3-yl)-4H-benzo[1,4]thiazin-3-one

A suspension of intermediate E.ii (11.49 g, 29.1 mmol) in THF (30 mL) was treated with TBAF (1M in THF, 29.1 mL) at 0° C. The yellow solution was stirred at 0° C. for 3 h and then partitioned between water and EA. Some crystallized product was filtered and washed with H₂O and EA to give 6.49 g of solid. The aq. phase was extracted with EA (3×). The combined org. layers were washed with brine, dried over MgSO₄, filtered and concentrated under reduced pressure. The crude product was triturated with EA to give 1.23 g (overall 7.72 g of an off-white solid, 95% yield).
MS (ESI, m/z): 265.5 [M+H⁺].

E.iv. Toluene-4-sulfonic acid (S)-2-oxo-3-(3-oxo-3,4-dihydro-2H-benzo[1,4]thiazin-6-yl-oxazolidin-5-ylmethyl ester To a solution of intermediate E.iii (3.22 g, 11.5 mmol) and DMAP (1.40 g, 11.5 mmol) in DCM (80 mL) cooled to 0° C. were added TEA (4.6 mL, 33.3 mmol) and a solution of TsCl (2.19 g, 11.5 mmol) in DCM (15 mL). The mixture was stirred at rt overnight after which water was added. The resulting solid was filtered and dried to afford the title compound as a beige solid (4.19 g, 84% yield).
MS (ESI, m/z): 435.2 [M+H⁺].

E.v. 6-((S)-5-iodomethyl-2-oxo-oxazolidin-3-yl)-4H-benzo[1,4]thiazin-3-one

A suspension of intermediate E.iv (4.19 g, 9.64 mmol) and NaI (5.78 g, 38.57 mmol) in acetone (70 mL) was refluxed for 5 h. The solvent was evaporated and the residue extracted with water/DCM. Thereby the desired product precipitated as a pale beige solid (3.40 g; 90% yield)
MS (ESI, m/z): 391.1 [M+H⁺].

Intermediate F 7-fluoro-6-((S)-5-iodomethyl-2-oxo-oxazolidin-3-yl)-4H-benzo[1,4]thiazin-3-one F.i. 6-amino-7-fluoro-4H-benzo[1,4]thiazin-3-one Starting from 1,5-difluoro-2,4-dinitro-benzene (5 g) and following the procedure described in the literature (*Biosci. Biotechnol., Biochem.* 1994, 58, 788), the title aniline was isolated as a beige solid (2 g, 55% yield).
¹H NMR (DMSO-d6) δ: 10.28 (s, 1H), 6.94 (d, J=10.8 Hz, 1H), 6.40 (d, J=8.5 Hz, 1H), 5.22 (s, 2H), 3.31 (s, 2H).

F.ii. 7-fluoro-6-((S)-5-chloromethyl-2-oxo-oxazolidin-3-yl)-4H-benzo[1,4]thiazin-3-one Starting from intermediate F.i (1 g, 5.05 mmol) and (S)-epichlorohydrin (0.4 ml) and following procedures A and B, the title intermediate was isolated as a brown solid (380 mg, 30% yield).
MS (ESI, m/z): 317.1 [M+H⁺].

F.iii 7-fluoro-6-((S)-5-iodomethyl-2-oxo-oxazolidin-3-yl)-4H-benzo[1,4]thiazin-3-one A sat. solution of intermediate F.ii (0.38 g, 1.5 mmol) in 2-butanone at reflux (3 mL) was treated with NaI and heated at reflux (80° C.) over 2 nights. The mixture was cooled to rt and concentrated under reduced pressure and digested with water, vigorously stirred for 5 min and filtered. The precipitated product was purified by CC (Hept/EA 1:1, EA/MeOH 9:1) to give 390 mg (80% yield) of a beige solid.
MS (ESI, m/z): 409.1 [M+H⁺].

Intermediate G (S)-3-(2,3-dihydro-benzo[1,4]dioxin-6-yl)-5-iodomethyl-oxazolidin-2-one G.i. (S)-3-(2,3-dihydro-benzo[1,4]dioxin-6-yl)-5-hydroxymethyl-oxazolidin-2-one A solution of (2,3-dihydro-benzo[1,4]dioxin-6-yl)-carbamic acid benzyl ester (13.0 g, 45.6 mmol) in THF (220 mL) was cooled to −78° C. before the drop wise addition of ii-BuLi (29.5 mL of a 2.36M solution in Hex, 1.1 eq.). The mixture was stirred at −78° C. for 1 h and then warmed to −15° C. At this temperature (S)-glycidyl butyrate (7.37 g, 1.1 eq.) was added dropwise. The mixture was stirred at rt overnight. Cs₂CO₃ (tip of a spatula) was added and the mixture heated at 40° C. until complete conversion. The mixture was diluted with EA and washed with a sat. aq. NH₄Cl and water. The org. layer was dried over MgSO₄ and concentrated. The residue was purified by CC (Hex/EA 2:1, 1:1) to afford the title intermediate as a grey solid (7.04 g, 62% yield).
¹H NMR (DMSO-d6) δ: 7.13 (d, J=2.5 Hz, 1H), 6.96 (dd, J=2.5, 8.9 Hz, 1H), 6.86 (d, J=8.9 Hz, 1H), 5.16 (t, J=5.8 Hz, 1H), 4.70-4.50 (m, 1H), 4.30-4.10 (m, 4H), 4.10-3.90 (m, 1H), 4.80-4.70 (m, 1H), 4.70-4.60 (m, 1H), 4.60-4.50 (m, 1H).

G.ii. Methanesulfonic acid (S)-3-(2,3-dihydro-benzo[1,4]dioxin-6-yl)-2-oxo-oxazolidin-5-ylmethyl ester A solution of intermediate G.i (7.0 g, 27.9 mmol) in DCM (140 mL) was cooled to 0° C. DIPEA (5.70 mL, 1.2 eq) and MsCl (2.40 mL, 1.1 eq) were added and the mixture was stirred for 1 h at 0° C. The mixture was diluted with DCM and washed with water. The org. phase was dried over MgSO₄ and concentrated to give the title intermediate as a colourless solid (9.0 g, 98% yield).
MS (ESI, m/z): 330.3 [M+H⁺].

G.iii. (S)-3-(2,3-Dihydro-benzo[1,4]dioxin-6-yl)-5-iodomethyl-oxazolidin-2-one

A mixture of intermediate G.ii (9.0 g, 27.3 mmol) and NaI (16.4 g, 4 eq.) in acetone (150 mL) was heated at reflux for 20 h. The solvent was evaporated and the residue extracted with water/DCM. The org. layer was washed with brine, dried over MgSO₄ and concentrated under reduced pressure. The residue was triturated with ether/EA to afford the title intermediate as an off-white solid (6.91 g, 70% yield).
¹H NMR (CDCl₃) δ: 7.07 (d, J=2.6 Hz, 1H), 6.98 (dd, J=9.1, 2.6 Hz, 1H), 6.85 (d, J=8.9 Hz, 1H), 4.68 (m, 1H), 4.24 (s, 4H), 4.10 (t, J=9.1 Hz, 1H), 3.72 (dd, J=9.1, 5.9 Hz, 1H), 3.46 (m, 1H), 3.33 (m, 1H).
MS (ESI, m/z): 362.2 [M+H⁺].

Intermediate H methanesulfonic acid 2-[(R)-2-oxo-3-(3-oxo-3,4-dihydro-2H-benzo[1,4]thiazin-6-yl)-oxazolidin-5-yl]-ethyl ester

H.i. Tert-butyl-dimethyl-((R)-2-oxiranyl-ethoxy)-silane and (2S)-4-(tert-butyl-dimethyl-silanyloxy)-butane-1,2-diol The title intermediates were prepared in analogy to Kishi et al. *Org. Lett.* 2005, 7, 3997 (intermediate S2-3), via hydrolytic kinetic resolution of (RS)-tert-butyl-dimethyl-(2-oxiranyl-ethoxy)-silane (prepared according to *J. Org. Chem.* 2008, 73, 1093). Two compounds were isolated after CC (Hept/EA 2:1):

First eluting compound: tert-butyl-dimethyl-((R)-2-oxiranyl-ethoxy)-silane (colourless oil, 25.3 g, 48% yield). $^1$H NMR (CDCl$_3$) δ: 3.77 (t, J=6.4 Hz, 2H), 3.04 (m, 1H), 2.78 (m, 1H), 2.51 (dd, J=5.0, 2.9 Hz, 1H), 1.74 (m, 2H), 0.90 (d, J=0.6 Hz, 9H), 0.06 (s, 6H).

Second eluting compound: (2S)-4-(tert-butyl-dimethyl-silanyloxy)-butane-1,2-diol (colourless oil, 24.9 g, 43% yield). $^1$H NMR (CDCl$_3$) δ: 3.89 (m, 3H), 3.62 (s, 1H), 3.53 (m, 1H), 3.42 (br. s, 1H), 2.29 (m, 1H), 1.70 (m, 2H), 0.90 (s, 9H), 0.09 (s, 6H).

H.ii. 6-[(R)-4-(tert-butyl-dimethyl-silanyloxy)-2-hydroxy-butylamino]-4H-benzo[1,4]thiazin-3-one A solution of 6-amino-4H-benzo[1,4]thiazin-3-one (10.68 g, 59.3 mmol; commercial) and tert-butyl-dimethyl-((R)-2-oxiranyl-ethoxy)-silane (as described in H.i, 12.0 g, 59.3 mmol) in 9-1 EtOH/H$_2$O (320 mL) was heated at 80° C. for 2 days. The mixture was concentrated under reduced pressure. Residual starting aniline could be removed by addition of ether/MeOH followed by filtration. The mother liquor containing the product was concentrated under reduced pressure to afford the title intermediate as a brown oil (18.8 g, 83% yield) which was used as such in the next step.

MS (ESI, m/z): 383.2 [M+H$^+$].

H.iii. 6-{((R)-5-[2-(tert-butyl-dimethyl-silanyloxy)-ethyl]-2-oxo-oxazolidin-3-yl}-4H-benzo[1,4]thiazin-3-one A solution of intermediate H.ii (23.5 g, 49.1 mmol) and CDI (9.57 g, 1.2 eq.) in THF (250 mL) was heated at 50° C. overnight. The mixture was concentrated under reduced pressure and partitioned between EA and water. The aq. layer was extracted once more with EA and the combined org. layers were dried over MgSO$_4$ and concentrated. The residue was purified by CC (DCM/MeOH/NH$_4$OH 1000:50:4) to afford the title intermediate as a colourless solid (8.4 g, 42% yield).

MS (EST, m/z): 409.3 [M+H$^+$].

H.iv. 6-[(R)-5-(2-hydroxy-ethyl)-2-oxo-oxazolidin-3-yl]-4H-benzo[1,4]thiazin-3-one A solution of intermediate H.iii (8.4 g, 20.6 mmol) in THF (50 mL) was treated with TBAF (1M solution in THF, 24.7 mL, 1.2 eq.) at 0° C. The solution was stirred at 0° C. for 6 h. The mixture was partitioned between water and EA and the aq. phase was extracted with EA (3×). The combined org. layers were washed with water and brine, dried over MgSO$_4$ and concentrated. The residue was triturated with ether/EA to afford the title intermediate as an off-white solid (4.79 g, 79% yield).

MS (ESI, m/z): 295.5 [M+H$^+$].

H.v. Methanesulfonic acid 2-[(R)-2-oxo-3-(3-oxo-3,4-dihydro-2H-benzo[1,4]thiazin-6-yl)-oxazolidin-5-yl]-ethyl ester A solution of intermediate H.iv (4.7 g, 16.0 mmol) and DIPEA (7.54 mL, 2.9 eq.) in anhydrous DCM (80 mL) was cooled to 0° C. and treated dropwise with MsCl (1.50 mL, 1.2 eq.). The resulting mixture was stirred at 0° C. for 1 h. Water and DCM were added and the phases separated. The org. layer was dried over MgSO$_4$ and concentrated under reduced pressure. The residue was purified by CC (DCM/MeOH/NH$_4$OH 1000:50:4) to afford the title intermediate as an off-white solid (5.80 g, 98% yield).

MS (ESI, m/z): 373.4 [M+H$^+$].

Intermediate I methanesulfonic acid 2-[(S)-2-oxo-3-(3-oxo-3,4-dihydro-2H-benzo[1,4]oxazin-6-yl)-oxazolidin-5-yl]-ethyl ester

I.i. Toluene-4-sulfonic acid (S)-4-(tert-butyl-dimethyl-silanyloxy)-2-hydroxy-butyl ester To a solution of (2S)-4-(tert-butyl-dimethyl-silanyloxy)-butane-1,2-diol (23.9 g, 108 mmol, second eluting compound of H.i) and DMAP (2.65 g, 0.2 eq.) in DCM (80 mL) cooled to 0° C. were added TEA (43.8 mL, 2.9 eq.) and a solution of p-TsCl (20.7 g, 11q) in DCM (15 mL). The mixture was stirred at rt for 5 h, poured on NaHCO$_3$ and extracted with DCM. The org. layer was dried over MgSO$_4$ and concentrated. The residue was purified by CC (Hept/EA 2:1) to afford the title intermediate as a colourless oil (31.3 g, 77% yield).

$^1$H NMR (CDCl$_3$) δ: 7.80 (d, J=7.6 Hz, 2H), 7.34 (d, J=7.6 Hz, 2H), 4.02 (m, 3H), 3.80 (m, 2H), 2.45 (s, 3H), 1.70 (m, 2H), 1.27 (m, 1H), 0.87 (s, 9H), 0.05 (s, 6H).

I.ii. Tert-butyl-dimethyl-((S)-2-oxiranyl-ethoxy)-silane

To a solution of intermediate I.i (31.1 g, 83.1 mmol) in THF (350 mL) was added 2M NaOH (35 mL) and the mixture was vigorously stirred at rt for 3 h. The mixture was taken in 1M NaOH (200 mL) and extracted with TBME (2×). The combined org. layers were washed with water and brine, dried over MgSO$_4$ and concentrated. The resulting oil was purified by Kugelrohr-distillation (ca. 70° C. at 0.1 mbar) to afford the title intermediate as a colourless oil (14.7 g, 87% yield).

$^1$H NMR (CDCl$_3$) δ: 3.77 (t, J=6.4 Hz, 2H), 3.04 (m, 1H), 2.78 (m, 1H), 2.51 (dd, J=5.0, 2.9 Hz, 1H), 1.74 (m, 2H), 0.90 (d, J=0.6 Hz, 9H), 0.06 (s, 6H).

I.iii. 6-[(S)-4-(tert-butyl-dimethyl-silanyloxy)-2-hydroxy-butylamino]-4H-benzo[1,4]oxazin-3-one A solution of 6-amino-4H-benzo[1,4]oxazin-3-one (5.03 g, 30.6 mmol; commercial) and intermediate I.ii (6.2 g, 1 eq.) in 9-1 EtOH/H$_2$O (180 mL) was heated at 80° C. for 2 days. The mixture was concentrated under reduced pressure. Residual starting aniline could be removed by addition of ether/MeOH followed by filtration. The mother liquor containing the product was concentrated under reduced pressure to afford the title intermediate as a brown oil (9.45 g, 84% yield) which was used as such in the next step.
MS (ESI, m/z): 367.2 [M+H$^+$].

I.iv. 6-{(S)-5-[2-(tert-butyl-dimethyl-silanyloxy)-ethyl]-2-oxo-oxazolidin-3-yl}-4H-benzo[1,4]oxazin-3-one A solution of intermediate I.iii (9.4 g, 25.6 mmol) and CDI (4.99 g, 1.2 eq.) in THF (100 mL) was heated at 50° C. overnight. The mixture was concentrated under reduced pressure and partitioned between EA and water. The aq. layer was extracted once more with EA and the combined org. layers were washed with 0.5M HCl (2×) and water, dried over MgSO$_4$ and concentrated. The residue was triturated, the solids filtered off and the mother liquor was concentrated. The resulting solid was triturated once more, the solids filtered off and the mother liquor was concentrated. The residue was purified by CC (DCM/MeOH/NH$_4$OH 1000:50:4) to afford the title intermediate as a beige solid (2.40 g, 24% yield).
MS (EST, m/z): 393.4 [M+H$^+$].

I.v. 6-[(S)-5-(2-hydroxy-ethyl)-2-oxo-oxazolidin-3-yl]-4H-benzo[1,4]oxazin-3-one A solution of intermediate I.iv (2.40 g, 6.11 mmol) in THF (12 mL) was treated with TBAF (1M solution in THF, 7.33 mL, 1.2 eq.) at 0° C. The solution was stirred at 0° C. for 6 h. The mixture was partitioned between water and EA and the aq. phase was extracted with EA (3×). The combined org. layers were washed with water (3×) and brine, dried over MgSO$_4$ and concentrated. The residue was triturated with ether/EA to afford the title intermediate as an off-white solid (0.82 g, 48% yield).
MS (ESI, m/z): 279.5 [M+H$^+$].

I.vi. Methanesulfonic acid 2-[(S)-2-oxo-3-(3-oxo-3,4-dihydro-2H-benzo[1,4]oxazin-6-yl-oxazolidin-5-yl]-ethyl ester A solution of intermediate I.v (0.82 g, 2.95 mmol) and DIPEA (1.4 mL, 2.9 eq.) in anhydrous DCM (15 mL) was cooled to 0° C. and treated dropwise with MsCl (0.28 mL, 1.2 eq.). The resulting mixture was stirred at 0° C. for 1 h. Water and DCM were added and the phases separated. The org. layer was dried over MgSO$_4$ and concentrated under reduced pressure. The residue was triturated with MeOH to afford the title intermediate as a beige solid (0.61 g, 58% yield).
MS (ESI, m/z): 357.3 [M+H$^+$].

Intermediate J

6-[(R)-5-(2-iodo-ethyl)-2-oxo-oxazolidin-3-yl]-4H-benzo[1,4]thiazin-3-one

A suspension of intermediate H.v (3.5 g, 9.4 mmol) and NaI (4.23 g, 3 eq.) in 2-butanone (35 mL) was heated at 85° C. overnight. After cooling, the mixture was diluted with ether/EA (20 mL) and treated with 10% aq. Na$_2$S$_2$O$_3$ (60 mL). After stirring for 10 min the phases were separated and the aq. layer was washed with EA. The combined org. layers were washed with water (2×), dried over MgSO$_4$ and concentrated under reduced pressure. The residue was triturated with ether/EA to afford the title intermediate as an off-white solid (3.52 g, 93% yield).
MS (ESI, m/z): 405.0 [M+H$^+$].

Intermediate K methanesulfonic acid 3-[(R)-2-oxo-3-(3-oxo-3,4-dihydro-2H-benzo[1,4]thiazin-6-yl)-oxazolidin-5-yl]-propyl ester K.i. 6-[(R)-5-(tert-butyl-dimethyl-silanyloxy)-2-hydroxy-pentylamino]-4H-benzo[1,4]thiazin-3-one A mixture of tert-butyl-dimethyl-((R)-3-oxiranyl-propoxy)-silane (13 g, 60 mmol, prepared according to Org. Lett. 2005, 7, 3997) and 6-amino-4H-benzo[1,4]thiazin-3-one (10.8 g) in EtOH/H$_2$O (9:1, 325 mL) was heated at reflux overnight. The volatiles were removed under reduced pressure and the residue purified by CC (Hept/EA 1:1) to give the desired intermediate (6.8 g, 28% yield) as a brown oil.
MS (ESI, m/z): 397.1 [M+H$^+$].

K.ii. 6-{(R)-5-[3-(tert-butyl-dimethyl-silanyloxy)-propyl]-2-oxo-oxazolidin-3-yl}-4H-benzo[1,4]thiazin-3-one Starting with intermediate K.i (6.7 g, 17 mmol) and using procedure B, the title intermediate was obtained as a orange solid (7.8 g, quant.).
MS (ESI, m/z): 423.4 [M+H$^+$].

K.iii. 6-[(R)-5-(3-hydroxy-propyl)-2-oxo-oxazolidin-3-yl]-4H-benzo[1,4]thiazin-3-one Starting with intermediate K.ii (7.1 g, 16.8 mmol) and using procedure F, the title intermediate was obtained as a yellowish solid (3.1 g, 60% yield).
MS (ESI, m/z): 309.1 [M+H$^+$].

K.iv. Methanesulfonic acid 3-[(R)-2-oxo-3-(3-oxo-3,4-dihydro-2H-benzo[1,4]thiazin-6-yl)-oxazolidin-5-yl]-propyl ester Starting with intermediate K.iii (0.42 g, 1.36 mmol) and using procedure D, the title intermediate was obtained as a beige solid (0.4 g, 76% yield).
MS (ESI, m/z): 387.2 [M+H$^+$].

Intermediate L methanesulfonic acid 2-[(S)-2-oxo-3-(3-oxo-3,4-dihydro-2H-benzo[1,4]thiazin-6-yl)-oxazolidin-5-yl]-ethyl ester L.i. 6-[(S)-4-(tert-butyl-dimethyl-silanyloxy)-2-hydroxy-butylamino]-4H-benzo[1,4]oxazin-3-one A suspension of 6-amino-4H-benzo[1,4]thiazin-3-one (24.5 g, 136 mmol; commercial), intermediate I.ii (6.2 g, 1 eq) and LiClO$_4$ (43.4 g, 3 eq) in acetonitrile (400 mL) was heated at 60° C. for 4 h. The mixture was concentrated under reduced pressure. The mixture was partitioned between EA and water. The org. phase was washed with water and brine, dried over MgSO$_4$ and concentrated. The residue was purified by CC (Hept/EA 2:1, 1:1) to give the desired intermediate as a yellow solid (20.6 g, 40% yield) which was used as such in the next step.
MS (ESI, m/z): 383.2 [M+H$^+$].

L.ii. 6-{(S)-5-[2-(tert-butyl-dimethyl-silanyloxy)-ethyl]-2-oxo-oxazolidin-3-yl}-4H-benzo[1,4]thiazin-3-one Starting with intermediate L.i (20.0 g, 52.2 mmol) and using procedure B, the title intermediate was obtained as a beige solid (18.2 g, 85% yield).

$^1$H NMR (CDCl$_3$) δ: 8.39 (s, 1H), 7.40 (d, J=2.3 Hz, 1H), 7.28 (m, 1H), 6.95 (dd, J=8.5, 2.3 Hz, 1H), 4.83 (m, 1H), 4.08 (t, J=8.8 Hz, 1H), 3.79 (m, 4H), 3.41 (s, 2H), 2.01 (m, 2H), 0.90 (m, 9H), 0.07 (d, J=2.9 Hz, 6H).

L.iii. 6-[(S)-5-(2-hydroxy-ethyl)-2-oxo-oxazolidin-3-yl]-4H-benzo[1,4]thiazin-3-one Starting with intermediate L.ii (18.0 g, 44 mmol) and using procedure F, the title intermediate was obtained as an off-white solid (7.6 g, 60% yield).

MS (ESI, m/z): 295.5 [M+H$^+$].

L.iv. Methanesulfonic acid 2[(S)-2-oxo-3-(3-oxo-3,4-dihydro-2H-benzo[1,4]thiazin-6-yl)-oxazolidin-5-yl]-ethyl ester Starting with intermediate L.iii (3.0 g, 10.2 mmol) and using procedure D, the title intermediate was obtained as a beige solid (3.6 g, 96% yield).

$^1$H NMR (DMSO-d6) δ: 10.56 (s, 1H), 7.31 (m, 2H), 7.07 (dd, J=8.8, 2.3 Hz, 1H), 4.78 (dd, J=8.2, 6.7 Hz, 1H), 4.34 (td, J=6.2, 2.9 Hz, 2H), 4.12 (t, J=8.5 Hz, 1H), 3.73 (dd, J=8.8, 7.0 Hz, 1H), 3.42 (s, 2H), 3.28 (s, 3H), 2.17 (q, J=6.4 Hz, 2H).

MS (ESI, m/z): 373.3 [M+H$^+$].

Intermediate M rac-methanesulfonic acid 2-[3-(2,3-dihydro-[1,4]dioxino[2,3-c]pyridin-7-yl)-2-oxo-oxazolidin-5-yl]-ethyl ester

M.i. (2,3-dihydro-[1,4]dioxino[2,3-c]pyridin-7-yl)-carbamic acid tert-butyl ester A suspension of 2,3-dihydro-1,4-dioxino[2,3-c]pyridine-7-carboxylic acid (3.2 g; prepared according to WO 03/042210), TEA (3 mL) and DPPA (4.6 mL) in t-BuOH was stirred at 80° C. overnight. The solvent was evaporated under reduced pressure and the residue was partitioned between EA and water. The org. phase was washed with brine, dried over MgSO$_4$ and evaporated under reduced pressure. The residue was crystallized from ether, affording a beige solid (2.9 g; 65% yield).

$^1$H NMR (CDCl$_3$) δ: 7.95 (s, 1H), 7.84 (s, 1H), 7.49 (s, 1H), 4.31 (m, 2H), 4.23 (m, 2H), 1.52 (s, 9H).

M.ii. rac-5-[2-(tert-butyl-dimethyl-silanyloxy)-ethyl]-3-(2,3-dihydro-[1,4]dioxino[2,3-c]pyridin-7-yl)-oxazolidin-2-one A solution of intermediate M.i (3.3 g) and 2-[2-[[(tert-butyl)dimethylsilyl]oxy]ethyl]-oxirane (2.65 g; prepared according to WO 2007/144423) in DMF (40 mL) was cooled to 0° C. and treated with a solution of lithium tert-butoxide (2.2M in THF, 17.8 mL). The reaction mixture was allowed to reach rt and further stirred at 80° C. for 2 days. The reaction mixture was partitioned between EA and water. The org. phase was washed with brine, dried over MgSO$_4$ and concentrated under reduced pressure. The residue was purified by CC (Hex-EA 2:1 to 1:1), affording a yellow oil (2.7 g, 54% yield).

MS (ESI, m/z): 381.0 [M+H$^+$].

M.iii. rac-3-(2,3-dihydro-[1,4]dioxino[2,3-c]pyridin-7-yl)-5-(2-hydroxy-ethyl)-oxazolidin-2-one A suspension of intermediate M.ii (2.7 g, 7.3 mmol) in THF (40 mL) was treated with a solution of TBAF (1M in THF; 7.5 mL) and further stirred at rt for 2.5 h. The reaction mixture was partitioned between EA and 33% aq. NH$_4$OH. The org. phase was washed with brine, dried over MgSO$_4$ and evaporated under reduced pressure. The residue was crystallized from ether, affording a yellow solid (1.1 g, 58% yield).

$^1$H NMR (CDCl$_3$) δ: 7.74 (d, J=8.5 Hz, 1H) 7.24 (d, J=8.5 Hz, 1H), 4.83 (m, 1H), 4.43 (m, 2H), 4.28 (m, 4H), 3.88 (m, 3H), 2.03 (m, 2H).

MS (ESI, m/z): 267.1 [M+H$^+$].

M.iv. rac-methanesulfonic acid 2-[3-(2,3-dihydro-[1,4]dioxino[2,3-c]pyridin-7-yl)-2-oxo-oxazolidin-5-yl]-ethyl ester Starting from intermediate M.iii (1.0 g) and following procedure D, the title compound was obtained as a beige solid (1.3 g; 100% yield).

MS (ESI, m/z): 345.2 [M+H$^+$].

Intermediate N rac-methanesulfonic acid 2-[3-(2,3-dihydro-[1,4]dioxino[2,3-b]pyridin-6-yl)-2-oxo-oxazolidin-5-yl]-ethyl ester

N.i. (2,3-dihydro-[1,4]dioxino[2,3-b]pyridin-6-yl)-carbamic acid benzyl ester Starting from 2,3-dihydro-1,4-dioxino[2,3-b]pyridin-6-amine (2.7 g; prepared according to *Chemische Berichte* (1990), 123(12), 2453-2454) and following procedure C, the title compound was obtained as a beige solid (5.3 g; 100% yield).

$^1$H NMR (CDCl$_3$) δ: 7.50 (d, J=8.5 Hz, 1H), 7.35 (m, 5H), 7.22 (m, 2H), 5.19 (s, 2H), 4.37 (m, 2H), 4.19 (m, 2H).

N.ii. rac-5-[2-(tert-butyl-dimethyl-silanyloxy)-ethyl]-3-(2,3-dihydro-[1,4]dioxino[2,3-b]pyridin-6-yl)-oxazolidin-2-one Starting from intermediate N.i (3.0 g) and 2-[2-[[(tert-butyl)dimethylsilyl]oxy]ethyl]-oxirane (2.12 g; prepared according to WO 2007/144423) and following procedure A, the title compound was obtained as a brown oil (2.9 g; 73% yield).

MS (ESI, m/z): 380.1 [M+H$^+$].

N.iii. rac-3-(2,3-dihydro-[1,4]dioxino[2,3-b]pyridin-6-yl)-5-(2-hydroxy-ethyl)-oxazolidin-2-one Starting from intermediate N.ii (2.8 g) and following procedure F, the title compound was obtained as a yellow solid (1.1 g; 56% yield).

MS (ESI, m/z): 266.8 [M+H$^+$].

N.iv. rac-methanesulfonic acid 2-[3-(2,3-dihydro-[1,4]dioxino[2,3-b]pyridin-6-yl)-2-oxo-oxazolidin-5-yl]-ethyl ester Starting from intermediate N.iii (1.0 g) and following procedure D, the title compound was obtained as a beige solid (1.24 g; 96% yield).

$^1$H NMR (CDCl$_3$) δ: 7.71 (d, J=8.8 Hz, 1H), 7.24 (d, J=8.8 Hz, 1H), 4.80 (m, 1H), 4.43 (m, 4H), 4.33 (m, 1H), 4.23 (m, 2H), 3.89 (m, 1H), 3.04 (s, 3H), 2.20 (m, 2H).

Intermediate O methanesulfonic acid 2-[(R)-3-(4-ethoxy-phenyl)-2-oxo-oxazolidin-5-yl]-ethyl ester

O.i. (R)-4-(tert-butyl-dimethyl-silanyloxy)-1-(4-ethoxy-phenylamino)-butan-2-ol Starting from 4-ethoxyaniline (3.2 mL; commercial) and tert-butyl-dimethyl-((R)-2-oxiranyl-ethoxy)-silane (5.0 g; prepared according to WO 2007/144423) and following procedure A, the title compound was obtained after CC (EA/Hept 1:1) as a brown oil (5.22 g; 62% yield).

MS (ESI, m/z): 340.2 [M+H$^+$].

O.ii. (R)-5-[2-(tert-butyl-dimethyl-silanyloxy)-ethyl]-3-(4-ethoxy-phenyl)-oxazolidin-2-one Starting from intermediate O.i (5.2 g) and following procedure B, the title compound was obtained as an off-white solid (4.3 g; 76.5% yield).

MS (ESI, m/z): 366.1 [M+H$^+$].

O.iii. (R)-3-(4-ethoxy-phenyl)-5-(2-hydroxy-ethyl)-oxazolidin-2-one

Starting from intermediate O.ii (4.3 g) and following procedure F, the title compound was obtained as an off-white solid (1.53 g; 52%).

MS (ESI, m/z): 251.9 [M+H$^+$].

O.iv. Methanesulfonic acid 2-[(R)-3-(4-ethoxy-phenyl)-2-oxo-oxazolidin-5-yl]-ethyl ester Starting from intermediate O.iii (1.5 g) and following procedure D (using however 1.5 eq. Ms$_2$O instead of 1.1 eq. of MsCl), the title compound was obtained as an off-white solid (1.89 g; 96% yield).

MS (ESI, m/z): 330.0 [M+H$^+$].

PREPARATION OF FINAL COMPOUNDS

Example 1

6-((R)-5-{[3-(7-methoxy-2-oxo-2H-quinolin-1-yl)-propylamino]-methyl}-2-oxo-oxazolidin-3-yl)-4H-benzo[1,4]thiazin-3-one

1.i. 3-(7-methoxy-2-oxo-2H-quinolin-1-yl)-propionic acid ethyl ester

The compound was obtained according to procedure H starting from 7-methoxy-2(1H)-quinolinone (614 mg, 3.5 mmol) and ethyl acrylate (0.4 mL). The crude brown oil (0.96 g; 100% yield) was used as such in the next step.

$^1$H NMR (DMSO-d6) δ: 7.81 (d, J=9.4 Hz, 1H), 7.63 (d, J=8.5 Hz, 1H), 6.99 (d, J=2.3 Hz, 1H), 6.88 (dd, J=8.8, 2.3 Hz, 1H), 6.39 (d, J=9.4 Hz, 1H), 4.45 (m, 2H), 4.03 (q, J=7.0 Hz, 2H), 3.88 (s, 3H), 2.62 (m, 2H), 1.13 (t, J=7.0 Hz, 3H).

MS (ESI, m/z): 276.3 [M+H$^+$].

1.ii. 3-(7-methoxy-2-oxo-2H-quinolin-1-yl)-propionaldehyde

The compound was obtained according to procedure J starting from intermediate 1.i (402 mg, 1.46 mmol) and DIBAH (2.6 mL, 4.38 mmol, 3 eq., solution ~1.7M in toluene). The crude product was purified by CC (Hept/EA 1:1, to EA containing 1% of NH$_4$OH), affording 104 mg of an orange oil (31% yield).

$^1$H NMR (DMSO-d6) δ: 9.72 (t, J=1.8 Hz, 1H), 7.81 (d, J=9.4 Hz, 1H), 7.64 (d, J=8.8 Hz, 1H), 6.98 (d, J=2.3 Hz, 1H), 6.89 (dd, J=8.8, 2.3 Hz, 1H), 6.39 (d, J=9.4 Hz, 1H), 4.50 (t, J=7.0 Hz, 2H), 3.88 (s, 3H), 2.78 (td, J=7.0, 1.8 Hz, 2H).

MS (EST, m/z): 232.2 [M+H$^+$].

1.iii. 6-((R)-5-{[3-(7-methoxy-2-oxo-2H-quinolin-1-yl)-propylamino]-methyl}-2-oxo-oxazolidin-3-yl)-4H-benzo[1,4]thiazin-3-one The compound was obtained according to procedure I starting from intermediate 1.ii (60 mg, 0.26 mmol) and intermediate B (73 mg, 0.26 mmol). The product was purified by CC (EA/MeOH 9:1 to 4:1 containing 1% of NH$_4$OH), affording 24 mg (19% yield) of a colourless foam.

$^1$H NMR (DMSO-d6) δ: 10.53 (m, 1H), 7.79 (d, J=9.4 Hz, 1H), 7.62 (d, J=8.5 Hz, 1H), 7.30 (m, 2H), 7.10 (m, 1H), 6.99 (dd, J=1.2, 0.6 Hz, 1H), 6.87 (m, 1H), 6.39 (d, J=9.4 Hz, 1H), 4.72 (m, 1H), 4.25 (m, 2H), 4.04 (m, 1H), 3.82 (m, 4H), 3.41 (s, 2H), 2.83 (m, 2H), 2.63 (m, 3H), 1.75 (m, 2H).

MS (ESI, m/z): 495.1 [M+H$^+$].

Example 2

6-((R))-5-{[3-(7-bromo-2-oxo-2H-quinolin-1-yl)-propylamino]-methyl}-2-oxo-oxazolidin-3-yl)-4H-benzo[1,4]thiazin-3-one

2.i. 3-(7-bromo-2-oxo-2H-quinolin-1-yl)-propionic acid ethyl ester

The compound was obtained according to procedure H starting from 7-bromoquinolin-2(1H)-one (commercial; 561 mg, 2.5 mmol) and ethyl acrylate (0.27 mL, 2.5 mmol, 1 eq.). The crude orange oil (0.76 g; 94% yield) was used as such in the next step.

$^1$H NMR (DMSO-d6) δ: 7.90 (d, J=9.7 Hz, 1H), 7.83 (d, J=1.8 Hz, 1H), 7.66 (m, 1H), 7.43 (dd, J=8.2, 1.5 Hz, 1H), 6.61 (d, J=9.4 Hz, 1H), 4.44 (m, 2H), 4.03 (q, J=7.3 Hz, 2H), 2.61 (m, 2H), 1.14 (t, J=7.0 Hz, 3H).

MS (ESI, m/z): 326.0 [M+H$^+$].

2.ii 3-(7-bromo-2-oxo-2H-quinolin-1-yl)-propionaldehyde

The compound was obtained according to procedure J starting from intermediate 2.i (444 mg, 1.37 mmol). The crude product was purified by CC (Hept/EA 2:1 to 1:1 to EA containing 1% NH$_4$OH), affording an orange solid (178 mg, 46% yield).

¹H NMR (DMSO-d6) δ: 9.71 (s, 1H), 7.88 (m, 2H), 7.67 (d, J=8.2 Hz, 1H), 7.43 (m, 1H), 6.61 (d, J=9.7 Hz, 1H), 4.48 (t, J=7.3 Hz, 2H), 2.76 (m, 2H).
MS (ESI, m/z): 280.2 [M+H⁺].

2.iii. 6-((R)-5-{[3(7-bromo-2-oxo-2H-quinolin-1-yl)-propylamino]methyl}-2-oxo-oxazolidin-3-yl)-4H-benzo[1,4]thiazin-3-one The compound was obtained according to procedure I starting from intermediate 2.ii (100 mg, 0.357 mmol) and intermediate B (100 mg, 0.357 mmol). The crude product was purified by CC (EA/MeOH 9:1, 4:1 containing 1% NH₄OH), affording a colourless solid. (50 mg, 26% yield).
¹H NMR (DMSO-d6) δ: 10.53 (s, 1H), 7.89 (d, 7=9.4 Hz, 1H), 7.81 (d, 7=1.8 Hz, 1H), 7.66 (d, J=8.5 Hz, 1H), 7.41 (dd, J=8.2, 1.5 Hz, 1H), 7.30 (m, 2H), 7.10 (dd, J=8.8, 2.3 Hz, 1H), 6.61 (d, J=9.4 Hz, 1H), 4.74 (m, 1H), 4.24 (m, 2H), 4.06 (t, J=8.8 Hz, 1H), 3.80 (dd, 7=8.8, 6.7 Hz, 1H), 3.41 (s, 2H), 2.83 (d, J=5.3 Hz, 2H), 2.62 (t, J=6.7 Hz, 2H), 1.73 (m, 2H).
MS (ESI, m/z): 545.1 [M+H⁺].

Example 3

1-(3-{[(R)-3-(2,3-dihydro-benzo[1,4]dioxin-6-yl)-2-oxo-oxazolidin-5-ylmethyl]-amino}-propyl)-7-methoxy-1H-quinolin-2-one The compound was obtained according to procedure I starting from intermediate 1.ii and the intermediate amine A. The crude product was purified by CC (EA/MeOH 9:1 containing 1% NH₄OH), affording a colourless foam (680 mg, 72% yield).
¹H NMR (DMSO-d6) δ: 7.79 (d, J=9.4 Hz, 1H), 7.62 (d, J=9.1 Hz, 1H), 7.10 (s, 1H), 6.97 (m, 2H), 6.85 (m, 2H), 6.39 (d, J=9.7 Hz, 1H), 4.67 (m, 1H), 4.23 (m, 6H), 4.02 (t, J=9.1 Hz, 1H), 3.84 (s, 3H), 3.78 (m, 1H), 2.81 (m, 2H), 2.63 (m, 2H), 1.74 (m, 2H).
MS (ESI, m/z): 465.9 [M+H⁺].

Example 4

7-bromo-1-(3-{[(R)-3-(2,3-dihydro-benzo[1,4]dioxin-6-yl)-2-oxo-oxazolidin-5-ylmethyl]-amino}-propyl)-1H-quinolin-2-one The compound was obtained according to procedure I starting from intermediate 2.ii (0.357 mmol) and the intermediate amine A. The crude product was purified by CC (EA/MeOH 9:1 containing 1% NH₄OH), affording a colourless foam (104 mg, 57% yield).
¹H NMR (DMSO-d6) δ: 7.89 (m, 1H), 7.82 (m, 1H), 7.66 (m, 1H), 7.42 (m, 1H), 7.10 (dd, J=1.5, 0.6 Hz, 1H), 6.95 (m, 1H), 6.83 (m, 1H), 6.61 (m, 1H), 4.70 (m, 1H), 4.22 (m, 6H), 4.04 (m, 1H), 3.79 (m, 1H), 2.81 (m, 2H), 2.61 (m, 2H), 1.73 (m, 2H).
MS (ESI, m/z): 516.0 [M+H⁺].

Example 5

(RS)-6-(5-{2-[3-(7-methoxy-2-oxo-2H-quinolin-1-yl)-azetidin-1-yl]-ethyl}-2-oxo-oxazolidin-3-yl)-4H-benzo[1,4]thiazin-3-one 5.i. 3-(7-methoxy-2-oxo-2H-quinolin-1-yl)-azetidine-1-carboxylic acid tert-butyl ester A mixture of 7-methoxy-2(1H)-quinolinone (commercial; 290 mg; 1.65 mmol) and tert-butyl 3-iodo-1-azetidinecarboxylate (commercial; 391 mg; 1.38 mmol) and Cs₂CO₃ (613 mg; 1.88 mmol) in DMF (2 mL) was heated at 80° C. for 4 h. The reaction mixture was diluted with water and extracted with EA. The combined org. layers were washed with water and brine, dried over MgSO₄, concentrated under reduced pressure and purified by CC (Hept/EA 1:1), affording a pale yellow oil (271 mg, 65% yield).
MS (ESI, m/z): 331.3 [M+H⁺].

5.ii. 1-azetidin-3-yl-7-methoxy-M-quinolin-2-one

The compound was obtained according to procedure E starting from intermediate 5.i. The crude product was purified by CC (DCM/MeOH/NH₄OH 1000:100:8), affording a colourless oil (137 mg, 73% yield).
MS (ESI, m/z): 231.4 [M+H⁺].

5.iii. (RS)-6-(5-{2-[3-(7-methoxy-2-oxo-2H-quinolin-1-yl)-azetidin-1-yl]-ethyl}-2-oxo-oxazolidin-3-yl)-4H-benzo[1,4]thiazin-3-one A solution of intermediate 5.ii (68 mg; 0.3 mmol) and intermediate D (110 mg; 1 eq.) and DIPEA (56 μL; 1.1 eq.) in DMSO (1 mL) was stirred at 70° C. for 2 days. The reaction mixture was diluted with EA and the aq. layer was concentrated under reduced pressure and purified by HPLC, affording 30 mg (20% yield) of a yellow solid.
¹H NMR (DMSO d6) δ: 10.66 (s, 1H), 8.42 (s, 1H), 8.34 (m, 1H), 7.94 (d, J=8.8 Hz, 1H), 7.34 (m, 3H), 7.22 (dd, J=8.5, 1.8 Hz, 1H), 7.08 (m, 1H), 4.85 (m, 1H), 4.52 (m, 2H), 4.28 (m, 1H), 4.11 (m, 1H), 3.97 (m, 3H), 3.95-3.58 (m, 5H), 3.42 (s, 2H), 2.17 (m, 2H).
MS (ESI, m/z): 506.9 [M+H÷].

Example 6

3-(7-methoxy-2-oxo-2H-quinoxalin-1-yl)-N-[(R)-2-oxo-3-(3-oxo-3,4-dihydro-2H-benzo[1,4]thiazin-6-yl)-oxazolidin-5-ylmethyl]-propionamide 6.i. 3-(7-methoxy-2-oxo-2H-quinoxalin-1-yl)-propionic acid ethyl ester The compound was obtained according to procedure H starting from 7-methoxyquinolin-2(1H)-one (commercial; 617 mg, 3.5 mmol) and ethyl acrylate (0.4 mL, 3.5 mmol, 1 eq.). The crude oil was purified by CC (EA), affording 644 mg (67% yield) of a brown oil.
¹H NMR (DMSO-d6) δ: 8.02 (s, 1H), 7.73 (d, J=8.8 Hz, 1H), 7.06 (d, J=2.6 Hz, 1H), 6.98 (dd, J=8.8, 2.3 Hz, 1H), 4.44 (t, J=7.3 Hz, 2H), 4.03 (q, J=7.3 Hz, 2H), 3.90 (s, 3H), 2.67 (t, J=7.6 Hz, 2H), 1.12 (t, J=7.6 Hz, 3H).
MS (ESI, m/z): 277.2 [M+H⁺].

6.ii. 3-(7-methoxy-2-oxo-2H-quinoxalin-1-yl)-propionic acid

The compound was obtained according to procedure K starting from intermediate 6.i. The crude filtrate was concentrated under reduced pressure, affording an orange solid (267 mg, 98% yield).
¹H NMR (DMSO-d6) δ: 12.41 (m, 1H), 8.02 (s, 1H), 7.73 (d, J=9.1 Hz, 1H), 7.08 (d, J=2.6 Hz, 1H), 6.98 (dd, J=8.8, 2.6 Hz, 1H), 4.41 (m, 2H), 3.90 (s, 3H), 2.60 (m, 2H).
MS (ESI, m/z): 249.4 [M+H⁺].

6.iii. 3-(7-methoxy-2-oxo-2H-quinoxalin-1-yl)-N-[(R)-2-oxo-3-(3-oxo-3,4-dihydro-2H-benzo[1,4]thiazin-6-yl)-oxazolidin-5-ylmethyl]-propionamide The compound was obtained according to procedure L starting from intermediate 6.ii (63 mg, 0.25 mmol, 1 eq.) and intermediate B (70 mg, 0.25 mmol, 1 eq.). The yield was 25 mg (20%; orange solid)

$^1$H NMR (DMSO-d6) δ: 10.55 (s, 1H), 8.40 (m, 1H), 8.00 (s, 1H), 7.72 (d, J=9.1 Hz, 1H), 7.29 (m, 2H), 7.01 (m, 3H), 4.66 (m, 1H), 4.38 (m, 2H), 4.00 (m, 1H), 3.89 (s, 3H), 3.65 (m, 1H), 3.40 (m, 4H), 2.51 (m, 2H).
MS (ESI, m/z): 509.9 [M+H$^+$].

Example 7

N-[(R)-3-(2,3-dihydro-benzo[1,4]dioxin-6-yl)-2-oxo-oxazolidin-5-ylmethyl]-3-(7-methoxy-2-oxo-2H-quinolin-1-yl)-propionamide

7.i. N-[(R)-3-(2,3-dihydro-benzo[1,4]dioxin-6-yl)-2-oxo-oxazolidin-5-ylmethyl]-acrylamide A solution of intermediate A (1 g, 4 mmol) in DCM (19 mL) was cooled to 0° C. and sequentially treated with TEA (0.62 mL, 4.4 mmol, 1.1 eq.) and a solution of acryloyl chloride (0.33 ml, 4 mmol, 1 eq.) in DCM (1 mL). The reaction mixture was further stirred at rt for 12 h. The solution was diluted with DCM, sequentially washed with diluted HCl and brine, dried over Na$_2$SO$_4$ and concentrated under reduced pressure. The crude product was purified by CC (EA, EA/MeOH 19:1 containing 1% of NH$_4$OH), affording 1.033 g (85% yield) of a colourless foam $^1$H NMR (DMSO-d6) δ: 8.45 (m, 1H), 7.07 (d, J=2.6 Hz, 1H), 6.92 (m, 1H), 6.25 (m, 1H), 6.83 (m, 1H), 6.09 (m, 1H), 5.60 (dd, J=10.0, 2.3 Hz, 1H), 4.70 (m, 1H), 4.20 (m, 4H), 4.05 (t, J=9.1 Hz, 1H), 3.67 (dd, J=9.1, 6.2 Hz, 1H), 3.48 (t, J=5.6 Hz, 2H).

7.ii. N-[(R)-3-(2,3-dihydro-benzo[1,4]dioxin-6-yl)-2-oxo-oxazolidin-5-ylmethyl]-3-(7-methoxy-2-oxo-2H-quinolin-1-yl-propionamide The compound was obtained according to procedure H starting from intermediate 7.i (183 mg, 0.6 mmol, 1.05 eq.) and 7-methoxy-2(1H)-quinolinone (100 mg, 0.57 mmol). The crude product was purified by CC (EA/MeOH 9:1 containing 1% of NH$_4$OH), affording 47 mg of a colourless foam (17% yield).

$^1$H NMR (DMSO-d6) δ: 8.39 (t, J=5.6 Hz, 1H), 7.79 (d, J=9.4 Hz, 1H), 7.61 (d, J=8.8 Hz, 1H), 7.04 (m, 2H), 6.87 (m, 3H), 6.39 (d, J=9.4 Hz, 1H), 4.63 (m, 1H), 4.39 (t, J=7.3 Hz, 2H), 4.20 (m, 4H), 3.97 (m, 1H), 3.86 (s, 3H), 3.63 (dd, J=9.1, 6.4 Hz, 1H), 3.39 (t, J=5.6 Hz, 2H), 2.49 (m, 2H).
MS (ESI, m/z): 480.3 [M+H$^+$].

Example 8

3-(7-bromo-2-oxo-2H-quinolin-1-yl)-N-[(R)-3-(2,3-dihydro-benzo[1,4]dioxin-6-yl)-2-oxo-oxazolidin-5-ylmethyl]-propionamide

8.i. 3-(7-bromo-2-oxo-2H-quinolin-1-yl)-propionic acid

The compound (colourless solid; 166 mg, 91% yield) was obtained according to procedure K starting from intermediate 2.i (200 mg, 0.62 mmol).

$^1$H NMR (DMSO-d6) δ: 7.90 (d, J=9.7 Hz, 1H), 7.84 (d, J=1.2 Hz, 1H), 7.66 (d, J=8.2 Hz, 1H), 7.43 (dd, J=8.2, 1.8 Hz, 1H), 6.62 (d, J=9.7 Hz, 1H), 4.40 (m, 2H), 2.54 (m, 2H).
MS (ESI, m/z): 296.4 [M+H$^+$].

8.ii. 3-(7-bromo-2-oxo-2H-quinolin-1-yl)-N-[(R)-3-(2,3-dihydro-benzo[1,4]dioxin-6-yl)-2-oxo-oxazolidin-5-ylmethyl]-propionamide The compound (colourless solid; 82 mg, 62% yield) was obtained according to procedure L starting from intermediate 8.i. (75 mg, 0.25 mmol, 1 eq.) and intermediate A (63 mg, 0.25 mmol, 1 eq.).

$^1$H NMR (DMSO-d6) δ: 8.39 (m, 1H), 7.88 (m, 1H), 7.77 (s, 1H), 7.65 (m, 1H), 7.41 (m, 1H), 7.06 (m, 1H), 6.91 (m, 1H), 6.83 (m, 1H), 6.60 (d, J=9.7 Hz, 1H), 4.64 (m, 1H), 4.37 (m, 2H), 4.20 (m, 4H), 3.98 (m, 1H), 3.63 (m, 1H), 3.39 (m, 2H), 2.45 (m, 2H).
MS (ESI, m/z): 528.3 [M+H$^+$].

Example 9

3-(7-bromo-2-oxo-2H-quinolin-1-yl)-N-[(R)-2-oxo-3-(3-oxo-3,4-dihydro-2H-benzo[1,4]thiazin-6-yl)-oxazolidin-5-ylmethyl]-propionamide The compound (colourless solid; 43 mg, 31% yield) was obtained according to procedure L starting from intermediate 8.i (1 eq.) and intermediate B (1 eq.).

$^1$H NMR (DMSO-d6) δ: 10.55 (s, 1H), 8.41 (s, 1H), 7.88 (d, J=9.4 Hz, 1H), 7.77 (d, J=1.2 Hz, 1H), 7.65 (d, J=8.5 Hz, 1H), 7.42 (dd, J=8.2, 1.8 Hz, 1H), 7.29 (m, 2H), 7.05 (dd, J=8.5, 2.1 Hz, 1H), 6.60 (d, J=9.7 Hz, 1H), 4.69 (m, 1H), 4.37 (t, J=7.6 Hz, 2H), 4.02 (t, J=9.1 Hz, 1H), 3.66 (dd, J=9.4, 6.7 Hz, 1H), 3.41 (m, 4H), 2.49 (m, 2H).
MS (ESI, m/z): 559.1 [M+H$^+$].

Example 10

N-[(R)-3-(2,3-dihydro-benzo[1,4]dioxin-6-yl)-2-oxo-oxazolidin-5-ylmethyl]-3-(7-methoxy-2-oxo-2H-quinoxalin-1-yl)-propionamide The compound (orange solid; 57 mg, 47% yield) was obtained according to procedure L starting from intermediates 6.ii (1 eq.) and intermediate A (1 eq.).

$^1$H NMR (DMSO-d6) δ: 8.39 (m, 1H), 8.01 (s, 1H), 7.72 (d, J=8.8 Hz, 1H), 7.06 (m, 2H), 6.97 (m, 1H), 6.87 (m, 2H), 4.61 (m, 1H), 4.38 (m, 2H), 4.20 (m, 4H), 3.95 (m, 1H), 3.89 (s, 3H), 3.62 (m, 1H), 3.37 (m, 2H), 2.53 (m, 2H).
MS (ESI, m/z): 481.2 [M+H$^+$].

Example 11

3-(7-methoxy-2-oxo-2H-quinolin-1-yl)-N-[(R)-2-oxo-3-(3-oxo-3,4-dihydro-2H-benzo[1,4]thiazin-6-yl)-oxazolidin-5-ylmethyl]-propionamide

11.i. 3-(7-methoxy-2-oxo-2H-quinolin-1-yl)-propionic acid

The compound (yellow solid; 0.319 g, 88% yield) was obtained according to procedure K starting from intermediate 1.i. (0.402 g, 1.46 mmol).

$^1$H NMR (DMSO-d6) δ: 12.37 (m, 1H), 7.81 (d, J=9.4 Hz, 1H), 7.63 (d, J=8.8 Hz, 1H), 7.01 (d, J=2.3 Hz, 1H), 6.88 (dd, J=8.8, 2.3 Hz, 1H), 6.40 (d, J=9.4 Hz, 1H), 4.42 (m, 2H), 3.88 (s, 3H), 2.55 (m, 2H).
MS (ESL m/z): 248.2 [M+H$^+$].

11.ii. 3-(7-methoxy-2-oxo-2H-quinolin-1-yl)-N-[(R)-2-oxo-3-(3-oxo-3,4-dihydro-2H-benzo[1,4]thiazin-6-yl)-oxazolidin-5-ylmethyl]-propionamide The compound (colourless solid; 63 mg, 50% yield) was obtained according to procedure L starting from intermediates B and 11.i.

$^1$H NMR (DMSO-d6) δ: 10.55 (s, 1H), 8.40 (m, 1H), 7.79 (d, J=9.4 Hz, 1H), 7.62 (d, J=8.5 Hz, 1H), 7.30 (m, 2H), 7.04 (m, 2H), 6.87 (dd, J=8.8, 2.3 Hz, 1H), 6.38 (d, J=9.4 Hz, 1H), 4.68 (m, J=5.0, 5.0, 2.9, 0.6 Hz, 1H), 4.38 (m, 2H), 4.01 (t, J=8.8 Hz, 1H), 3.86 (s, 3H), 3.67 (dd, J=9.1, 6.7 Hz, 1H), 3.42 (m, 4H), 2.50 (m, 2H).

MS (ESI, m/z): 509.0 [M+H$^+$].

Example 12

(RS)-2-amino-N-[(R)-3-(2,3-dihydro-benzo[1,4]dioxin-6-yl)-2-oxo-oxazolidin-5-ylmethyl]-3-(7-methoxy-2-oxo-2H-quinoxalin-1-yl)-propionamide

12.i. (RS)-2-tert-butoxycarbonylamino-3-(7-methoxy-2-oxo-2H-quinoxalin-1-yl)-propionic acid methyl ester The compound (yellow solid; 370 mg, 20% yield) was obtained according to procedure H starting from 7-methoxyquinoxalin-2(1H)-one (prepared according to WO 2006/134378) and N-(tert-butoxycarbonyl)dehydroalanine methyl ester.

MS (EST, m/z): 378.2 [M+H$^+$].

12.ii. (RS)-2-tert-butoxycarbonylamino-3-(7-methoxy-2-oxo-2H-quinoxalin-1-yl)-propionic acid A solution of intermediate 12.i (370 mg, 0.98 mmol) in THF/H$_2$O (5:1; 6 mL) was treated with LiOH (83 mg, 2 mmol, 2 eq.) and further stirred at rt for 7 h. The reaction mixture was partially concentrated under reduced pressure and the residue was diluted with water and acidified to pH 3 with HCl. The resulting solid was collected by filtration and washed with water and ether, affording, after drying, 231 mg (65% yield) of a pink solid.

$^1$H NMR (DMSO-d6) δ: 13.01 (m, 1H), 8.01 (s, 1H), 7.70 (d, J=8.8 Hz, 1H), 7.13 (d, J=2.3 Hz, 1H), 7.08 (d, J=8.5 Hz, 1H), 6.96 (dd, J=8.8, 2.3 Hz, 1H), 4.49 (m, 3H), 3.90 (s, 3H), 1.13 (s, 9H).

MS (ESI, m/z): 364.3 [M+H$^+$].

12.iii. (RS)-[1-{[(R)-3-(2,3-dihydro-benzo[1,4]dioxin-6-yl)-2-oxo-oxazolidin-5-ylmethyl]-carbamoyl}-2-(7-methoxy-2-oxo-2H-quinoxalin-1-yl)-ethyl]-carbamic acid tert-butyl ester The compound was obtained according to procedure L starting from intermediate 12.ii (102 mg, 0.28 mmol, 1 eq.) and intermediate A (71 mg, 0.28 mmol, 1 eq.). The crude product was purified by CC (EA), affording 149 mg (89% yield) of a yellow solid.

MS (ESI, m/z): 596.2 [M+H$^+$].

12.iv. (RS)-2-amino-N-[(R)-3-(2,3-dihydro-benzo[1,4]dioxin-6-yl)-2-oxo-oxazolidin-5-ylmethyl]-3-(7-methoxy-2-oxo-2H-quinoxalin-1-yl)-propionamide The compound was obtained according to procedure E starting from intermediate 12.iii (148 mg, 0.25 mmol). The crude product was purified by CC (EA/MeOH 19:1 to 9:1 to 4:1 containing 1% of NH$_4$OH), affording 84 mg (68% yield) of an orange solid.

MS (ESI, m/z): 496.4 [M+H$^+$].

Example 13

6-((R)-5-{[(R)-2-hydroxy-3-(7-methoxy-2-oxo-2H-quinolin-1-yl)-propylamino]-methyl}-2-oxo-oxazolidin-3-yl)-4H-benzo[1,4]oxazin-3-one hydrochloride

13.i. [(R)-2-hydroxy-3-(7-methoxy-2-oxo-2H-quinolin-1-yl)-propyl]-carbamic acid tert-butyl ester A solution of 7-methoxy-2(1H)-quinolinone (875 mg) and tert-butyl [(2R)-3-chloro-2-hydroxypropyl]carbamate (1.2 eq.) in DMF (1 mL) was treated with Cs$_2$CO$_3$ (1.63 g, 1 eq.) and heated at 75° C. for 1.5 h. After cooling to rt the mixture was partitioned between EA and water. The org. phase was washed with water and brine, dried over MgSO$_4$ and concentrated under reduced pressure. The residue was purified by CC (EA/Hept 2:1, EA) to afford the title intermediate (second eluting compound) as a yellowish foam (808 mg, 46% yield).

$^1$H NMR (CDCl$_3$) δ: 7.65 (d, J=9.4 Hz, 1H), 7.48 (d, J=8.8 Hz, 1H), 6.93 (m, 1H), 6.85 (dd, J=8.5, 2.3 Hz, 1H), 6.54 (d, J=9.1 Hz, 1H), 5.55 (br., 1H), 4.51 (m, 1H), 4.30 (m, 2H), 4.15 (m, 2H), 4.09 (m, 1H), 3.91 (s, 3H), 3.62 (m, 2H), 3.10 (m, 2H), 1.45 (m, 9H).

MS (ESI, m/z): 349.1 [M+H$^+$].

13.ii. 1-((R)-3-amino-2-hydroxy-propyl)-7-methoxy-1H-quinolin-2-one

The compound was obtained according to procedure E starting from intermediate 13.i (800 mg). The crude product was purified by CC (DCM/MeOH 9:1 containing 0.5% of NH$_4$OH), affording 272 mg (48% yield) of a yellowish solid.

$^1$H NMR (DMSO-d6) δ: 7.79 (d, J=9.4 Hz, 1H), 7.60 (d, J=8.5 Hz, 1H), 7.16 (d, J=2.3 Hz, 1H), 6.86 (dd, J=8.5, 2.3 Hz, 1H), 6.40 (d, J=9.4 Hz, 1H), 4.91 (br., 1H), 4.36 (dd, J=13.8, 5.9 Hz, 1H), 4.07 (dd, J=13.8, 6.4 Hz, 1H), 3.86 (s, 3H), 3.72 (m, 1H), 2.51 (m, 2H).

MS (ESI, m/z): 249.4 [M+H$^+$].

13.iii. 6-((R)-5-{[(R)-2-hydroxy-3-(7-methoxy-2-oxo-2H-quinolin-1-yl)-propylamino]-methyl}-2-oxo-oxazolidin-3-yl)-4H-benzo[1,4]oxazin-3-one hydrochloride A solution of intermediate 13.ii (124 mg; 0.5 mmol), intermediate C (171 mg; 0.5 mmol) and DIPEA (1.2 eq.) in DMSO (3 mL) was heated at 70° C. for 24 h. The mixture was partitioned between EA and water. The org. layer was washed with water and brine, dried over MgSO$_4$ and concentrated under reduced pressure. The residue was purified by CC (EA/MeOH 9:1 containing 1% of NH$_4$OH) affording 60 mg (24% yield) of a gum (free base). This material was dissolved in MeOH (0.5 mL) and DCM (0.5 mL), treated with 0.25 mL of 0.5M HCl in MeOH and precipitated by addition of 2 mL of ether. The resulting crystals were collected by filtration affording 25 mg (9% yield) of the title hydrochloride as a colourless solid.

MS (ESI, m/z): 495.1 [M+H$^+$].

Example 14

6-((R)-5-{[(R)-2-hydroxy-3-(7-methoxy-2-oxo-2H-quinolin-1-yl)-propylamino]-methyl}-2-oxo-oxazolidin-3-yl)-4H-benzo[1,4]thiazin-3-one hydrochloride This salt was prepared in analogy to Example 13, step 13.iii, starting from intermediate E (210 mg; 0.54 mmol) and intermediate 13.ii (124 mg; 0.5 mmol). 85 mg (31% yield) of a colourless solid were obtained.

$^1$H NMR (DMSO-d6) δ: 10.52 (s, 1H), 7.79 (d, J=9.4 Hz, 1H), 7.60 (d, J=8.5 Hz, 1H), 7.29 (m, 2H), 7.1.0 (m, 2H), 6.86 (dd, J=8.5, 2.1 Hz, 1H), 6.40 (d, J=9.4 Hz, 1H), 4.99 (d, J=5.3 Hz, 1H), 4.31 (s, 1H), 3.84 (s, 3H), 3.40 (s, 2H), 2.84 (m, 2H), 2.63 (m, 2H).

MS (ESI, m/z): 511.2 [M+H$^+$].

Example 15

6-((R)-5-{[(S)-2-hydroxy-3-(7-methoxy-2-oxo-2H-quinolin-1-yl)-propylamino]-methyl}-2-oxo-oxazolidin-3-yl)-4H-benzo[1,4]thiazin-3-one The compound was prepared in analogy to Example 13, steps 13.i to 13.iii, starting from tert-butyl [(2S)-3-chloro-2-hydroxypropyl]carbamate (commercial), intermediate E replacing however intermediate C in the final step and no dissolution of the free base and treatment with HCl being performed at the end of said step. A yellowish foam (105 mg, 41% yield) was obtained.

$^1$H NMR (DMSO-d6) δ: 10.52 (s, 1H), 7.79 (d, J=9.4 Hz, 1H), 7.60 (d, J=8.5 Hz, 1H), 7.29 (m, 2H), 7.10 (m, 2H), 6.86 (dd, J=8.5, 2.1 Hz, 1H), 6.40 (d, J=9.4 Hz, 1H), 4.99 (d, J=5.3 Hz, 1H), 4.31 (s, 1H), 3.84 (s, 3H), 3.40 (s, 2H), 2.84 (m, 2H), 2.63 (m, 2H).

MS (ESI, m/z): 511.2 [M+H$^+$].

Example 16

7-fluoro-6-((R)-5-{[(S)-2-hydroxy-3-(7-methoxy-2-oxo-2H-quinolin-1-yl)-propylamino]-methyl}-2-oxo-oxazolidin-3-yl)-4H-benzo[1,4]thiazin-3-one The compound was prepared in analogy to Example 13, steps 13.i to 13.iii, using intermediate F for the final step and no dissolution of the free base and treatment with HCl being performed at the end of said step. A beige foam (10 mg, 23% yield) was obtained.

$^1$H NMR (CDCl$_3$) δ: 9.18 (s, 1H), 7.69 (d, J=9.4 Hz, 1H), 7.51 (d, J=8.8 Hz, 1H), 7.33 (d, J=6.7 Hz, 1H), 7.08 (d, J=10.5 Hz, 1H), 6.97 (d, J=2.1 Hz, 1H), 6.86 (dd, J=8.8, 2.3 Hz, 1H), 6.74 (d, J=9.4 Hz, 1H), 4.84 (dd, J=3.8, 2.1 Hz, 1H), 4.57 (dd, J=14.6, 8.5 Hz, 1H), 4.32 (dd, J=14.6, 4.1 Hz, 1H), 4.18 (m, 2H), 3.88 (m, 5H), 3.43 (m, 1H), 3.34 (m, 1H), 3.15 (dd, J=13.5, 3.2 Hz, 1H), 3.03 (dd, J=12.3, 4.7 Hz, 1H), 2.84 (m, 2H).

MS (ESI, m/z): 529.3 [M+H$^+$].

Example 17

6-methoxy-4-(3-{[(R)-2-oxo-3-(3-oxo-3,4-dihydro-2H-benzo[1,4]thiazin-6-yl)-oxazolidin-5-ylmethyl]-amino}-propyl)-4H-pyrido[2,3-b]pyrazin-3-one 17.i. [3-(6-methoxy-3-nitro-pyridin-2-ylamino)-propyl]-carbamic acid tert-butyl ester A mixture of 2-chloro-6-methoxy-3-nitropyridine (5.9 g; commercial), N-(tert-butoxycarbonyl)-1,3-propanediamine (4.48 g; commercial) and K$_2$CO$_3$ (3.55 g) in MeCN (90 mL) and DMF (25 mL) was heated at 40° C. for 30 min. The reaction mixture was filtered and the filtrate was evaporated under reduced pressure. The residue was taken up in EA, sequentially washed with water and brine and evaporated under reduced pressure, affording 8.1 g (96% yield) of a crude yellow solid which was used in the next step without further purification.

MS (ESI, m/z): 327.4 [M+H$^+$].

17.ii. [3-(3-amino-6-methoxy-pyridin-2-ylamino)-propyl]-carbamic acid tert-butyl ester A solution of intermediate 17.i (8.1 g) in EtOH (170 mL) was hydrogenated over 10% Pd/C (2.6 g). After 4 h the catalyst was filtered off and the filtrate was evaporated under reduced pressure, affording 7.37 g (100% yield) of a dark brown oil which was used in the next step without further purification.

MS (ESI, m/z): 297.4 [M+H$^+$].

17.iii. [2-(3-tert-butoxycarbonylamino-propylamino)-6-methoxy-pyridin-3-ylamino]-acetic acid ethyl ester A solution of intermediate 17.ii (7.37 g) and ethyl bromoacetate (2.75 mL) in MeCN (130 mL) and DMF (65 mL) was stirred overnight at rt in presence of K$_2$CO$_3$ (6.87 g). The reaction mixture was filtered and the filtrate was evaporated under reduced pressure. The residue was taken up in EA/MeOH (19:1; 200 mL), sequentially washed with water and brine, dried over MgSO$_4$ and purified by CC (Hept/EA, 2:1 to 1:1), affording 5.69 g (60% yield) of a black oil.

MS (ESI, m/z): 383.2 [M+H$^+$].

17.iv. [3-(6-methoxy-3-oxo-3H-pyrido[2,3-b]pyrazin-4-yl)-propyl]-carbamic acid tert-butyl ester A solution of intermediate 17.iii (5.69 g) in toluene (350 mL) containing AcOH (1 mL) was refluxed for one day. The resulting solution was diluted with DCM (300 mL), treated with MnO$_2$ (24 g) and further stirred overnight. The suspension was filtered, the filtrate was evaporated under reduced pressure and purified by CC (Hept/EA 2:1 to 1:2) affording a brown oil (4.02 g; 81% yield).

MS (ESI, m/z): 335.1 [M+H$^+$].

17.v. 4-(3-amino-propyl)-6-methoxy-4H-pyrido[2,3-b]pyrazin-3-one

Intermediate 17.iv (1.7 g) was deprotected according to procedure E to give the desired amine as a brown solid (85% yield).

MS (ESI, m/z): 235.1 [M+H$^+$].

17.vi. 6-methoxy-4-(3-{[(R)-2-oxo-3-(3-oxo-3,4-dihydro-2H-benzo[1,4]thiazin-6-yl)-oxazolidin-5-ylmethyl]-amino}-propyl)-4H-pyrido[2,3-b]pyrazin-3-one Starting from amine 17.v (169 mg) and intermediate E (294 mg) and following procedure M, the title compound was obtained as a light orange foam (57 mg; 16% yield).

$^1$H NMR (DMSO-d6) δ: 10.53 (s, 1H), 8.11 (m, 2H), 7.30 (m, 2H), 7.09 (dd, J=8.5, 2.3 Hz, 1H), 6.82 (d, J=8.5 Hz, 1H), 4.68 (s, 1H), 4.34 (t, J=7.0 Hz, 2H), 3.96 (s, 3H), 3.75 (dd, J=8.8, 6.4 Hz, 1H), 3.41 (s, 2H), 2.80 (m, 2H), 2.63 (m, 2H), 1.83 (m, 2H).
MS (ESI, m/z): 497.4 [M+H$^+$].

Example 18

4-(3-{[(R)-3-(2,3-dihydro-benzo[1,4]dioxin-6-yl)-2-oxo-oxazolidin-5-ylmethyl]-amino}-propyl)-6-methoxy-4H-pyrido[2,3-b]pyrazin-3-one Starting from amine 17.v (169 mg) and intermediate G (272 mg) and following procedure M, the title compound was obtained as a yellow foam (126 mg; 39% yield).
MS (ESI, m/z): 468.1 [M+H$^+$].

Example 19

6-methoxy-4-(3-{[(R)-2-oxo-3-(3-oxo-3,4-dihydro-2H-benzo[1,4]oxazin-6-yl)-oxazolidin-5-ylmethyl]-amino}-propyl)-4H-pyrido[2,3-b]pyrazin-3-one Starting from amine 17.v (157 mg) and intermediate C (239 mg) and following procedure M, the title compound was obtained as a yellow foam (30 mg; 9% yield)
$^1$H NMR (DMSO-d6) δ: 10.69 (s, 1H), 8.11 (m, 2H), 7.30 (d, J=0.6 Hz, 1H), 6.92 (s, 2H), 6.82 (m, 1H), 4.66 (m, 1H), 4.51 (s, 2H), 4.34 (m, 2H), 3.96 (s, 3H), 3.75 (m, 1H), 2.79 (m, 2H), 2.64 (m, 2H), 1.84 (m, 2H).
MS (ESI, m/z): 481.3 [M+H$^+$].

Example 20

6-methoxy-4-(2-{2-[(R)-2-oxo-3-(3-oxo-3,4-dihydro-2H-benzo[1,4]thiazin-6-yl)-oxazolidin-5-yl]-ethylamino}-ethyl)-4H-pyrido[2,3-b]pyrazin-3-one 20.i. [2-(6-methoxy-3-nitro-pyridin-2-ylamino)-ethyl]carbamic acid tert-butyl ester Starting from 2-chloro-6-methoxy-3-nitropyridine (5.0 g; commercial) and N-Boc-ethylenediamine (4.15 mL; commercial), and proceeding in analogy to Example 17, step 17.i, the title compound was obtained as a yellow solid (4.79 g; 59% yield).
MS (ESI, m/z): 313.3 [M+H$^+$].

20.ii. [2-(3-amino-6-methoxy-pyridin-2-ylamino)-ethyl]-carbamic acid tert-butyl ester Starting from intermediate 20.i (4.78 g) and proceeding in analogy to Example 17, step 17.ii, the title compound was obtained as a grey blue solid (4.21 g; 97% yield).
MS (ESI, m/z): 283.3 [M+H$^+$].

20.iii. [2-(2-tert-butoxycarbonylamino-ethylamino)-6-methoxy-pyridin-3-ylamino]-acetic acid ethyl ester Starting from intermediate 20.ii (4.17 g) and ethyl bromoacetate (1.64 mL) and proceeding in analogy to Example 17, step 17.iii, the title compound was obtained as a brown oil (3.85 g; 70% yield).
MS (ESI, m/z): 369.3 [M+H$^+$].

20.iv. [2-(6-methoxy-3-oxo-3H-pyrido[2,3-b]pyrazin-4-yl)-ethyl]carbamic acid tert-butyl ester Starting from intermediate 20.iii (3.83 g) and proceeding in analogy to Example 17, step 17.iv, the title compound was obtained as an orange solid (2.50 g; 75% yield).
MS (ESI, m/z): 321.3 [M+H$^+$].

20.v. 4-(2-amino-ethyl)-6-methoxy-4H-pyrido[2,3-b]pyrazin-3-one

Starting from intermediate 20.iv (2.49 g) and proceeding in analogy to Example 17, step 17.v, the title compound was obtained as an orange oil (760 mg; 44% yield).
MS (ESI, m/z): 221.1 [M+H$^+$].

20.vi. 6-methoxy-4-(2-{2-[(R)-2-oxo-3-(3-oxo-3,4-dihydro-2H-benzo[1,4]thiazin-6-yl)-oxazolidin-5-yl]-ethylamino}-ethyl)-4H-pyrido[2,3-b]pyrazin-3-one Starting from intermediate 20.v (275 mg) and intermediate H (465 mg) and following procedure M, the title compound was obtained as a brown solid (122 mg; 19% yield)
$^1$H NMR (DMSO-d6) δ: 10.54 (s, 1H), 8.11 (m, 2H), 7.31 (m, 2H), 7.03 (dd, J=8.8, 2.3 Hz, 1H), 6.82 (d, J=8.8 Hz, 1H), 4.69 (m, 1H), 4.39 (m, 2H), 3.98 (m, 3H), 3.65 (m, 1H), 3.41 (m, 2H), 2.88 (m, 2H), 2.70 (m, 2H), 1.82 (m, 2H).
MS (ESI, m/z): 497.4 [M+H$^+$].

Example 21

6-methoxy-4-(2-{2-[(R)-2-oxo-3-(3-oxo-3,4-dihydro-2H-benzo[1,4]oxazin-6-yl)-oxazolidin-5-yl]-ethylamino}-ethyl)-4H-pyrido[2,3-b]pyrazin-3-one Starting from intermediate 20.v (275 mg) and intermediate H (534 mg) and following procedure M, the title compound was obtained as a brown foam (24 mg; 4% yield)
MS (ESI, Ink): 481.4 [M+H$^+$].

Example 22

6-methoxy-4-(1-{2-[(R)-2-oxo-3-(3-oxo-3,4-dihydro-2H-benzo[1,4]thiazin-6-yl)-oxazolidin-5-yl]-ethyl}-azetidin-3-yl)-4H-pyrido[2,3-b]pyrazin-3-one 22.i. 4-azetidin-3-yl-6-methoxy-4H-pyrido[2,3-b]pyrazin-3-one Starting from 2-chloro-6-methoxy-3-nitropyridine (7.7 g; commercial) and 3-amino-1-Boc-azetidine (6.9 g, commercial) and following the procedures of Example 17, steps 17.i to 17.v, the title compound was obtained as a yellow solid (1 g; 10% yield over 5 steps).
MS (ESI, m/z): 233.1 [M+H$^+$].

22.ii. 6-methoxy-4-(1-{2-[(R)-2-oxo-3-(3-oxo-3,4-dihydro-2H-benzo[1,4]thiazin-6-yl)-oxazolidin-5-yl]-ethyl}-azetidin-3-yl)-4H-pyrido[2,3-b]pyrazin-3-one Starting from intermediate 22.i (100 mg) and intermediate J (175 mg) and following procedure M, the title compound was obtained as a beige solid (70 mg; 31% yield)
MS (ESI, m/z): 509.2 [M+H$^+$].

Example 23

6-methoxy-4-(1-{3-[(R)-2-oxo-3-(3-oxo-3,4-dihydro-2H-benzo[1,4]thiazin-6-yl)-oxazolidin-5-yl]-propyl}-azetidin-3-yl)-4H-pyrido[2,3-b]pyrazin-3-one Starting from intermediate 22.i (100 mg) and intermediate K (167 mg) and following procedure M, the title compound was obtained as a beige solid (16 mg; 7% yield)
MS (ESI, m/z): 523.2 [M+H$^+$].

Example 24

6-methoxy-4-(1-{2-[(S)-2-oxo-3-(3-oxo-3,4-dihydro-2H-benzo[1,4]thiazin-6-yl)-oxazolidin-5-yl]-ethyl}-azetidin-3-yl)-4H-pyrido[2,3-b]pyrazin-3-one Starting from intermediate 22.i (100 mg) and intermediate L (161 mg) and following procedure M, the title compound was obtained as a beige solid (27 mg; 12% yield)
MS (ESI, m/z): 509.2 [M+H$^+$].

Example 25

4-((R)-2-hydroxy-3-{[(R)-2-oxo-3-(3-oxo-3,4-dihydro-2H-benzo[1,4]thiazin-6-yl)-oxazolidin-5-ylmethyl]-amino}-propyl)-6-methoxy-4H-pyrido[2,3-b]pyrazin-3-one

25.i. [(S)-2-hydroxy-3-(6-methoxy-3-nitro-pyridin-2-ylamino)-propyl]-carbamic acid tert-butyl ester Starting from 2-chloro-6-methoxy-3-nitropyridine (5.4 g; commercial) and ((S)-3-amino-2-hydroxy-propyl)-carbamic acid tert-butyl ester (5.3 g, 1 eq.; prepared according to *Adv. Synth. Catal.* 2004, 346, 1195) and proceeding in analogy to Example 17, step 17.i, the title compound was obtained as a yellow solid (8.20 g; 86% yield).
MS (ESI, m/z): 343.2 [M+H$^+$].

25.ii. [(S)-3-(3-amino-6-methoxy-pyridin-2-ylamino)-2-(tert-butyl-dimethyl-silanyloxy)-propyl] carbamic acid tert-butyl ester A solution of intermediate 25.i (8.0 g) in EtOH (200 mL) was hydrogenated over 10% Pd/C (2.5 g). After 3 h the catalyst was filtered off and the filtrate was evaporated under reduced pressure. To a solution of the resulting oil (6.8 g) and imidazole (2.96 g) in THF (55 mL) a solution of TBDMSCl (6.56 g, 2 eq.) in THF (50 mL) was added dropwise at rt. The resulting mixture was stirred at rt overnight. The solids were filtered off and the filtrate was washed with water and brine, dried over MgSO$_4$ and concentrated under reduced pressure to afford the title intermediate as a dark blue oil (10.0 g, quant.) which was used immediately in the next step.
MS (ESI, m/z): 427.1 [M+H$^+$].

25.iii. {2-[(S)-3-tert-butoxycarbonylamino-2-(tert-butyl-dimethyl-silanyloxy)-propylamino]-6-methoxy-pyridin-3-ylamino}-acetic acid ethyl ester A solution of intermediate 25.ii (9.26 g) and ethyl bromoacetate (2.40 mL) in MeCN (110 mL) and DMF (50 mL) was stirred overnight at rt in presence of K$_2$CO$_3$ (6.00 g). The reaction mixture was filtered and the filtrate was evaporated under reduced pressure. The residue was taken up in EA (200 mL), sequentially washed with water and brine, dried over MgSO$_4$ and purified by CC (Hept/EA, 2:1 to 1:1) affording 9.60 g (86% yield) of a dark blue oil.
$^1$H NMR (CDCl$_3$) δ: 6.92 (m, 1H), 5.91 (d, J=8.2 Hz, 1H), 4.21 (q, J=7.0 Hz, 2H), 3.99 (m, 1H), 3.84 (s, 3H), 3.72 (s, 2H), 3.40-3.05 (m, 4H), 1.43 (s, 9H), 1.28 (m, 5H), 0.91 (s, 9H), 0.10 (s, 6H).

25.iv [(R)-2-(tert-butyl-dimethyl-silanyloxy)-3-(6-methoxy-3-oxo-3H-pyrido[2,3-b]pyrazin-4-yl)-propyl]-carbamic acid tert-butyl ester A solution of intermediate 25.iii (9.60 g) in toluene (360 mL) containing AcOH (2.1 mL) was refluxed overnight. The resulting solution was concentrated and diluted with DCM (200 mL), treated with MnO$_2$ (20 g) and further stirred at rt for 5 h. The suspension was filtered and the filtrate was evaporated under reduced pressure and purified by CC (Hept/EA 1:1), affording a yellowish oil (5.30 g; 47% yield).
MS (ESI, m/z): 465.2 [M+H$^+$].

25.v. 4-[(R)-3-amino-2-(tert-butyl-dimethyl-silanyloxy)-propyl]-6-methoxy-4H-pyrido[2,3-b]pyrazin-3-one Intermediate 25.iv (1.0 g) was deprotected according to Procedure E to give the desired amine as a brown oil (quant.).
MS (ESI, m/z): 365.0 [M+H$^+$].

25.vi. 4-((R)-2-(tert-butyl-dimethyl-silanyloxy)-3-{[(R)-2-oxo-3-(3-oxo-3,4-dihydro-2H-benzo[1,4]thiazin-6-yl)-oxazolidin-5-ylmethyl]-amino}-propyl)-6-methoxy-4H-pyrido[2,3-b]pyrazin-3-one Starting from intermediate 25.v (270 mg) and intermediate E (289 mg) and following procedure M, the title compound was obtained as a beige foam (57 mg; 16% yield).
MS (ESI, m/z): 627.1 [M+H$^+$].

25.vii. 4-((R)-2-hydroxy-3-{[(R)-2-oxo-3-(3-oxo-3,4-dihydro-2H-benzo[1,4]thiazin-6-yl)-oxazolidin-5-ylmethyl]-amino}-propyl)-6-methoxy-4H-pyrido[2,3-b]pyrazin-3-one Starting with intermediate 25.vi (180 mg) and using procedure F, the title compound was obtained as a yellow solid (70 mg, 48% yield).
MS (ESI, m/z): 513.3 [M+H$^+$].

Example 26

4-((R)-3-{[(R)-3-(2,3-dihydro-benzo[1,4]dioxin-6-yl)-2-oxo-oxazolidin-5-ylmethyl]-amino}-2-hydroxy-propyl)-6-methoxy-4H-pyrido[2,3-b]pyrazin-3-one

26.i. 4-((R)-2-(tert-butyl-dimethyl-silanyloxy)-3-{[(R)-3-(2,3-dihydro-benzo[1,4]dioxin-6-yl)-2-oxo-oxazolidin-5-ylmethyl]-amino}-propyl)-6-methoxy-4H-pyrido[2,3-b]pyrazin-3-one Starting from intermediate 25.i (270 mg) and intermediate G (267 mg) and following procedure M, the title compound was obtained as a beige foam (220 mg; 50% yield).
MS (ESI, m/z): 598.2 [M+H$^+$].

26.ii. 4-((R)-3-([(R)-3-(2,3-dihydro-benzo[1,4]dioxin-6-yl)-2-oxo-oxazolidin-5-ylmethyl]-amino)-2-hydroxy-propyl)-6-methoxy-4H-pyrido[2,3-b]pyrazin-3-one Starting with intermediate 26.i (200 mg) and using procedure F, the title compound was obtained as a yellow solid (60 mg, 37% yield).
MS (ESI, m/z): 484.1 [M+H$^+$].

Example 27

4-((R)-2-hydroxy-3-{[(R)-2-oxo-3-(3-oxo-3,4-dihydro-2H-benzo[1,4]oxazin-6-yl-oxazolidin-5-ylmethyl]-amino}-propyl)-6-methoxy-4H-pyrido[2,3-b]pyrazin-3-one 27.i. 4-((R)-2-(tert-butyl-dimethyl-silanyloxy)-3-{[(R)-2-oxo-3-(3-oxo-3,4-dihydro-2H-benzo[1,4]oxazin-6-yl)-oxazolidin-5-ylmethyl]-amino}-propyl)-6-methoxy-4H-pyrido[2,3-b]pyrazin-3-one Starting from intermediate 25.i (240 mg) and intermediate C (225 mg) and following procedure M, the title compound was obtained as a yellow resin (130 mg; 32% yield).
MS (ESI, m/z): 611.2 [M+H$^+$].

27.ii. 4-((R)-2-hydroxy-3-{[(R)-2-oxo-3-(3-oxo-3,4-dihydro-2H-benzo[1,4]oxazin-6-yl)-oxazolidin-5-ylmethyl]-amino}-propyl)-6-methoxy-4H-pyrido[2,3-b]pyrazin-3-one Starting with intermediate 27.i (110 mg) and using procedure F, the title compound was obtained as a yellow solid (60 mg, 74% yield).
MS (ESI, m/z): 497.3 [M+H$^+$].

Example 28

1-(3-{[(R)-3-(2,3-dihydro-benzo[1,4]dioxin-6-yl)-2-oxo-oxazolidin-5-ylmethyl]-amino}-propyl)-7-methoxy-3,4-dihydro-1H-quinolin-2-one A solution of the compound of Example 3 in MeOH/AcOH (1:1, 3 mL) was hydrogenated over Pd/C (59 mg) at 40° C. for 4 h. After cooling to rt the catalyst was filtered off and the filter cake was washed with MeOH and MeOH/DCM. The combined filtrates were concentrated. Water and NH$_4$OH were added and the mixture was extracted with DCM/MeOH 9:1. The combined org. layers were dried over MgSO$_4$ and concentrated under reduced pressure to afford the title compound as a colourless resin (22 mg, 84% yield).
MS (ESI, m/z): 468.0 [M+H$^+$].

Example 29

4-(3-{[(R)-3-(3-fluoro-4-methyl-phenyl)-2-oxo-oxazolidin-5-ylmethyl]-amino}-propyl)-6-methoxy-4H-pyrido[2,3-b]pyrazin-3-one Starting with (5S)-3-(3-fluoro-4-methylphenyl)-5-(iodomethyl)-2-oxazolidinone (107 mg; prepared according to WO 2008/126034) and intermediate 17.v (75 mg) and using procedure M, the title compound was obtained as a pale yellow resin (35 mg; 25% yield).
$^1$H NMR (CDCl$_3$) δ: 8.12 (s, 1H), 7.99 (d, J=8.8 Hz, 1H), 7.35 (m, 1H), 7.12 (m, 2H), 6.71 (m, 1H), 4.72 (m, 1H), 4.49 (t, J=7.0 Hz, 2H), 3.99 (m, 4H), 3.85 (dd, J=8.5, 7.0 Hz, 1H), 2.93 (m, 2H), 2.75 (td, J=6.7, 3.2 Hz, 2H), 2.21 (d, J=1.8 Hz, 3H), 1.99 (m, 2H), 1.73 (s, 1H).
MS (ESI, m/z): 442.1 [M+H$^+$].

Example 30

6-methoxy-4-{1-[(R)-2-oxo-3-(3-oxo-3,4-dihydro-2H-benzo[1,4]thiazin-6-yl)-oxazolidin-5-ylmethyl]-azetidin-3-yl}-4H-pyrido[2,3-b]pyrazin-3-one Starting with 6-[(5S)-5-(iodomethyl)-2-oxo-3-oxazolidinyl]-2H-1,4-benzothiazin-3(4H)-one (337 mg; prepared according to WO 2008/126034) and intermediate 22.i (200 mg) and using procedure M, the title compound was obtained as a light yellow foam (130 mg; 30% yield).
$^1$H NMR (DMSO-d6) δ: 10.55 (s, 1H), 8.10 (d, J=8.5 Hz, 1H), 8.02 (s, 1H), 7.31 (m, 2H), 7.12 (dd, J=8.5, 2.3 Hz, 1H), 6.81 (d, J=8.5 Hz, 1H), 4.73 (m, 2H), 4.08 (m, 3H), 3.90 (s, 3H), 3.42 (s, 2H), 3.35 (m, 2H), 2.74 (m, 2H).
MS (ESI, m/z): 459.1 [M+H$^+$].

Example 31 rac-4-(2-{2-[3-(2,3-dihydro-[1,4]dioxino[2,3-c]pyridin-7-yl)-2-oxo-oxazolidin-5-yl]-ethylamino}-ethyl)-6-methoxy-4H-pyrido[2,3-b]pyrazin-3-one Starting from intermediate M (100 mg) and intermediate 20.v (63.8 mg) and using procedure D, the title compound was obtained after CC (DCM/MeOH 19:1 to 9:1) as a beige foam (42 g; 31% yield).
$^1$H NMR (DMSO-d6) δ: 8.10 (m, 2H), 7.89 (s, 1H), 7.50 (s, 1H), 6.81 (d, J=8.8 Hz, 1H), 4.67 (m, 1H), 4.37 (m, 6H), 4.25 (m, 2H), 4.14 (m, 1H), 3.98 (s, 3H), 3.71 (m, 1H), 2.88 (m, 2H), 2.70 (m, 2H), 1.80 (m, 2H).
MS (ESI, m/z): 468.9 [M+H$^+$].

Example 32 rac-4-(2-{2-[3-(2,3-dihydro-[1,4]dioxino[2,3-b]pyridin-6-yl)-2-oxo-oxazolidin-5-yl]-ethylamino}-ethyl)-6-methoxy-4H-pyrido[2,3-b]pyrazin-3-one Starting from Intermediate N (100 mg) and intermediate 20.v (63.9 mg) and using procedure M, the title compound was obtained as a beige solid (44 mg; 32% yield).
$^1$H NMR (DMSO-d6) δ: 8.66 (d, J=4.7 Hz, 1H), 8.22 (d, J=9.1 Hz, 1H), 7.54 (m, 2H), 7.34 (d, J=8.5 Hz, 1H), 7.23 (d, J=9.1 Hz, 1H), 4.71 (m, 1H), 4.37 (m, 2H), 4.16 (m, 3H), 4.02 (s, 3H), 3.71 (m, 1H), 3.02 (m, 2H), 2.78 (m, 2H), 1.88 (m, 2H).
MS (ESI, m/z): 452.0 [M+H$^+$].

Example 33 rac-6-(5-{2-[2-(6-methoxy-3-oxo-3H-pyrido[2,3-b]pyrazin-4-yl)-ethylamino]-ethyl}-2-oxo-oxazolidin-3-yl)-4H-pyrido[3,2-b][1,4]oxazin-3-one 33.i. 6-bromo-4-(4-methoxy-benzyl)-4H-pyrido[3,2-b][1,4]oxazin-3-one A suspension of 6-bromo-2H-pyrido[3,2-b]-1,4-oxazin-3(4H)-one (2.0 g; prepared according to WO 01/30782) in DMF (40 mL) was treated with 4-methoxybenzyl chloride (1.18 mL) and Cs$_2$CO$_3$ (8.5 g) and stirred at rt for 2 h. The solvent was evaporated under reduced pressure and the residue was partitioned between EA and water. The org. layer was washed with brine, dried over MgSO$_4$ and evaporated under reduced pressure. The residue was triturated with Hept, affording a beige solid (2.8 g, 92% yield).

$^1$H NMR (CDCl$_3$) δ: 7.49 (d, J=8.8 Hz, 2H), 7.05 (s, 2H), 6.83 (d, J=8.8 Hz, 2H), 6.83 (d, J=8.8 Hz, 2H), 6.83 (d, J=8.8 Hz, 2H), 4.67 (s, 2H), 3.77 (s, 3H).

33.ii. rac-1-azido-4-(tert-butyl-dimethyl-silanyloxy)-butan-2-ol

A solution of 2-[2-[[(tert-butyl)dimethylsilyl]oxy]ethyl]-oxirane (5.0 g; prepared according to WO 2007/144423) in MeOH (150 mL) was reacted with NaN$_3$ (3.95 g) and NH$_4$Cl (2.37 g). The reaction mixture was further stirred at 80° C. overnight. The solvent was evaporated under reduced pressure and the residue was partitioned between EA and water. The org layer was washed with brine, dried over Na$_2$SO$_4$ and evaporated under reduced pressure, affording a yellow oil (4.9 g, 81% yield).

$^1$H NMR (CDCl$_3$) δ: 4.01 (m, 1H), 3.87 (m, 2H), 3.30 (m, 2H), 1.72 (m, 2H), 0.90 (m, 9H), (m, 6H).

33.iii. rac-1-amino-4-(tert-butyl-dimethyl-silanyloxy)-butan-2-ol

A solution of intermediate 33.ii (4.85 g) in THF (100 mL) was hydrogenated for 3 h over 10% Pd/C (1.0 g). The catalyst was filtered off and the filtrate was evaporated under reduced pressure, affording a yellow oil (4.1 g, 94.5% yield).

MS (ESI, m/z): 219.8 [M+H$^+$].

33.iv. rac-5-[2-(tert-butyl-dimethyl-silanyloxy)-ethyl]oxazolidin-2-one

Starting from intermediate 33.iii (4.0 g) and using procedure B, the title compound was obtained as a light yellow oil (3.3 g; 73.8% yield).

$^1$H NMR (CDCl$_3$) δ: 5.22 (br., 1H), 4.80 (m, 1H), 3.74 (m, 3H), 3.33 (m, 1H), 1.93 (m, 2H), 0.89 (m, 9H), 0.07 (m, 6H).

33.v. rac-6-{5-[2-(tert-butyl-dimethyl-silanyloxy)-ethyl]-2-oxo-oxazolidin-3-yl}-4-(4-methoxy-benzyl)-4H-pyrido[3,2-b][1,4]oxazin-3-one Intermediates 33.iv (1.97 g) and 33.i (2.8 g), CuI (305 mg) and K$_2$CO$_3$ (2.2 g) were placed in a round bottom flask and the flask was flushed with argon. Trans-1,2-diaminocyclohexane (1.2 mL) and dioxane (60 mL) were added to the mixture and the reaction flask was again flushed with argon. The reaction mixture was stirred at 100° C. for 2 days and partitioned between EA and water. The org. layer was washed with brine, dried over MgSO$_4$ and evaporated under reduced pressure. The residue was purified by CC (DCM/MeOH 19:1), affording, after crystallisation from Hept, a colourless solid (1.7 g, 41% yield).

$^1$H NMR (CDCl$_3$) δ: 7.81 (d, J=8.8 Hz, 1H), 7.28 (m, 3H), 6.81 (m, 2H), 5.20 (s, 2H), 4.82 (m, 1H), 4.28 (m, 1H), 3.85 (m, 3H), 3.77 (s, 3H), 2.00 (m, 2H), 0.89 (s, 9H), 0.07 (s, 6H).

33.vi. rac-6-[5-(2-hydroxy-ethyl)-2-oxo-oxazolidin-3-yl]-4-(4-methoxy-benzyl)-4H-pyrido[3,2-b][1,4]oxazin-3-one Starting from intermediate 33.v (1.7 g) and using procedure F, the title compound was obtained after purification by CC (EA then EA/MeOH 9:1) as a yellow oil (1.4 g; 100% yield).

MS (ESI, m/z): 400.0 [M+H$^+$].

33.vii. rac-methanesulfonic acid 2-{3-[4-(4-methoxy-benzyl)-3-oxo-3,4-dihydro-2H-pyrido[3,2-b]1,4]oxazin-6-yl}-2-oxo-oxazolidin-5-yl)-ethyl ester Starting from intermediate 33.vi (1.32 g) and using procedure D, the title compound was obtained as a colourless foam (1.3 g; 82.5% yield)

MS (ESI, m/z): 477.8 [M+H$^+$].

33.viii. rac-4-(4-methoxy-benzyl)-6-(5-{2[2-(6-methoxy-3-oxo-3H-pyrido[2,3-b]pyrazin-4-yl)-ethylamino]ethyl}-2-oxo-oxazolidin-3-yl)-4H-pyrido[3,2-b][1,4]oxazin-3-one Starting from intermediates 33.vii (433 mg) and 20.v (200 mg) and following procedure M, the title compound was obtained after purification by CC (DCM/MeOH 19:1) as an orange oil (200 mg, 36% yield).

MS (ESI, m/z): 602.1 [M+H$^+$].

33.ix. rac-6-(5-{2-[2-(6-methoxy-3-oxo-3H-pyrido[2,3-b]pyrazin-4-yl)-ethylamino]-ethyl}-2-oxo-oxazolidin-3-yl)-4H-pyrido[3,2-b][1,4]oxazin-3-one A solution of intermediate 33.viii (200 mg) in TFA (5 mL) was heated at 70° C. for 5 days. The solvent was evaporated under reduced pressure and the residue was partitioned between DCM and 33% aq. NH$_4$OH. The org. phase was washed with water, dried over MgSO$_4$ and evaporated under reduced pressure. The residue was purified by CC (DCM/MeOH 19:1) and crystallized from ether/EA, affording a rusty solid (62 mg, 39% yield).

MS (ESI, m/z): 482.1 [M+H$^+$].

Example 34

4-(1-{2-[(R)-3-(4-ethoxy-phenyl)-2-oxo-oxazolidin-5-yl]-ethyl}-azetidin-3-yl)-6-methoxy-4H-pyrido[2,3-b]pyrazin-3-one Starting from intermediate 22.i (74.5 mg) and intermediate 0 (105.6 mg) and using procedure M, the title compound was obtained after purification by CC (DCM/MeOH/NH$_4$OH 1000:50:4 to 1000:100:8) as a yellow foam (20 mg; 14% yield).

MS (ESI, m/z): 466.1 [M+H$^+$].

Example 35

6-methoxy-2-methyl-4-(3-{[(R)-2-oxo-3-(3-oxo-3,4-dihydro-2H-benzo[1,4]thiazin-6-yl)-oxazolidin-5-ylmethyl]-amino}-propyl)-4H-pyrido[2,3-b]pyrazin-3-one

35.i. [3-(tert-butyl-dimethyl-silanyloxy)-propyl]-(6-methoxy-3-nitro-pyridin-2-yl)-amine A solution of 2-chloro-6-methoxy-3-nitropyridine (commercial; 5.77 g) and aminopropanol (2.25 g) in MeCN/DMF (10:3, 130 mL) was heated at 50° C. for 1 h in presence of K$_2$CO$_3$ (4.16 g). The reaction mixture was filtered and the filtrate was evaporated under reduced pressure. The residue was partitioned between water and ether. The org. phase was sequentially washed with water and brine, dried over MgSO$_4$ and evaporated to dryness. The crude 3-(6-methoxy-3-nitropyridin-2-ylamino)-propan-1-ol was dissolved in THF (5 mL) and added dropwise to a solution of TBDMSCl (9.5 g) and imidazole (4.5 g) in THF (100 mL). The mixture was stirred for 1 h at rt and partitioned between water and ether. The org. phase was sequentially washed with water and brine, dried over MgSO$_4$, concentrated under reduced pressure and purified by CC (EA/Hept 1:9 to 1:4), affording a yellow solid (9.45 g, 92% yield).

$^1$H NMR (CDCl$_3$) δ: 8.76 (m, 1H), 8.30 (d, J=9.1 Hz, 1H), 6.03 (d, J=9.1 Hz, 1H), 3.96 (s, 3H), 3.74 (m, 4H), 1.89 (m, 2H), 0.90 (m, 9H), 0.07 (m, 6H),

35.ii. N$^2$-[3-(tert-butyl-dimethyl-silanyloxy)-propyl]-6-methoxy-pyridine-2,3-diamine A solution of intermediate 35.i in MeOH/THF (300 mL; 1:1) was hydrogenated over 10% Pd/C (733 mg) for 3 h. The catalyst was filtered off and the filtrate was evaporated under reduced pressure, affording a violet air-sensitive oil (8.37 g, 97% yield).

$^1$H NMR (CDCl$_3$) δ: 6.86 (d, J=7.9 Hz, 1H), 5.88 (d, J=7.9 Hz, 1H), 4.75 (m, 1H), 3.83 (s, 3H), 3.77 (t, J=6.2 Hz, 2H), 2.80 (m, 2H), 1.87 (m, 2H), 0.91 (m, 9H), 0.07 (m, 6H).

35.iii. 4-[3-(tert-butyl-dimethyl-silanyloxy)-propyl]-6-methoxy-1,4-dihydro-pyrido[2,3-b]pyrazine-2,3-dione A solution of intermediate 35.ii (0.5 g), ethylpyruvate (0.37 mL) EtOH (12 mL) was stirred at 50° C. overnight. The mixture was concentrated under reduced pressure and purified by CC (Hept/EA 9:1 to 2:1), affording the title compound as a dark grey solid (222 mg, 38% yield).

MS (ESI, m/z): 364.1 [M+H$^+$].

35.iv 4-(3-hydroxy-propyl)-6-methoxy-2-methyl-4H-pyrido[2,3-b]pyrazin-3-one

Starting from intermediate 35.iii (218 mg) and using procedure F, the title compound was obtained, after purification by CC (EA), as a black solid (152 mg; 100% yield).

MS (ESI, m/z): 250.1 [M+H$^+$].

35.v. 3-(6-methoxy-2-methyl-3-oxo-3H-pyrido[2,3-b]pyrazin-4-yl)-propionaldehyde A solution of intermediate 35.iv (149 mg) and DIPEA (0.6 mL) in DCM (4 mL) was cooled to 0° C. and treated with a solution of Pyr.SO$_3$ complex (7.6 g) in DMSO (29 mL). The reaction was further stirred at this temperature for 2.5 h and quenched with water (200 mL). The org layer was separated and the aq. layer was extracted with DCM. The combined org. layers were sequentially washed with water, brine, dried over MgSO$_4$, filtered and concentrated under reduced pressure. The compound was used as such in the following step.

MS (ESI, m/z): 248.3 [M+H$^+$].

35.vi. 6-methoxy-2-methyl-4-(3-{[(R)-2-oxo-3-(3-oxo-3,4-dihydro-2H-benzo[1,4]thiazin-6-yl)-oxazolidin-5-ylmethyl]-amino}-propyl)-4H-pyrido[2,3-b]pyrazin-3-one Starting from intermediate 35.v (74 mg) and intermediate B (83.8 mg) and using procedure I, the title compound was obtained, after CC (EA, then DCM/MeOH 19:1 to 9:1), as a beige foam (34 mg; 22% yield).

$^1$H NMR (DMSO d6) δ: 10.53 (m, 1H), 8.03 (d, J=8.5 Hz, 1H), 7.29 (m, 2H), 7.09 (m, 1H), 6.78 (d, J=8.8 Hz, 1H), 4.68 (m, 1H), 4.35 (m, 2H), 3.99 (m, 4H), 3.76 (m, 1H), 3.41 (s, 2H), 2.80 (m, 2H), 2.64 (m, 2H), 1.83 (m, 2H).

MS (ESI, m/z): 511.0 [M+H$^+$].

Pharmacological Properties of the Invention Compounds

Experimental Procedures:

Minimal inhibitory concentrations (MICS; mg/l) were determined in cation-adjusted Mueller-Hinton Broth by a microdilution procedure following the description given in "Procedures for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006.

Results:

All Example compounds were tested against several Gram positive and Gram negative bacteria such as *S. aureus, E. faecalis, S. pneumoniae, M. catarrhalis, A. baumanii, E. coli* or *P. aeruginosa*. Antibacterial test results against *Moraxella catarrhalis* A894 are given in the table hereafter (MIC in mg/l).

| Compound of Example | *Moraxella catarrhalis* A894 |
|---|---|
| 1 | <=0.031 |
| 2 | <=0.031 |
| 3 | <=0.031 |
| 4 | <=0.031 |
| 5 | 0.25 |
| 6 | <=0.031 |
| 7 | 0.5 |
| 8 | 0.25 |
| 9 | <=0.031 |
| 10 | 0.125 |
| 11 | <=0.031 |
| 12 | 1 |
| 13 | <=0.031 |
| 14 | <=0.031 |
| 15 | <=0.031 |
| 16 | <=0.031 |
| 17 | <=0.031 |
| 18 | <=0.031 |
| 19 | <=0.031 |
| 20 | <=0.031 |
| 21 | <=0.031 |
| 22 | <=0.031 |
| 23 | <=0.031 |
| 24 | <=0.031 |
| 25 | <=0.031 |
| 26 | 0.25 |
| 27 | <=0.031 |
| 28 | 1 |
| 29 | 0.063 |
| 30 | <=0.016 |
| 31 | 1 |
| 32 | 1 |
| 33 | <=0.031 |
| 34 | 8 |
| 35 | <=0.016 |

The invention claimed is:

1. A compound of Formula (I)

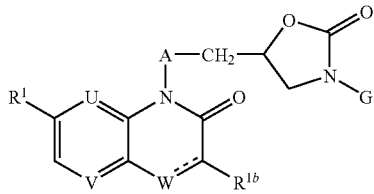

Formula (I)

wherein

"----" is a bond or is absent;

$R^1$ represents $(C_1-C_4)$alkoxy or halogen;

$R^{1b}$ represents H or $(C_1-C_3)$alkyl;

U and V each independently represent CH or N;

W represents CH or N, or, in case "----" is absent, W represents $CH_2$ or NH;

with the proviso that at least one of U, V and W represents CH or $CH_2$;

A represents —$CH_2$—$CH(R^2)$-B-NH—* or —$CH(R^3)$—$CH_2$—$N(R^4)$—$[CH_2]_m$—*; wherein the asterisks indicate the bond which is linked via the $CH_2$-group to the oxazolidinone moiety;

B represents $CH_2$ or CO; and $R^2$ represents hydrogen, OH or $NH_2$;

$R^3$ and $R^4$ both represent hydrogen, or $R^3$ and $R^4$ together form a methylene bridge;

m represents the integer 0, 1 or 2; and

G represents phenyl which is mono-substituted in position 3 or 4, or disubstituted in positions 3 and 4, wherein each substituent is independently $(C_1-C_4)$alkyl, $(C_1-C_3)$alkoxy or halogen; or G represents $G^1$, $G^2$, $G^3$, $G^4$, $G^5$ or $G^6$ drawn below:

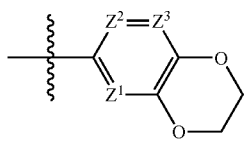
$G^1$

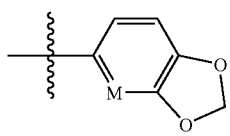
$G^2$

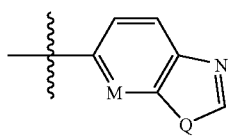
$G^3$

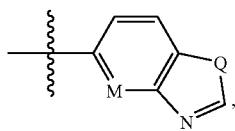
$G^4$

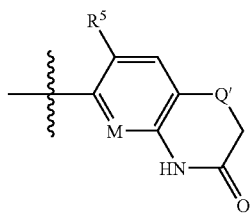
$G^5$

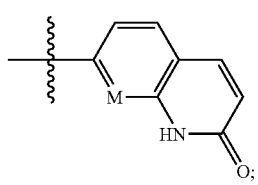
$G^6$ wherein

M represents CH or N;

Q and Q' independently represent S or O;

$Z^1$ represents N, $Z^2$ represents CH, and $Z^3$ represents CH; or $Z^1$ represents CH, $Z^2$ represents N, and $Z^3$ represents CH or N; or $Z^1$ represents CH, $Z^2$ represents $CR^5$, and $Z^3$ represents CH; or $Z^1$ represents CH, $Z^2$ represents CH, and $Z^3$ represents N; and $R^5$ represents hydrogen or fluorine;

or a salt of such a compound.

2. A compound of Formula (I) according to claim 1, wherein $R^{1b}$ represents H and m, if present, represents 1 or 2;

or a salt of such a compound.

3. The compound according to claim 1 of formula $(I_{P1})$

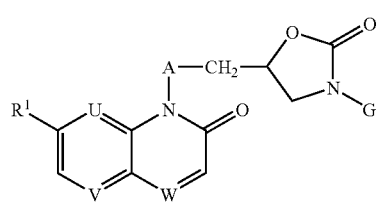

Formula $(I_{P1})$ wherein $R^1$ represents $(C_1-C_4)$alkoxy or halogen;

U represents CH or N;

V represents CH;

W represents CH or N;

A represents —$CH_2$—$CH(R^2)$-B-NH—* or —$CH(R^3)$—$CH_2$—$N(R^4)$—$CH_2$—*; wherein the asterisks indicate the bond which is linked via the $CH_2$-group to the oxazolidinone moiety;

$R^2$ represents hydrogen, OH or $NH_2$;

$R^3$ and $R^4$ together represent $CH_2$;

B represents $CH_2$ or CO; and

G represents 6,7-dihydro-[1,4]dioxino[2,3-d]pyridazin-3-yl; or

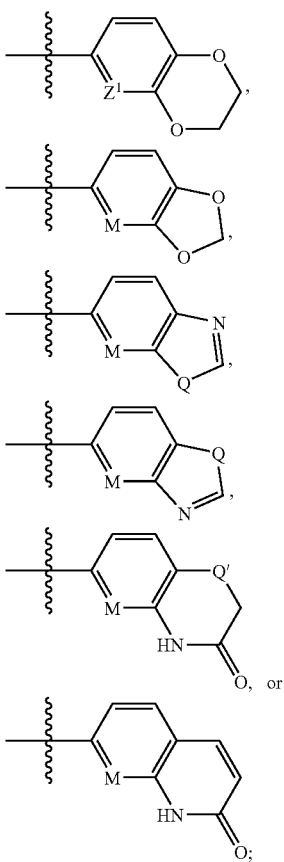

wherein

M and $Z^1$ represent CH or N; and

Q and Q' independently represent S or O;

or a salt of such a compound.

4. A compound of Formula (I) according to claim 1, wherein the stereocenter at position 5 of the oxazolidin-2-one ring is in (R)-configuration or a salt of such a compound.

5. A compound of Formula (I) according to claim 1, wherein U, V and W each represent CH, or U and V each represent CH and W represents N, or U and W each represent N and V represents CH;

or a salt of such a compound.

6. A compound of Formula (I) according to claim 1, wherein $R^1$ represents $(C_1-C_4)$alkoxy;

or a salt of such a compound.

7. A compound of Formula (I) according to claim 1, wherein A represents —$CH_2$—$CH(R^2)$-B-NH—*;

or a salt of such a compound.

8. A compound of Formula (I) according to claim 7, wherein B represents $CH_2$ and $R^2$ represents hydrogen or OH;

or a salt of such a compound.

9. A compound of Formula (I) according to claim 1, wherein A represents —$CH(R^3)$—$CH_2$—$N(R^4)$—$[CH_2]_m$—* wherein $R^3$ and $R^4$ together form a methylene bridge and m represents the integer 1 or 2;

or a salt of such a compound.

10. A compound of Formula (I) according to claim 1, wherein G represents a group selected from 3-fluoro-4-methyl-phenyl, 4-ethoxy-phenyl, 2,3-dihydro-benzo[1,4]dioxin-6-yl, 2,3-dihydro-[1,4]dioxino[2,3-c]pyridin-7-yl, 2,3-dihydro-[1,4]dioxino[2,3-b]pyridin-6-yl, 3-oxo-3,4-dihydro-2H-benzo[1,4]oxazin-6-yl, 3-oxo-3,4-dihydro-2H-pyrido[3,2-b][1,4]oxazine-6-yl, 3-oxo-3,4-dihydro-2H-benzo[1,4]thiazin-6-yl and 7-fluoro-3-oxo-3,4-dihydro-2H-benzo[1,4]thiazin-6-yl;

or a salt of such a compound.

11. A compound of Formula (I) according to claim 1 selected from the following compounds:

6-((R)-5-{[3-(7-methoxy-2-oxo-2H-quinolin-1-yl)-propylamino]-methyl}-2-oxo-oxazolidin-3-yl)-4H-benzo[1,4]thiazin-3-one;

6-((R)-5-{[3-(7-bromo-2-oxo-2H-quinolin-1-yl)-propylamino]-methyl}-2-oxo-oxazolidin-3-yl)-4H-benzo[1,4]thiazin-3-one;

1-(3-{[(R)-3-(2,3-dihydro-benzo[1,4]dioxin-6-yl)-2-oxo-oxazolidin-5-ylmethyl]-amino}-propyl)-7-methoxy-1H-quinolin-2-one;

7-bromo-1-(3-{[(R)-3-(2,3-dihydro-benzo[1,4]dioxin-6-yl)-2-oxo-oxazolidin-5-ylmethyl]-amino}-propyl)-1H-quinolin-2-one;

6-(5-{2-[3-(7-methoxy-2-oxo-2H-quinolin-1-yl)-azetidin-1-yl]-ethyl}-2-oxo-oxazolidin-3-yl)-4H-benzo[1,4]thiazin-3-one;

3-(7-methoxy-2-oxo-2H-quinoxalin-1-yl)-N-[(R)-2-oxo-3-(3-oxo-3,4-dihydro-2H-benzo[1,4]thiazin-6-yl)-oxazolidin-5-ylmethyl]-propionamide;

N-[(R)-3-(2,3-dihydro-benzo[1,4]dioxin-6-yl)-2-oxo-oxazolidin-5-ylmethyl]-3-(7-methoxy-2-oxo-2H-quinolin-1-yl)-propionamide;

3-(7-bromo-2-oxo-2H-quinolin-1-yl)-N-[(R)-3-(2,3-dihydro-benzo[1,4]dioxin-6-yl)-2-oxo-oxazolidin-5-ylmethyl]-propionamide;

3-(7-bromo-2-oxo-2H-quinolin-1-yl)-N-[(R)-2-oxo-3-(3-oxo-3,4-dihydro-2H-benzo[1,4]thiazin-6-yl)-oxazolidin-5-ylmethyl]-propionamide;

N-[(R)-3-(2,3-dihydro-benzo[,4]dioxin-6-yl)-2-oxo-oxazolidin-5-ylmethyl]-3-(7-methoxy-2-oxo-2H-quinoxalin-1-yl)-propionamide;

3-(7-methoxy-2-oxo-2H-quinolin-1-yl)-N-[(R)-2-oxo-3-(3-oxo-3,4-dihydro-2H-benzo[1,4]thiazin-6-yl)-oxazolidin-5-ylmethyl]-propionamide;

(S)-2-amino-N-[(R)-3-(2,3-dihydro-benzo[1,4]dioxin-6-yl)-2-oxo-oxazolidin-5-ylmethyl]-3-(7-methoxy-2-oxo-2H-quinoxalin-1-yl)-propionamide;

(R)-2-amino-N-[(R)-3-(2,3-dihydro-benzo[1,4]dioxin-6-yl)-2-oxo-oxazolidin-5-ylmethyl]-3-(7-methoxy-2-oxo-2H-quinoxalin-1-yl)-propionamide;

6-((R)-5-{[(R)-2-hydroxy-3-(7-methoxy-2-oxo-2H-quinolin-1-yl)-propylamino]-methyl}-2-oxo-oxazolidin-3-yl)-4H-benzo[1,4]oxazin-3-one;

6-((R)-5-{[(R)-2-hydroxy-3-(7-methoxy-2-oxo-2H-quinolin-1-yl)-propylamino]-methyl}-2-oxo-oxazolidin-3-yl)-4H-benzo[1,4]thiazin-3-one;

6-((R)-5-{[(S)-2-hydroxy-3-(7-methoxy-2-oxo-2H-quinolin-1-yl)-propylamino]-methyl}-2-oxo-oxazolidin-3-yl)-4H-benzo[1,4]thiazin-3-one;

7-fluoro-6-((R)-5-{[(S)-2-hydroxy-3-(7-methoxy-2H-quinolin-1-yl)-propylamino]-methyl}-2-oxo-oxazolidin-3-yl)-4H-benzo[1,4]thiazin-3-one;

6-methoxy-4-(3-{[(R)-2-oxo-3-(3-oxo-3,4-dihydro-2H-benzo[1,4]thiazin-6-yl)-oxazolidin-5-ylmethyl]-amino}-propyl)-4H-pyrido[2,3-b]pyrazin-3-one;

4-(3-{[(R)-3-(2,3-dihydro-benzo[1,4]dioxin-6-yl)-2-oxo-oxazolidin-5-ylmethyl]-amino}-propyl)-6-methoxy-4H-pyrido[2,3-b]pyrazin-3-one;

6-methoxy-4-(3-{[(R)-2-oxo-3-(3-oxo-3,4-dihydro-2H-benzo[1,4]oxazin-6-yl)-oxazolidin-5-ylmethyl]-amino}-propyl)-4H-pyrido[2,3-b]pyrazin-3-one;

6-methoxy-4-(2-{2-[(R)-2-oxo-3-(3-oxo-3,4-dihydro-2H-benzo[1,4]thiazin-6-yl)-oxazolidin-5-yl]-ethylamino}-ethyl)-4H-pyrido[2,3-b]pyrazin-3-one;

6-methoxy-4-(2-{2-[(R)-2-oxo-3-(3-oxo-3,4-dihydro-2H-benzo[1,4]oxazin-6-yl)-oxazolidin-5-yl]-ethylamino}-ethyl)-4H-pyrido[2,3-b]pyrazin-3-one;

6-methoxy-4-(1-{2-[(R)-2-oxo-3-(3-oxo-3,4-dihydro-2H-benzo[1,4]thiazin-6-yl)-oxazolidin-5-yl]-ethyl}-azetidin-3-yl)-4H-pyrido[2,3-b]pyrazin-3-one;

6-methoxy-4-(1-{3-[(R)-2-oxo-3-(3-oxo-3,4-dihydro-2H-benzo[1,4]thiazin-6-yl)-oxazolidin-5-yl]-propyl}-azetidin-3-yl)-4H-pyrido[2,3-b]pyrazin-3-one;

6-methoxy-4-(1-{2-[(S)-2-oxo-3-(3-oxo-3,4-dihydro-2H-benzo[1,4]thiazin-6-yl)-oxazolidin-5-yl]-ethyl}-azetidin-3-yl)-4H-pyrido[2,3-b]pyrazin-3-one;

4-((R)-2-hydroxy-3-{[(R)-2-oxo-3-(3-oxo-3,4-dihydro-2H-benzo[1,4]thiazin-6-yl)-oxazolidin-5-ylmethyl]-amino}-propyl)-6-methoxy-4H-pyrido[2,3-b]pyrazin-3-one;

4-((R)-3-{[(R)-3-(2,3-dihydro-benzo[1,4]dioxin-6-yl)-2-oxo-oxazolidin-5-ylmethyl]-amino}-2-hydroxy-propyl)-6-methoxy-4H-pyrido[2,3-b]pyrazin-3-one;

4-((R)-2-hydroxy-3-{[(R)-2-oxo-3-(3-oxo-3,4-dihydro-2H-benzo[1,4]oxazin-6-yl)-oxazolidin-5-ylmethyl]-amino}-propyl)-6-methoxy-4H-pyrido[2,3-b]pyrazin-3-one; and 1-(3-{[(R)-3-(2,3-dihydro-benzo[1,4]dioxin-6-yl)-2-oxo-oxazolidin-5-ylmethyl]-amino}-propyl)-7-methoxy-3,4-dihydro-1H-quinolin-2-one;

4-(3-{[(R)-3-(3-fluoro-4-methyl-phenyl)-2-oxo-oxazolidin-5-ylmethyl]-amino}-propyl)-6-methoxy-4H-pyrido[2,3-b]pyrazin-3-one;

6-methoxy-4-{1-[(R)-2-oxo-3-(3-oxo-3,4-dihydro-2H-benzo[1,4]thiazin-6-yl)-oxazolidin-5-ylmethyl]-azetidin-3-yl}-4H-pyrido[2,3-b]pyrazin-3-one;

4-(2-{2-[3-(2,3-dihydro-[1,4]dioxino[2,3-c]pyridin-7-yl)-2-oxo-oxazolidin-5-yl]-ethylamino}-ethyl)-6-methoxy-4H-pyrido[2,3-b]pyrazin-3-one;

4-(2-{2-[3-(2,3-dihydro-[1,4]-dioxino[2,3-b]pyridin-6-yl)-2-oxo-oxazolidin-5-yl]-ethylamino}-ethyl)-6-methoxy-4H-pyrido[2,3-b]pyrazin-3-one;

6-(5-{2-[2-(6-methoxy-3-oxo-3H-pyrido[2,3-b]pyrazin-4-yl)-ethylamino]-ethyl}-2-oxo-oxazolidin-3-yl)-4H-pyrido[3,2-b][1,4]oxazin-3-one;

4-(1-{2-[(R)-3-(4-ethoxy-phenyl)-2-oxo-oxazolidin-5-yl]-ethyl}-azetidin-3-yl)-6-methoxy-4H-pyrido[2,3-b]pyrazin-3-one; or 6-methoxy-2-methyl-4-(3-{[(R)-2-oxo-3-(3-oxo-3,4-dihydro-2H-benzo[1,4]thiazin-6-yl)-oxazolidin-5-ylmethyl]-amino}-propyl)-4H-pyrido[2,3-b]pyrazin-3-one:

or a salt of such a compound.

12. A pharmaceutical composition comprising, as active principle, compound of Formula (I) according to claim 1 or a pharmaceutically acceptable salt thereof, and at least one therapeutically inert excipient.

13. A method for treating a bacterial infection comprising administering a compound of Formula (I) according to claim 1, or of a pharmaceutically acceptable salt thereof to a subject in need thereof.

14. A composition comprising the compound of Formula I as defined in claim 1, or a pharmaceutically acceptable salt thereof, in an amount effective to treat a bacterial infection and at least one therapeutically inert excipient.

15. A compound of Formula ($I_{P1}$) according to claim 3, wherein the stereocenter at position 5 of the oxazolidin-2-one ring is in (R)-configuration or a salt of such a compound.

16. A compound of Formula ($I_{P1}$) according to claim 3, wherein U, V and W each represent CH, or U and V each represent CH and W represents N, or U and W each represent N and V represents CH;

or a salt of such a compound.

17. A compound of Formula ($I_{P1}$) according to claim 3, wherein $R^1$ represents $(C_1-C_4)$alkoxy;

or a salt of such a compound.

18. A compound of Formula ($I_{P1}$) according to claim 3, wherein A represents —$CH_2$—$CH(R^2)$-B-NH—*;

or a salt of such a compound.

19. A compound of Formula ($I_{P1}$) according to claim 17, wherein B represents $CH_2$ and $R^2$ represents hydrogen or OH;

or a salt of such a compound.

20. A compound of Formula ($I_{P1}$) according to claim 3, wherein A represents —$CH(R^3)$—$CH_2$—$N(R^4)$—$[CH_2]_m$—* wherein in $R^3$ and $R^4$ together form a methylene bridge and m represents the integer 1 or 2;

or a salt of such a compound.

21. A compound of Formula ($I_{P1}$) according to claim 3, wherein G represents 3-fluoro-4-methyl-phenyl, 4-ethoxy-phenyl, 2,3-dihydro-benzo[1,4]dioxin-6-yl, 2,3-dihydro-[1,4]dioxino[2,3-c]pyridin-7-yl, 2,3-dihydro-[1,4]dioxino[2,3-b]pyridin-6-yl, 3-oxo-3,4-dihydro-2H-benzo[1,4]oxazin-6-yl, 3-oxo-3,4-dihydro-2H-pyrido[3,2-b][1,4]oxazine-6-yl, 3-oxo-3,4-dihydro-2H-benzo[1,4]thiazin-6-yl or 7-fluoro-3-oxo-3,4-dihydro-2H-benzo[1,4]thiazin-6-yl;

or a salt of such a compound.

22. A pharmaceutical composition comprising a compound of Formula ($I_{P1}$) according to claim 3 or a pharmaceutically acceptable salt thereof, and at least one therapeutically inert excipient.

23. A method for treating a bacterial infection comprising administering a compound of Formula ($I_{P1}$) according to claim 3, or of a pharmaceutically acceptable salt thereof.

* * * * *